United States Patent [19]
Rine et al.

[11] Patent Number: 6,107,462
[45] Date of Patent: Aug. 22, 2000

[54] GENES AND PROTEINS CONTROLLING CHOLESTEROL SYNTHESIS

[75] Inventors: Jasper D. Rine, Moraga; Randolph Hampton, San Diego, both of Calif.

[73] Assignee: The Regents of the University of California, Berkeley, Calif.

[21] Appl. No.: 08/699,103

[22] Filed: Aug. 16, 1996

Related U.S. Application Data

[60] Provisional application No. 60/002,381, Aug. 17, 1995.

[51] Int. Cl.[7] ............................. C07K 1/00; C07H 21/04; C12P 21/06
[52] U.S. Cl. ..................... 530/350; 536/23.5; 536/23.7; 435/69.1
[58] Field of Search ........................ 530/350; 536/23.5, 536/23.7; 435/69.1

[56] References Cited

U.S. PATENT DOCUMENTS

| | | | |
|---|---|---|---|
| 5,356,896 | 10/1994 | Kabadi et al. | 514/256 |
| 5,491,164 | 2/1996 | deSolms et al. | 514/423 |
| 5,523,456 | 6/1996 | Stokker et al. | 560/10 |
| 5,532,359 | 7/1996 | Marsters, Jr. et al. | 540/522 |

OTHER PUBLICATIONS

Ashby and Rine, 1995, *Methods in Enzymology,* 250:235–250.
Basson et al., 1988, *Mol. Cell Biol.,* 8:3797–3808.
Boeke et al., 1987, *Methods Enzymol,* 154:164–175.
Chen et al., 1995, *Embo Journal,* 14(11):2620–2630.
DeMarini et al., 1995, *Mol. Cell Biol.,* 15:6311–6321.
DeMartino et al., 1994, *J. Biol. Chem,* 269:20878–20884.
Egner and Kuchler, 1996, *Febs Lett,* 378:177–181.
Evan et al., 1985, *Mol. Cell Biol.,* 5:3610–3616.
Freemont, 1993, *Ann NY Acad Sci,* 684:174–192.
Gietz and Sugino, 1988, *Gene,* 74:527–534.
Goldberg, 1995, *Science,* 268(5210):522–523.
Grant and Greenwald, 1996, *Genetics,* 143:237–247.
Hampton et al., 1996, "Role of 26S Proteasome and HRD Genes in the Degradation of 3–Hydroxy–3–Methylglutaryl–CoA Reductase, an Integral Endoplasmic Reticulum Membrane Protein," *Molecular Biology of the Cell* 7:2029–2044.
Hampton et al., 1996, *Proc. Natl. Acad. Sci. USA,* 93:828–833.
Hampton and Rine, 1994, *J. Cell Biol.,* 125:299–312.
Heilmeyer, Jr. et al., Oct. 1992, *Proc. Natl. Acad. Sci. USA,* 89:9554–9558.
Hicke and Riezman, 1996, *Cell,* 84:277–287.
Higgins and Sharp, 1989, *CABIOS,* 5:151–153.
Higgins and Sharp, 1988, *Gene,* 73:237–244.
Hilt and Wolf, 1995, *Mol Biol Rep,* 21:3–10.
Hrycyna, et al., 1991, *EMBO Journal,* 10(7):1699–1709.
Inoue et al., 1991, *J. Biol Chem,* 266:13311–13317.
Jensen et al., 1995, *Cell,* 83:129–135.
Kato et al., Jul. 1992, *Proc. Natl. Acad. Sci. USA,* 89:6403–6407.
Lecureux and Wattenberg, 1994, *J. Cell Science,* 107:2635–2642.
Lorenz et al., 1995, *Gene,* 158:113–117.
McCracken and Brodsky, 1996, *J Cell Biol,* 132:291–298.
Meyers and Miller, 1988, *Computer Applic. Biol. Sci.,* 4:11–17.
Papa and Hochstrasser, 1993, *Nature,* 366:313–319.
Rechsteiner et al., 1993, *Journal of Biological Chemistry,* 268(9):6065–6068.
Rose et al., 1987, *Gene,* 60:237–243.
Sipos and von Heijne, 1993, *Eur. J. Biochem,* 213:1333–1340.
Song et al., 1995, *J. Biol. Chem.,* 270:3574–3581.
Tanaka et al., 1992, *New Biologist,* 4(3):173–187.
Tierney et al., 1992, *Arch Biochem Biophys,* 293:9–16.
Ward et al., 1995, *Cell,* 83:121–127.
Weirtz et al., 1996, *Cell,* 84:769–779.
Johnston et al., Science 265:2077–2082, 1994.

*Primary Examiner*—Robert A. Wax
*Assistant Examiner*—Tekchand Saidha
*Attorney, Agent, or Firm*—Fish & Richardson P.C.

[57] ABSTRACT

The present invention provides isolated nucleic acid sequences which encode a family of HMG-CoA Reductase Degradation (HRD) polypeptides. More particularly, the present invention provides isolated HRD1, HRD2 and HRD3 nucleic acids and the Hrd polypeptides encoded by such nucleic acids, i.e., Hrd1, Hrd2 and Hrd3, respectively. Vectors comprising the nucleic acids are provided. In addition, the present invention provides screening assay related to cholesterol biosynthesis.

5 Claims, 10 Drawing Sheets

FIG 6

Hrd2p vs. TRAP-2/p97

```
M-EEGGRDKAPV--QPQQSPAAAPGGTDEKPSGKERRDAGDKDKEQELSEEDKQLQDELEMLAER    NDEVLGLLLPIAASTDLPIETAAMASLALAHVFVGTCNGDITTSIMDNFLERTAIELKTDWVRFL
: .:..:. .. :.: ::             1.:.:...                :.: .:: .: :..::::::             .: .:.........::. .  :: .:::::1::.:::.:...::.  :::  .:.:
MVDESDKKQQTIDEQSQISPEK------QTPNKKDKK----KEEEEQLSEEDAKLKTDLELLVER    REDVLTLLLPVMGDSKSSMEVAGVTALACCGMIAVGSCNGDVTSTILQTIMEKSETELKDTYARWL

LKEDDSSLYEASLNALKESIKNSTSSMTAVPKPLKFLRPTYPDLCSIYDKWTDPNLKSSLADVLS    ALALGILYMGQEQVDDVLETISAIEHPMTSAIEVLVGSCAYTGTGDVLLIQDLLHRLTPKNVKG
: : :.::::.. :: .:....::.:::::::::::: : :  ::.:.:.. . .:  ::...:    :...:.::  .. .:::   ..:.:.:...  .:: :::::.:..:::  .:.::: :
LGEKDTSLYRPALEELRRQIRSSTTSMTSVPKPLKFLRPHYGKLKEIYENMAPGENKRFAADIIS    PLGLGLNHLGKGEAIEAILAALEVVSEPFRSFANTLVDVCAYAGSGNVLKVQQLLH---------

ILAMTYSENGKHDSLRYRLLSDVSDFEGWGHEYIRHLALEIGEVYNDQVEKDAEDETSSDGSKSD    EEDADEEETAEGQTNSISDFLGEQVNEPTKNEEAEIEVDEMEVDAEGEEVEVKAEITEKKNGESL
.::::. :.... :..:  :..:::. .. .:::::.::::                :: :.. :                                                                .
VLAMTMS--GERECLKYRLVGSQEELASWGHEYVRHLA---GEVAKEWQELD------DAEK--    I

GSAATSGFEFSKEDTLRLCLDIVPYFLKHNGEEDAVDLLLEIESIDKLPQFVDENTFQRVCQYMV    EGEEIKSEEKKGKSSDKDATTDGKNDDEEEEKEAGIVDELAYAVLGIALIALGEDICKEMSLRHF
.: :  .:.:::: : ::::: :: ..:..:: .:...:::.:: .::. ::::. ::  ::  ::    .:::.:.::.       :::      :::::::::::  ::::::::  .::..:
--------VQREPLLTLVKEIVPYNMAHNAEHEACDLLMEIEQVDMLEKDIDENAYAKVCLYLT    CSEHFDSKEKE---EDKDKKE--KKDKDKKEAPADMGAHQQVAVLGIALIAMGEEIGAEMALRTF

ACVPLLPPEDVAFLKTAYSIYLSQNELTDAIALAVRLGEEDMIRSVFDATSDPVMHKQLAYILA    GHLMHYGNEHIRRMVPLAMGIVSVSDPQMKVFDTLTRFSHDADLEVSMNSIFAMGLCGAGTNNAR
.:  .:: ::  : .:. .: .  .. :. :::  .: .: :  .:  ..:. :  .: .:..:.    :::::. ..:.:::::.:.:: .:..::::::: .::..::::::::: . .:::::::.
SCVNYVPEPENSALLRCALGVFRKFSRFPEALRLALMLNDMELVEDIFTSCKDVVVQKQMAFMLG    GHLLRYGEPTLRRAVPLALALISVSNPRLNILDTLSKFSHDADPEVSYNSIFAMGVGSGTNNAR

AQKTSFE-------YEGVQDIIGNGKLLSEHFLYLAKELNLTGPKVPEDIYKSHLDNSKSVFSSAG    LAQLLRQLASYYSREQDALFITRLAQGLLHLGKGTMTMDVFN-DAHVLNKVTLASILTTAVGL--
 . .:         :..    :::: : .: .:: ..:: ::::.:..:.                 :: .:::::::::.  ::::::::: :::::::::::  .   . :. . :.:.::..
RHGVFLELSEDVEEYEDLTEIMSNVQLNSNFLALARELDIMEPKVPDDIYKTHLENNRFGGSGSQ    LAAMLRQLAQYHAKDPNNLFMVRLAQGLTHLGKGTITLCPYHSDRQLMSQVAVAGLLTVLVSFLD

LDSAQQONLASSFVNGFLNLGYCNDKLIVDNDN-WVYKTKGDGMTSAVASIGSIYQWNLDG-LQQL    VSPSFMLKHHQLFYMLNAGIRPKFILALNDEGEPIKVNVRVGQAVETVGQAGRPKKITGWITQST
.: :..:.::::::::: :: .: ::...     : .:..:  :   .:  ::. .  ::       :  .. .: .. :... .. :    :. : :::.:.:: ::::.:: :::  :
VDSARMNLASSFVNGFVNAAFGQDKLLTDDGNKWLYKNKDHGMLSAAASLAMILLMVDVDGGLTQI    VRNIILGKSHYVLYGLVAAMQPRMLVTFDEELRELPVSVRVGQAVDVVGQAGKPKTITGFQTHTT

DKYLYVDEPEVKAGALLGIGISASGVHDGEVEPALLLLQDYVTNPDTKISSAAILGLGIAFAGSK    PVLLNHGERAELETDEYISYTSHIEGVVILKKNPDYREEEZ
::::: :.:  :..:::::.:  ::::: :. :::: .:.::.:   ... . .::.::.:.:    :::: :::::::: :::::.  .  .:: :::.::..:
DKYLYSSEDYIKSGALLACGIVNSGVRN-ECDPALALLSDYVLHNSNTMRLGSIFGLGLAYAGSN    PVLLAHGERAELATEEFLPVTPILEGFVILRKNPNY---DL
```

FIG 9

```
Hrd3p(184-218)       LGNLKAKQVLAYKYYSGFNVPRNFHKSLVLYRDIAEQLRKSY
Hrd3p(625-666)       KYSIQAIWNLGYMHEHGLGVNRDFHLAKRYYDQVSEHDHRFY
sel-1(629-657)                 QAMFNLGYMHEVGEGITRDLYLAKRFYDQAIEHSQDAY
Ibd2(23-57)                QHSAQAMFNLGYMHEKGLGIKQDIHLAKRFYDMAA
S.p.unknown(1-23)                     MHEYGVGVPVDFEMXKXNYDNAXMXDTRAF
```

A

```
  1 ........................SDYRWFPQLPGLSSPRTLQY..... 20
                            |.: :||..|.....|.|
151 VMYATGGCASGNDQTVIPQDSAKALLYYQRAAQLGNLKAKQVLAYKYYSG 200

21 ........................IFPPFLEGFRC........ 31
                            |. |::|::..
201 FNVPRNFHKSLVLYRDIAEQLRKSYSRDEWDIVFPYWESYNVRISDFESG 250

32 .FPKXLDERSSSVGRFWALWLGFCN....................FSLGT 60
    :.| |:. .||..| :. : ::..                    |.:..
251 LLGKGLNSVPSSTVRKRTTRPDIGSPFIAQVNGVQMTLQIEPMGRFAFNG 300

61 ............AVEPHPLWIIIATXR.WKSSW...RATTRRKKMQT.. 91
                | |.: ::|..|. . :|:.:  |...| |.: .
301 NDGNINGDEDDEDASERRIIRIYYAALNDYKGTYSQSRNCERAKNLLELT 350
```

```
  1 ..............................................MGLDTDV 7
                                                  .:|.:|
551 YETAQVSAAYLMYQLPYEFEDPPRTTDQRKTLAISYYTRAFKQGNIDAGV 600

8 DYETAFIHYRLASEQ.........QHSAQAMFNLGYMHEKGLGIKQDIHL 48
    :. ::: . |..       ..| ||::|||||||.|||:..|:||
601 VAGDIYFQMQNYSKAMALYQGAALKYSIQAIWNLGYMHEHGLGVNRDFHL 650

49 AKRFYDMAAVSQPRCTSSSLPSPLQIGHRLFLAVHTGNKHSRYVLPT... 95
    |||:|| .. :.| .| |.|.: : :|. | :| . : ..
651 AKRYYDQVSEHDHRFYLASKLSVLKLHLKSWLTWITREKVNYWKPSSPLN 700
```

Figure 10B

GENES AND PROTEINS CONTROLLING CHOLESTEROL SYNTHESIS

CROSS REFERENCE TO RELATED APPLICATIONS

This application is a continuation-in-part of U.S. provisional application number 60/002,381, filed Aug. 17, 1995, naming Rine and Hampton as inventors.

BACKGROUND OF THE INVENTION

Although de novo synthesis of cholesterol occurs in virtually all cells, this capacity is greatest in liver, intestine, adrenal cortex and reproductive tissues, including ovaries, testes and placenta. From an inspection of its structure, it is apparent that cholesterol biosynthesis requires a source of carbon atoms and considerable reducing power to generate the numerous carbon-hydrogen and carbon-carbon bonds. All of the carbon atoms of cholesterol are derived from acetate. Reducing power in the form of NADPH is provided mainly by enzymes of the hexose monophosphate shunt, specifically, glucose 6-phosphate dehydrogenase and 6-phosphogluconate dehydrogenase. The mevalonate pathway, i.e., the pathway of cholesterol synthesis, occurs in the cytoplasm and is driven in large part by the hydrolysis of the high-energy thioester bonds of acetyl CoA and the high-energy phosphoanhydride bonds of ATP. For a detailed discussion of the mevalonate pathway, see, e.g., Stryer, L., *BIOCHEMISTRY*, Third Edition (W.H. Freeman And Company/New York (1988)).

The first committed step in the mevalonate pathway is the synthesis of mevalonic acid, which is derived from acetyl CoA. Acetyl CoA can be obtained from several sources: (a) the β oxidation of long-chain fatty acids; (b) the oxidation of ketogenic amino acids such as leucine and isoleucine; and (c) the pyruvate dehydrogenase reaction. In addition, free acetate can be activated to its thioester derivative at the expense of ATP by the enzyme acetokinase, which is also referred to as acetate thiokinase.

The first two steps in the mevalonate pathway are shared by the pathway that also produces ketone bodies. Two molecules of acetyl CoA condense to form acetoacetyl CoA in a reaction catalyzed by acetoacetyl CoA thiolase (acetyl CoA: acetyl CoA acetyltransferase). The next step introduces a third molecule of acetyl CoA in the cholesterol pathway and forms the branched-chain compound 3-hydroxy-3-methylglutaryl CoA (HMG CoA). This condensation reaction is catalyzed by HMG CoA synthase (3hydroxy-3-methylglutaryl CoA: acetoacetyl CoA lyase). Liver parenchymal cells contain two isoenzyme forms of HMG CoA synthase; one is found in the cytosol and is involved in cholesterol synthesis, while the other has a mitochondrial location and functions in the pathway that forms ketone bodies. In the HMG CoA synthase reaction, an aldol condensation occurs between the methyl carbon of acetyl CoA and the β-carbonyl group of acetoacetyl CoA with the simultaneous hydrolysis of the thioester bond of acetyl CoA.

The step that produces the unique compound mevalonic acid from HMG CoA is catalyzed by the important microsomal enzyme HMG CoA reductase (mevalonate: NADP+ oxidoreductase) that has an absolute requirement for NADPH as the reductant. This reduction reaction is irreversible and produces (R)-(+) mevalonate, which contains six carbon atoms. HMG CoA reductase catalyzes the rate-limiting reaction in the pathway of cholesterol biosynthesis. HMG CoA reductase is an intrinsic membrane protein of the endoplasmic reticulum whose carboxyl terminus extends into the cytoplasm and carries the enzyme's active site.

Mevalonate is converted into 3-isopentenyl pyrophosphate by three consecutive reactions involving ATP. In the last step, the release of $CO_2$ from 5-pyrophosphomevalonate occurs in concert with the hydrolysis of ATP to ADP and $P_i$. Thereafter, squalene is synthesized from 3-isopentenyl pyrophosphate by the reaction sequence:

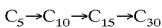

$$C_5 \rightarrow C_{10} \rightarrow C_{15} \rightarrow C_{30}$$

This stage in the mevalonate pathway starts with the isomerization of isopentenyl pyrophosphate to dimethylallyl pyrophosphate. These isomeric $C_5$ units condense to form a $C_{10}$ compound: an allelic carbonium formed from dimethylallyl pyrophosphate is attacked by isopentenyl pyrophosphate to form geranyl pyrophosphate. The same kind of reaction occurs again: geranyl pyrophosphate is converted into an allelic carbonium ion, which is attacked by isopentenyl pyrophosphate. The resulting $C_{15}$ compound is called farnesyl pyrophosphate. The last step in the synthesis of squalene is a reductive condensation of two molecules of farnesyl pyrophospate.

The final stage of the mevalonate pathway starts with the cyclization of squalene. This stage, in contrast to the preceding ones, requires molecular oxygen. Squalene epoxide, the reactive intermediate, is formed in a reaction that uses $O_2$ and NADPH. Squalene epoxide is then cyclized to lanosterol by a cyclase. There is a concerted movement of electrons through four double bonds and a migration of two methyl groups in this remarkable closure. Finally, lanosterol is converted into cholesterol by the removal of three methyl groups, the reduction of one double bond by NADPH, and the migration of the other double bond.

From the foregoing, it is apparent that the mevalonate pathway is responsible for the synthesis of a wide variety of essential and clinically relevant molecules. Products from the mevalonate pathway include, for example, cholesterol and the prenyl groups which are required for the function of numerous small GTP binding proteins including the RAS oncoprotein. The connection of the mevalonate pathway, by virtue of its products, to many clinically important processes, such as atherosclerosis and RAS-based cancers, has led to a significant effort to understand the cellular regulation of the mevalonate pathway. It has been found that the mevalonate pathway is regulated by feedback control of several pathway enzymes, the principal one of which is 3-hydroxy-3-methylglutaryl CoA (HMG-CoA) reductase, the rate-limiting enzyme of cholesterol synthesis. Feedback regulation of HMG-CoA reductase occurs through modulation of the steady-state amount of protein by the coordinated adjustment of synthesis and degradation rates. Thus, when the mevalonate pathway products are abundant, the synthetic rate of HMG-CoA reductase is low, the degradation rate of HMG-COA reductase is rapid, and through both of these actions, the steady state of the enzyme is kept low. Conversely, when production of the mevalonate pathway products is slowed, the synthetic rate of the HMG-COA reductase is increased, the degradation rate of HMG-CoA reductase is slowed and, consequently, the steady-state level of HMG-COA reductase is elevated. To date, the molecular signals which control the synthesis and degradation of HMG-COA reductase are unknown. However, it is known that the control of HMG-CoA reductase degradation is genetically distinct from the control of HMG-CoA reductase synthesis, implying that distinct molecular mechanisms are responsible for these independent features of HMG-CoA reductase regulation.

The feedback regulation of the mevalonate pathway plays a central role in the clinical management of hypercholesterolemia. The current drugs of choice for lowering serum cholesterol are the structurally related, competitive inhibitors of HMG-CoA reductase which include, for example, the widely used Mevacor®, the tradename for lovastatin. These agents were developed specifically for the purpose of inhibiting HMG-CoA reductase. HMG-CoA reductase was thought to be the best target for clinical control of the pathway because this enzyme is most strongly regulated in the physiological control of the cholesterol pathway. However, when a patient is put on an inhibitor of HMG-CoA reductase, the coordinated feedback regulation of HMG-CoA reductase synthesis and degradation brings about a compensatory increase of HMG-CoA reductase levels which abrogates most of the effect of the drug on body cholesterol synthesis. The beneficial effects of HMG-CoA reductase inhibitors, such as Mevaco®, are thought to occur by increased clearance of plasma LDL brought about by the parallel up-regulation of the LDL receptor (LDL-R). Thus, the feedback signals from the mevalonate pathway severely limit the efficacy of such treatments on cholesterol synthesis, but, at the same time, are necessary for the beneficial effects of cholesterol clearing caused by drugs such as Mevacor®.

From the foregoing, it is apparent that the potentially simple solution of interfering with the feedback signals from the mevalonate pathway in order to block the up-regulation of HMG-CoA reductase would also remove the beneficial increase of LDL receptors brought about by the same signals. Moreover, although the possibility exists that the detrimental up-regulation of HMG-CoA reductase synthesis could be specifically blocked without affecting the beneficial up-regulation of the LDL-R, the mechanistic similarity of the two processes may make this separation an unrealistic goal. As such, there remains a need in the art for appropriate molecular targets which can be used to manipulate the levels of HMG-CoA reductase in a manner which is independent of the beneficial LDL receptor control axis.

Another problem in the art is the function of many nucleic acid and polypeptide sequences on deposit in various sequence repositories. For example, one good system for studying the regulation of HMG-CoA is yeast, which encode an HMG-CoA reductase homologue. However, despite the fact that the entire yeast genome has been sequenced and the sequences deposited in GenBank™ and other sequence repositories, the relationship of many yeast genes to HMG-CoA reductase regulation is unknown. Elucidation of the complete yeast genome in the absence of functional information for a particular yeast gene is insufficient for identification of any particular gene product. Although many open reading frames (ORFS) have been identified, it is often not known whether these ORFs encode functional mRNAs, or what the function of the putative genes would be. Similarly, many eukaryotic sequences (e.g., human sequences) have been deposited in GenBank™ and other sequence repositories without any functional information for the sequences being available. In the absence of knowledge regarding the function of a given sequence, there is no reason to select the sequences for cloning into vectors, e.g., for expression of the nucleic acids and encoded proteins. In the absence of functional information, any relationship between deposited sequences and HMG-CoA reductase is unknown.

SUMMARY OF THE INVENTION

The present invention provides isolated nucleic acid sequences which encode a family of HMG-CoA Reductase Degradation (HRD) polypeptides. More particularly, the present invention provides isolated HRD1, HRD2 and HRD3 nucleic acids, vectors which replicate and/or express the nucleic acids, and Hrd polypeptides encoded by the nucleic acids, i.e., Hrd1p, Hrd2p and Hrd3p, respectively. It is now discovered that the Hrd polypeptides of the present invention regulate the degradation of HMG-CoA reductase, the enzyme which catalyzes the rate-limiting reaction in the pathway of cholesterol biosynthesis. As such, the Hrd polypeptides of the present invention can be used to regulate the degradation of HMG-CoA reductase. Moreover, the Hrd polypeptides of the present invention can be used in various assays to identify other compounds which can be used to modify the degradation of HMG-CoA reductase.

As such, in one aspect, the present invention provides isolated nucleic acids, i.e., polynucelotides, which encode the Hrd family of polypeptides. More particularly, the present invention provides an isolated nucleic acid which encodes a Hrd2p polypeptide, for example, the nucleic acid having the sequence set forth in SEQ ID NO:1. The present invention provides an isolated nucleic acid which encodes a Hrd3p polypeptide, for example, the nucleic acid having the sequence set forth in SEQ ID NO:2. In addition, the present invention provides an isolated nucleic acid encoding a polypeptide which is the human homologue of Hrd3p. Nucleic acids and corresponding polypeptides for Hrd1p are also provided. Vectors which include HRD nucleic acids are also a feature of the invention.

In another aspect, the present invention provides Hrd polypeptides which have the ability to modify the degradation of HMG-CoA reductase in a manner that is independent of the beneficial LDL receptor control axis. More particularly, the present invention provides a Hrd2 polypeptide which is encoded by the HRD2 nucleic acid having the sequence set forth in SEQ ID NO:1. The Hrd2p polypeptide is a soluble polypeptide having a molecular weight of about 109 kD with an amino acid sequence corresponding, for example, to SEQ ID NO: 3. In addition to Hrd2p, the present invention provides a Hrd3p polypeptide which is encoded, for example, by the HRD3 nucleic acid having the sequence set forth in SEQ ID NO:2. Hrd3p is a type I membrane polypeptide (i.e., the N-terminus is in the cytosol) having a molecular weight of about 99 kD, with a single membrane spanning sequence. An amino acid sequence of the polypeptide encoded by HRD3 is set forth in SEQ ID NO:4. It has been determined that when Hrd1p, Hrd2p and Hrd3p are supplied by trans complementation, they are able to restore Hrd1p-, Hrd2p- and Hrd3p-dependent HMG-CoA reductase degradation. In addition to the Hrd polypeptides isolated from yeast, the present invention provides the corresponding homologous human polypeptides. For example, the present invention provides a polypeptide which is the human homologue of Hrd3p. This polypeptide comprises amino acid sequences encoded by the nucleic acids set forth in SEQ ID NO:5 and SEQ ID NO:6. A Hrd3p human homologue subsequence is set forth in SEQ ID NO:8.

In one class of embodiments, the present invention provides a vector, such as a plasmid, virus or the like, which includes a nucleic acid that encodes a Hrd polypeptide, such as Hrd1p, a conservatively modified Hrd1p, Hrd2p, a conservatively modified Hrd2p, Hrd3p, or a conservatively modified Hrd3p polypeptide. Exemplary nucleic acid sequences for this purpose include SEQ ID NO:1, SEQ ID NO:2, SEQ ID NO:5, SEQ ID NO:6, and SEQ ID NO:7.

Isolated polypeptides encoded by the vectors, such as the polypeptides of SEQ ID NO:3, SEQ ID NO:4, SEQ ID NO:8; the Hrd1p sequence of FIG. 8 or the Hrd3p sequence of FIG. 8 are also provided.

In one group of embodiments, the invention provides vectors encoding one or more nucleic acids which hybridize under stringent conditions to a nucleic acid which encodes a polypeptide of the invention, such as the Hrd1p polypeptide, conservatively modified Hrd1p polypeptides, the Hrd2p polypeptide, conservatively modified Hrd2p polypeptides, the Hrd3p polypeptide, and a conservatively modified Hrd3p polypeptides. Exemplar nucleic acid subsequences include SEQ ID NO:1, SEQ ID NO:2, SEQ ID NO:5, SEQ ID NO:6, and SEQ ID NO:7. Polypeptides encoded by such vectors are also a feature of the invention.

A class of vectors defined by the immunological reactivity of the encoded polypeptides are provided. The vectors include a nucleic acid that encodes a first polypeptide which is immunologically cross-reactive with a polypeptide of the invention, such as a full-length Hrd1p polypeptide, a full-length Hrd2p polypeptide, or a full-length Hrd3p polypeptide, wherein the first polypeptide, when supplied by trans complementation, restores HRD dependent HMG-Co A reductase degradation in a strain of yeast which does not produce a Hrdp polypeptide selected from the group consisting of Hrd1p, Hrd2p and Hrd3p (e.g., a strain which has a deletion in the gene encoding the specified protein). Exemplar polypeptides include SEQ ID NO:3, SEQ ID NO:4, SEQ ID NO:8; the Hrd1p sequence of FIG. 8 (SEQ ID NO:25) and the Hrd3p sequence of FIG. 8 (SEQ ID NO:4).

In yet another aspect, the present provides a method for identifying a compound that modifies the degradation of HMG-CoA reductase, the method comprising: (i) providing a first solution comprising HMG-CoA reductase, a proteasome and a Hrd polypeptide; (ii) providing a second solution comprising HMG-CoA reductase, a proteasome, the Hrd polypeptide used in step (i) and a test compound; (iii) measuring the rate of HMG-CoA reductase degradation in the first solution and the second solution; and (iv) comparing the rate of HMG-CoA reductase degradation in the first solution with the second solution. If there is a difference between the rate of HMG-CoA reductase degradation in the first solution and the rate of HMG-CoA reductase degradation in the second solution, the compound tested is said to be capable of modifying the degradation of HMG-CoA reductase. In this method of the present invention, the HMG-CoA reductase can be provided in pure form or, alternatively, it can be provided in the form of a microsome or membrane fragment containing endogenous HMG-CoA reductase.

In a further aspect, the present invention provides another method of identifying a compound that modifies the degradation of HMG-CoA reductase, the method comprising: (i) applying the compound to be tested to a yeast strain containing elevated levels of HRD proteins; (ii) applying the compound to be tested to yeast strains containing normal levels of HRD proteins; and (iii) identifying the compounds that inhibit the growth of the first strains more than the growth of the second strains.

The present invention also provides methods of isolating a wild-type gene which regulates the degradation of HMG-CoA reductase, the methods comprising: (i) providing a yeast culture having a form of HMG-CoA reductase which is not regulated by the flux through the mevalonate pathway; (ii) selecting a yeast culture with increasing levels of resistance to a competitive inhibitor of HMG-CoA reductase; and (iii) cloning the wild type gene from a recombinant library by its ability to restore sensitivity to the competitive inhibitor of HMG-CoA reductase. Using these methods, the HRD nucleic acids of the present invention can be readily isolated from other eukaryotic sources. Moreover, using these methods, other members of the HRD family can be identified and isolated.

In another aspect, the present invention provides a method for isolating a wild type gene that encodes a protein involved in signalling for the degradation of HMG-CoA reductase, the method comprising: (i) providing a yeast culture having a form of HMG-CoA reductase whose degradation is low when flux through the mevalonate pathway is low; (ii) applying a mutagen to the culture; (iii) screening the culture for mutant cells that are more sensitive than the non-mutant parent strain to a competitive inhibitor of HMG-CoA reductase; and (iv) using a recombinant library to transform the mutant cells to identify clones capable of restoring to the cells resistance to the inhibitor of HMG-CoA reductase. Mutagens suitable for use in this method include, but are not limited to, chemical mutagens, physical mutagens (e.g., X-ray and the like) and transposons. Generally, the mutant cells of interest are more sensitive than the nonmutant parent strain to a competitive inhibitor of HMG-COA reductase because they constitutively degrade the enzyme.

The present invention further provides kits for identifying a compound which modifies the degradation of HMG-CoA reductase, the kit comprising: a container, HMG-CoA reductase, a Hrd polypeptide and a proteasome. In addition, the present invention also provides a kit for isolating a gene which regulates the degradation of HMG-CoA reductase, the kit comprising a container and a yeast cell isolate which exhibits non-mevalonate dependent Hmg2p degradation. This particular kit may further contain an HMG-CoA reductase inhibitor. The kits of the present invention optionally include instructions for practicing the method.

Other features, objects and advantages of the invention and its preferred embodiments will become apparent from the detailed description which follows.

were prepared from cultures that were diluted at the start of the 15 hour incubation period such that they were in log phase at the time all samples were harvested. All samples were immunoblotted using the anti-HmgRp antiserum used in the Hmg2p samples in B). Note the lowered mobility of the 6myc-Hmg2p protein as compare to the native Hmg2p. The lanes from the 6myc-Hmg2p expressing strain were added with 3 times as much total protein to allow direct comparison of the two signals. D) Lovastatin sensitivity of strains expressing either 6myc-Hmg2p (RHY244) or Hmg2p (RHY183), as marked. Cultures of cells at a low starting $OD_{600}$ (~0.05) were grown in the presence of increasing amounts of lovastatin for 5 days. Final optical densities of cultures at each dose are shown.

Figure 2:
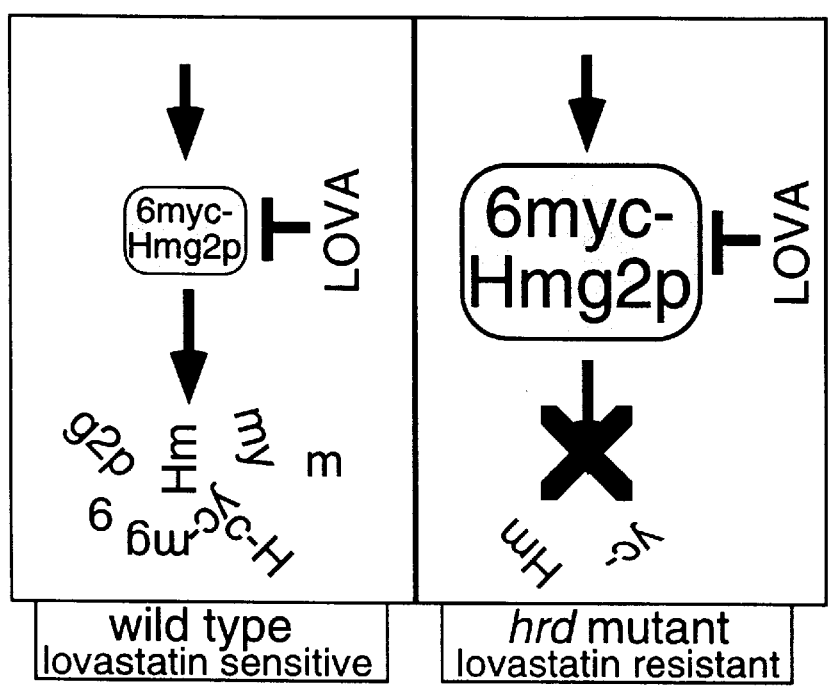

FIG. 2. The HRD selection. The steady-state level of HMG-R activity, and the corresponding sensitivity to lovastatin, is determined by the balance between the synthesis (top arrow) and degradation (bottom arrow) of the 6myc-Hmg2p protein. A strain (RHY244) expressing only the unrelated 6myc-Hmg2p from the GAPDH promoter from a gene integrated into genome was lovastatin sensitive. A mutation that slows degradation (X) caused an increase in the steady-state level of the 6myc-Hmg2p protein, and a corresponding increase in lovastatin resistance.

Figure 3:
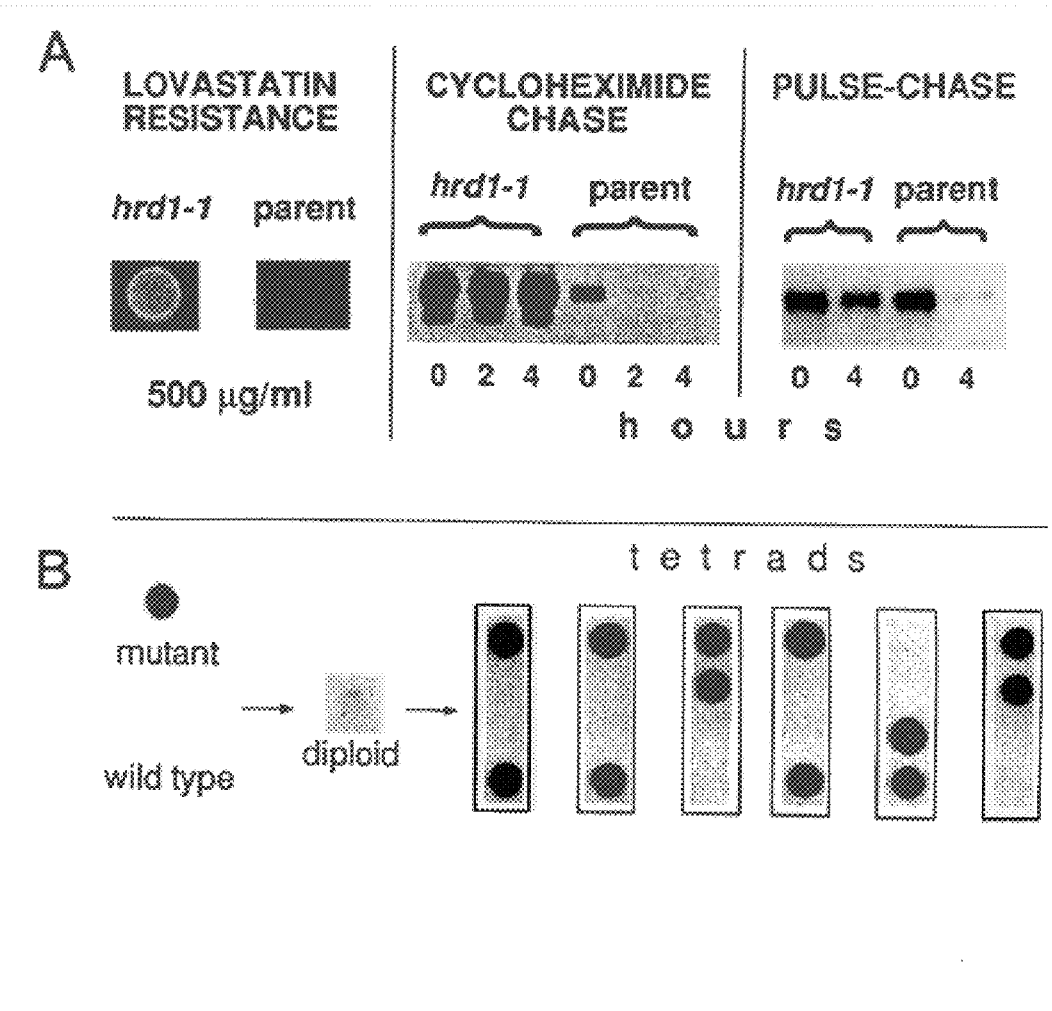

FIG. 3. The hrd1-1 mutant and the Hrd phenotype. A) A profile of the phenotypes of a representative hrd mutant, hrd1-1, relative to wild-type. Lovastatin resistance (left) was tested by spotting 20 μl of an OD 0.1 culture onto supplemented minimal medium with the indicated concentrations of lovastatin and allowing growth for a week. Note that the hrd1-1 strain was resistant to a dose of lovastatin higher than the concentration used in the selection. The degradation of the entire pool of 6myc-Hmg2p (middle panel; "cycloheximide chase") was determined by addition of cycloheximide to log-phase cultures of mutant or wild-type cells at t=0, and subsequently immunoblotting of the lysate with the 9E10 anti-myc antibody. Each lane received lysate from 0.2 OD units of cells. The t=0 lanes indicated that there was increased steady-state 6myc-Hmg2p protein in the mutant. Pulse-chase experiments were performed on each strain, but with the anti-myc 9E10 antibody (10 μl of ascites) as the precipitating antibody (right panel). The t=0 lane revealed that the synthetic rate of the 6myc-Hmg2p protein in each strain was comparable. B) Mendelian genetics of the mutant. Lysates from the hrd1-1 strain, the wild-type parent strain of opposite mating type, the diploid from these two, and the haploid progeny of 6 representative tetrads were analyzed for myc immunoreactivity after growth into stationary phase. Due to the specificity of the myc tag, the lysates were analyzed by dot immunoblotting. A dark signal indicates slow degradation due to the hrd mutation. The mutation was recessive as the diploid had normal degradation of 6myc-Hmg2p, and the phenotype segregated as a single locus, since degradation:stabilization segregated 2:2.

Figure 4:
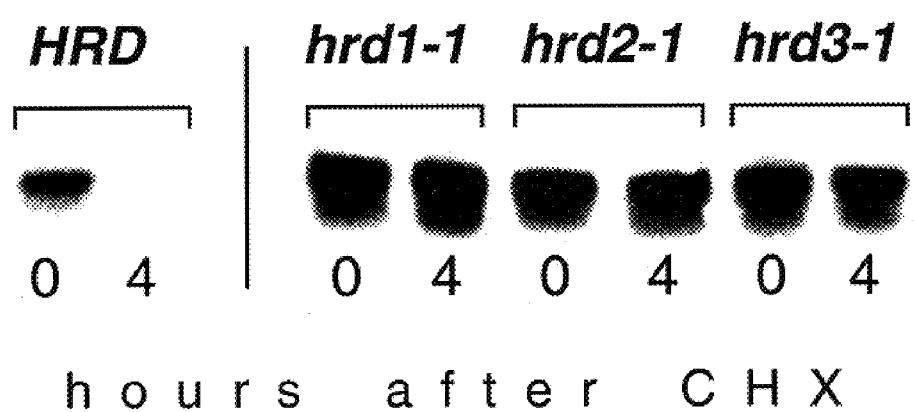

FIG. 4. hrd mutants stabilized normal Hmg2p. Otherwise isogenic strains with indicated hrd genotype and expressing normal Hmg2p in place of the original 6myc-Hmg2p were tested for the degradation of the Hmg2p protein by cycloheximide (CHX) chase, as in FIG. 3a, middle panel. Hmg2p was detected with affinity-purified anti-Hmg1p antibody.

Figure 5:
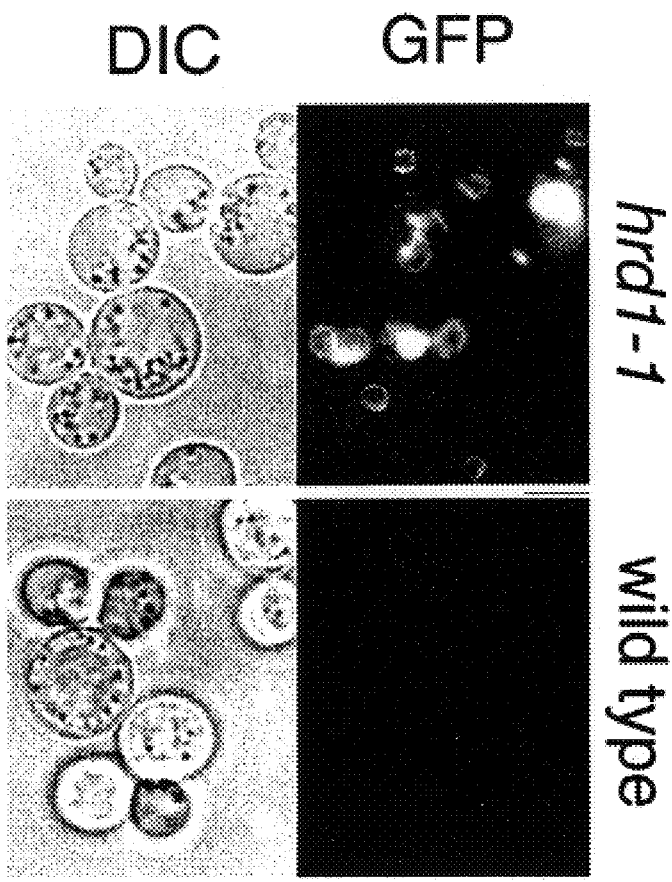

FIG. 5. Stabilization of Hmg2p-CEP by the hrd1-1 mutation. The degradation of Hmg2p-GFP in wild-type HRD1 (RHY513) and mutant hrd1-1 (RHY514) alleles. Each strain was grown into stationary phase for 12 hours after entering mid log phase, and then examined directly by fluorescence microscopy for GFP fluorescence. Top panels (labeled GFP) are GFP fluorescence, bottom panels (labeled DIC) are Nomarsid images of the same group of cells. Although the number of cells in the image is small, the same differences were observed in each of many fields examined.

FIG. 6. Comparison of the Hrd2p sequence and that of TRAP-2/p97, a subunit from the PA700 complex of the 26S proteasome. The HRD2 predicted coding region was compared to the sequence of "p97"/TRAP2. The human gene is on the top row of the first column of the first line, and on the bottom line thereafter. The yeast gene is along the bottom row of the first column of the first line, and on the top line thereafter. The program "ALIGN" was used, at the URL (http: //vega.crbm.cnrs-mop.fr/fasta/align-query.html). The 41% identity represented by the double dots as was spread throughout the sequence of the protein.

Figure 7:
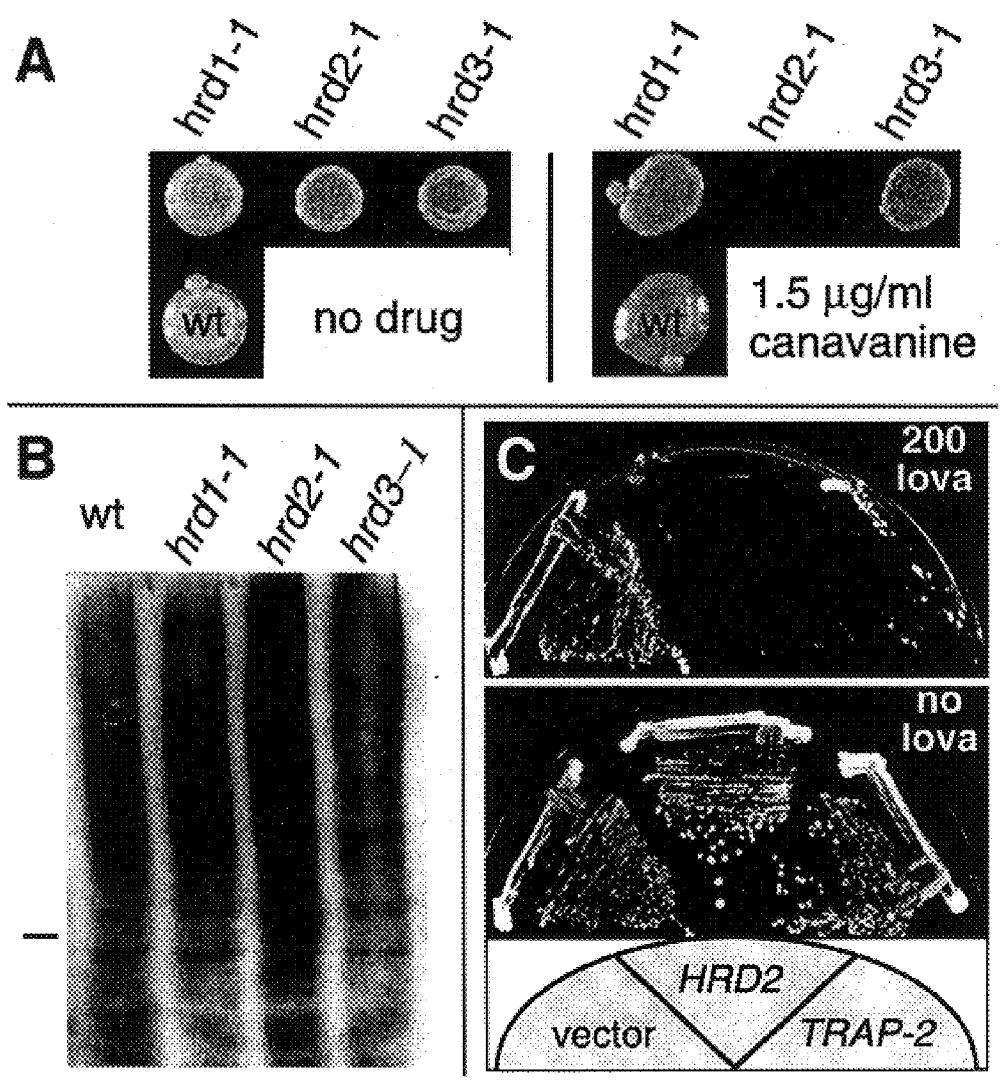

FIG. 7. Proteasomal phenotypes associate with the hrd2-1 mutant. A) Canavanine sensitivity. Liquid cultures of strains with the indicated mutations, but otherwise isogenic, were spotted onto supplemented minimal medium (20 ml of ~0.5 OD) with or without 1.5 μg/ml canavanine as indicated, and allowed to grow at 30° C. for a week. B) Global ubiquitination. Lysates of the same strains were immunoblotted with affinity-purified anti-ubiquitin antibody to survey the degree of ubiquitination of cellular proteins. The line indicates the position of an 80 kD marker. Equal amounts of protein were loaded in each lane and the transfer efficiency from each lane was identical, as judged by India ink staining. The average increase in the amount of ubiquitin conjugates in the hrd2-1 mutant was approximately threefold over the amount in other strains. C) Complementation of the hrd2-1 mutant by the human TRAP-2 coding region. Strain RHY402 (hrd2-1, Ura$^-$) was transformed with parent vector pRH98-1, with a centromere plasmid containing the HRD2 gene (pRH482) or with a plasmid that expressed the TRAP-2 coding region from the GAPDH promoter (pRH492). These transformants are noted "vector, HRD2, and TRAP-2", respectively. Each strain was then streaked on solid medium with 0 (top) or 200 μg/ml (bottom) and allowed to grow at 37° C.

Figure 8:
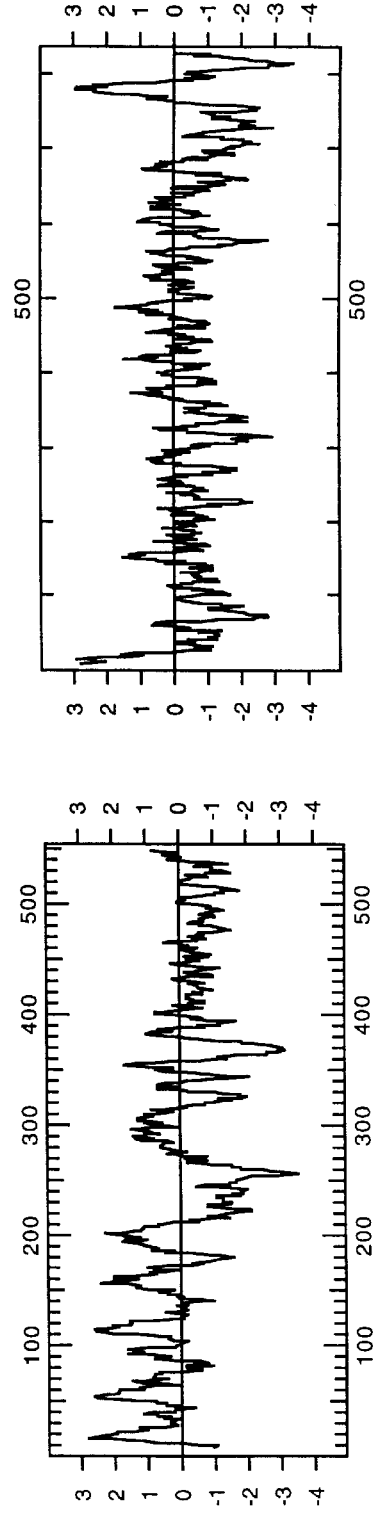

FIG. 8. Sequences and hydropathy plots of the HRD1p and HRD3p predicted proteins. Strongest hydrophobic regions are underlined and in bold face. Only the first two hydrophobic regions are labeled in the Hrd1p protein (left), since these are the only ones with no charged amino acids in the 20 amino acid window. The putative signal sequence of the Hrd3p peptide is also in bold. The plots were generated by the Kyte and Doolittle algorithm using the program DNA Strider.

FIG. 9. A conserved motif in Hrd3p. Alignment of a conserved region of Hrd3p with peptides from Hrd3p itself (top row), the sel-1 protein, the human Ibd2 peptide, and an S. pombe peptide (#1236254). Long arrows indicate those amino acids that were absolutely conserved, and short arrows indicate those that were conserved between the heterologous proteins and the distal region in Hrd3p (row 2).

FIG. 10. This figure illustrates the alignment of two independently isolated EST-encoded peptides from human sources to separate regions of the Hrd3p protein in yeast. (a) Top line is sequence information from EST #T40088 and the bottom is sequence information from the relevant region of the Hrd3p protein; (b) Top line is sequence information from the EST #U11037, and the bottom line is sequence information from the relevant region of the Hrd3p protein.

DEFINITIONS

Unless defined otherwise, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

A "vector" is a composition which can transduce, transfect, transform or infect a cell, thereby causing the cell to replicate or express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell, nor that any particular cell type is the subject of transduction. A cell is "transformed" by a nucleic acid when the nucleic acid is transduced into the cell and stably replicated. A vector includes a nucleic acid (ordinarily RNA or DNA) to be expressed or replicated by the cell. This nucleic acid is optionally referred to as a "vector nucleic acid." A vector optionally includes materials to aid in achieving entry of the nucleic acid into the cell, such as a viral particle, liposome, protein coating or the like. A "cell transduction vector" is a vector which encodes a nucleic acid which is expressed in a cell once the nucleic acid is transduced into the cell.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially a Fab with part of the hinge region (see, *Fundamental Immunology*, Third Edition, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

The term "immunoassay" refers to an assay that utilizes an antibody to specifically bind an analyte. The immunoassay is characterized by the use of specific binding properties of a particular antibody to isolate, target and quantify the analyte.

The term "identical" in the context of two nucleic acid or polypeptide sequences refers to the residues in the two sequences which are the same when aligned for maximum correspondence. When percentage of sequence identity is used in reference to proteins or peptides, it is recognized that residue positions which are not identical often differ by conservative amino acid substitutions, where amino acids residues are substituted for other amino acid residues with similar chemical properties (e.g. charge or hydrophobicity) and, therefore, do not change the functional properties of the molecule. Where sequences differ in conservative substitutions, the percent sequence identity may be adjusted upwards to correct for the conservative nature of the substitution. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (Computer Applic. Biol. Sci., 4: 11–17 (1988)) e.g., as implemented in the program PC/GENE (Intelligenetics, Mountain View, Calif., USA). Nucleic acids which are substantially similar typically encode proteins which are 70% or more similar in their amino acid sequence, or more typically, 80% or more similar, or preferably 90% similar, or most preferably 95% or more similar. Nucleic acids which encode proteins which are 95% or more similar at the amino acid level are substantially identical. Proteins which are 95% identical are also substantially identical. Proteins which are 70% or more similar in their amino acid sequence, or more typically, 80% or more similar, or preferably 90% similar, or most preferably 95% or more similar are substantially similar.

A "comparison window", as used herein, refers to a segment of at least about 50 contiguous positions, usually about 50 to about 200, more usually about 100 to about 150 in which a sequence is compared to a reference sequence of the same number of contiguous positions after the two sequences are optimally aligned.

Homologous amino acid and nucleic acid sequences include natural allelic and interspecies variations in each respective protein sequence. Typical homologous proteins or peptides will have from 50–100% amino acid similarity (if gaps can be introduced) over a comparison window of about 100 amino acids to 75–100% similarity (if conservative substitutions are included) with the amino acid sequence of a particular protein. Similarity measures will typically be at least about 50%, generally at least 60%, more generally at least 65%, usually at least 70%, more usually at least 75%, preferably at least 80%, and more preferably at least 80%, and in particularly preferred embodiments, at least 85% or more. See also, Needleham et al. (1970) *J. Mol. Biol.* 48: 443–453; Sankoff et al. (1983) *Time Warps, String Edits, and Macromolecules: The Theory and Practice of Sequence Comparison* Chapter One, Addison-Wesley, Reading, Mass. Methods of alignment of sequences for comparison are well known in the art. Optimal alignment of sequences for comparison may be conducted by the local homology algorithm of Smith and Waterman (1981) *Adv. Appi. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene*, 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W.H. Freeman and Company.

The terms "isolated" or "biologically pure" refer to material which is substantially or essentially free from components which normally accompany it when found in its native state. The isolated nucleic acids of this invention do not contain materials normally associated with their in situ environment, in particular, nuclear, cytosolic or membrane associated proteins or nucleic acids other than those nucleic acids which are indicated.

The term "labeled nucleic acid probe" refers to a nucleic acid probe that is bound, either covalently, through a linker, or through ionic, van der Waals or hydrogen "bonds" to a label such that the presence of the probe may be detected by detecting the presence of the label bound to the probe.

The term "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin, dioxigenin, or haptens and proteins for which antisera or monoclonal antibodies are available.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence optionally includes the complementary sequence thereof.

The term "recombinant" when used with reference to a cell indicates that the cell replicates or expresses a nucleic acid, or expresses a peptide or protein encoded by nucleic acid whose origin is exogenous to the cell. Recombinant cells can express genes that are not found within the native (non-recombinant) form of the cell.

Recombinant cells can also express genes found in the native form of the cell wherein the genes are re-introduced into the cell by artificial means.

The term "subsequence" in the context of a particular nucleic acid sequence refers to a region of the nucleic acid equal to or smaller than the specified nucleic acid. Similarly, an amino acid subsequence refers to a region of the amino acid equal to or smaller than the specified amino acid.

"Stringent hybridization" and "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology— Hybridization with Nucleic Acid Probes* part I chapter 2

"overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and ph. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4×SSC at 40° C. for 15 minutes. In general, a signal to noise ratio of 2× (or higher) than that observed for an unrelated probe in the particular hybridization assay indicates detection of a specific hybridization.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A "difference" between the rate of HMG-CoA reductase degradation in a first sample versus a second sample refers to a variance in measurable HMG-CoA activity in the first sample versus the second sample. Alternatively, the measured difference can be an immunological indicator for the presence of intact HMG-CoA reductase, such as a western blot or immunological assay. Ordinarily, the variance in activity or presence of intact protein is at least about 5%, generally at least about 10%, commonly at least about 20%, preferably at least about 40%, typically at least about 50%, and often more than 75%.

An "elevated" level of a protein in a yeast strain as compared to a second strain, or wild type yeast strain, refers to a detectable increase in the level of the protein. The increase is measured by monitoring protein levels, e.g., in an ELISA or western blot assay, or by measuring activity of the protein.

DETAILED DESCRIPTION OF THE INVENTION AND PREFERRED EMBODIMENTS

The present invention relates, inter alia, to isolated nucleic acid sequences which encode a family of HMG-CoA Reductase Degradation (HRD) polypeptides. More particularly, the present invention relates to isolated HRD1, HRD2 and HRD3 nucleic acids and to the Hrd polypeptides encoded by such nucleic acids, i.e., Hrd1p, Hrd2p and Hrd3p, respectively. The HRD nucleic acids and the Hrd polypeptides of the present invention have been isolated from yeast and humans. Using the methods of the present invention, such HRD nucleic acids and Hrd polypeptides can be readily isolated from other eukaryotic sources. Moreover, using the methods of the present invention, other members of the HRD family can be identified.

It has been discovered that the Hrd polypeptides of the present invention regulate the degradation of HMG-CoA reductase, the enzyme which catalyzes the rate-limiting reaction in the pathway of cholesterol biosynthesis. Without being bound to any given theory, it is thought that the Hrd polypeptides of the present invention are structural or adaptor proteins which assist in bringing the proteasome complex, i.e., the machinery responsible for degradation, to the HMG-CoA reductase. As such, the Hrd polypeptides of the present invention can be used to regulate the degradation of HMG-CoA reductase. Moreover, the Hrd polypeptides of the present invention can be used in various assays to identify other compounds which can be used to modify the degradation of HMG-CoA reductase.

The HRD nucleic acids and Hrd polypeptides of the present invention were identified by taking advantage of a deep similarity in the control of HMG-CoA reductase stability between eukaryotes and the genetically tractable yeast, *S. cerevisiae*. It has been found that one of the two isozymes of yeast HMG-CoA reductase, i.e., Hmg2p, is subject to regulated degradation in a manner that is strikingly similar to that observed in mammalian cells. Like its mammalian counterpart, the Hmg2p protein is retained in the endoplasmic reticulum (ER), where it is degraded with a half-life on the order of 30 minutes to 1 hour. Moreover, the degradation of Hmg2p is controlled by the mevalonate pathway in a manner which is substantially identical to the control of HMG-CoA reductase stability in mammals, i.e., when flux through the pathway is high, the degradation rate is fast; whereas, when flux through the pathway is slowed either by drugs or genetic means, the degradation rate is slowed, such that the half-life extends to well beyond 6 hours. In addition, as is the case in eukaryotic cells, a molecular signal for the stimulated degradation of HMG-CoA reductase lies upstream of squalene in the mevalonate pathway. These observations have led to a genetic investigation of the molecules that mediate the regulated degradation of HMG-CoA reductase in yeast, with the expectation that homologous proteins mediate the analogous processes in other eukaryotic cells.

In order to discover the molecules that mediate the degradation of HMG-CoA reductase in yeast, the results of basic research have been harnessed to establish a powerful genetic screen. It has been found that the HMG2 gene can be altered to express a variant of Hmg2p that is still degraded, but whose stability is no longer regulated by changes in the mevalonate pathway. A strain expressing this gene as the sole source of HMG-CoA reductase activity was used as a parent strain to obtain mutants that are deficient in the degradation of the variant Hmg2p. The drug lovastatin, a competitive inhibitor of HMG-R, was used as a selection tool. Since HMG-CoA reductase activity is essential for the survival of eukaryotic cells, lovastatin kills yeast cells in a dose-dependent fashion. The dose of lovastatin that is required to kill the cells is determined by the steady-state level of HMG-CoA reductase present, i.e., the more HMG-CoA reductase that is present, the more lovastatin it takes to kill the cells. Thus, one way to survive a lovastatin insult is to slow the degradation of HMG-CoA reductase in order to build up a higher steady-state amount of HMG-CoA reductase. In the strain expressing the unregulated variant of the Hmg2p protein, lovastatin has no secondary effects on the stability of the protein through the slowing of the mevalonate pathway and, thus, the only way to slow degradation of the HMG-CoA reductase is to have a pre-existing mutation in the degradation process. By use of this strain, the physiological regulation of HMG-CoA reductase degradation is sufficiently impaired to allow efficient recovery of mutants selected from the parent strain without mutagenesis. In this manner, a collection of mutants that are deficient for the degradation of HMG-CoA reductase have been collected and additional mutants can be collected using the same strategy.

Using these mutants, three independent, recessive complementation groups for the HRD nucleic acids were identified in yeast. All hrd mutants so far isolated also stabilize authentic Hmg2p, indicating that the HRD selection using the engineered strain offers a facile method to locate all of the genes in the HMG-CoA reductase degradation pathway. By cloning and sequencing the HRD nucleic acids, the sequences of the polypeptides which mediate the degradation of HMG-CoA reductase in yeast were identified. In doing so, it was determined that the yeast HRD2 nucleic acid which corresponds to SEQ ID NO:1, encodes a soluble polypeptide (Hrd2p) having a molecular weight of about 109 kD and the amino acid sequence corresponding to SEQ ID NO:3. In contrast, the yeast HRD3 nucleic acid, which corresponds to SEQ ID NO:2, encodes a type I membrane polypeptide (i.e., the N-terminus is in the cytosol) having a molecular weight of about 99 kD with a single membrane spanning sequence. The polypeptide is termed Hrd3p. The amino acid sequence of the polypeptide encoded by HRD3 is set forth in SEQ ID NO:4. HRD1, which corresponds to SEQ ID NO:7 was isolated as described in the Example Section herein. A Hrd1p polypeptide is represented in FIG. 8.

Using the amino acid sequences of the yeast Hrd polypeptides, nucleic acids have been identified which encode the corresponding homologous proteins in mammals. As with yeast, three independent HRD nucleic acids have been identified in humans. In one embodiment, identification of the HRD nucleic acids was carried out by comparing the HRD coding regions with the now-extensive collection of public and private databases of deposited sequences which are derived from collections of random, expressed messenger RNAs, known as Expressed Sequence Tags (ESTs), as well as whole messenger RNA sequences that are generally deposited in databases without any knowledge of function. By doing such searches, it is clear that HRD2 and HRD3 have corresponding homologous polypeptides in the human genome. Searches with the yeast Hrd2p coding region have located a coding region in the public database that encodes a putative protein of 67 kD. This protein was entered in the database as the coding region from a liver cell line-specific transcript (Accession #U18247). Subsequent searches revealed that the actual human homologue is significantly longer than the 67 kD that is indicated from this deposit. In addition, an independent EST (GenBank accession #R55175) with a coding region homologous to the Hrd2p protein and a 102 kD protein, called TRAP-2 (accession number U12596; Song, et al., *J. Biol. Chem.* 270:3574–3581 (1995)), both demonstrate that, as with the yeast Hrdp2 polypeptide, the human Hrd2p polypeptide has a molecular weight of about 102 kD. It is apparent that all three of these separate sequences are from either the same gene in the human genome, or a very closely related group, since all share large regions of identity at the nucleotide level. Most likely, the coding region of the p67 protein has a mis-assigned start site that is actually part of the internal coding region of the TRAP-2 coding region. The alignment between the yeast and human Hrd2p polypeptides is shown in FIG. 6. The extent of sequence similarity between the two sequences indicates that the human Hrd2p polypeptide is involved in the degradation of human HMG-CoA reductase and potentially other membrane proteins as well.

Moreover, it has been determined that the yeast Hrd3p polypeptide, corresponding to SEQ ID NO:4, has a human counterpart. Two independent cDNA sequences from deposited ESTs were identified by searches using the Hrd3p coding region. One EST (Accession #U11037), corresponding to SEQ ID NO:5 is homologous to a portion of the Hrd3p coding region, i.e., the region spanning from amino acid 690 to amino acid 754. In addition, the other EST (Accession #T40088), corresponding to SEQ ID NO:6, is homologous to a portion of Hrd3p defined by amino acids 178–262. SEQ ID NO:8, termed Ibd2, and FIG. 10 also represent Hrd3p homologues. As a result of the sequence similarity between the yeast Hrd3p polypeptide and these ESTs, it is apparent that the Hrd3 polypeptide has a representative in the human genome as well. See, FIG. 10.

Using the methodology set forth herein, one of skill can readily produce the Hrd polypeptides of the present invention. In general, the DNA encoding the Hrd polypeptides are first cloned or isolated in a form suitable for ligation into an expression vector. After ligation, the vector containing the DNA fragments or inserts are introduced into a suitable host cell for expression of the recombinant Hrd polypeptides. The Hrd polypeptides are then isolated from the host cell. Once produced, the Hrd polypeptides of the present invention can be used to regulate the degradation of HMG-CoA reductase. Moreover, the Hrd polypeptides of the present invention can be used to elucidate, in mechanistic terms, how the cholesterol pathway modulates the degradation of HMG-CoA reductase. In addition, as a result of their ability to bind the proteasome complex, antibodies which specifically bind the HRD polypeptides can be used to isolate the proteasome complex. Further, the Hrd polypeptides of the present invention can be used in various assays to identify other compounds having the ability to modify the degradation of HMG-CoA reductase in a manner that is independent of the beneficial LDL receptor control axis.

In addition to its role in cholesterol metabolism, it is clear that the ER protein degradation pathway is involved in numerous other clinically important processes, including, for example, immune receptor assembly, drug metabolism, cystic fibrosis and HIV biogenesis. These processes are interconnected as a result of the fact that in each instance key proteins are degraded by the ER pathway. As such, the Hrd proteins, which are involved in the general process of ER protein degradation, have useful mechanistic roles in these and other pathophysiological conditions. In several cases (e.g., HIV biogenesis, cystic fibrosis), inhibition of ER degradation events associated with these processes has been suggested as a possible avenue of therapeutic intervention. Thus, the Hrd polypeptides of the present invention can be used to identify compounds having the ability to inhibit the ER degradation events associated with such processes.

Making HRD Nucleic Acids and Vectors

The vectors of the invention include a vector nucleic acid, and optionally include components for packaging the vector nucleic acid to facilitate entry of the nucleic acid into a cell. The vector nucleic acid includes a nucleic acid subsequence which encodes a nucleic acid or protein of the invention. The subsequence is typically cloned into a cloning site in the vector nucleic acid which is designed to facilitate recombinant manipulation. A variety of commercially or commonly available vectors and vector nucleic acids can be converted into a vector of the invention by cloning a nucleic acid encoding a protein of the invention into the commercially or commonly available vector. A variety of common vectors suitable for this purpose are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of plasmids, including pSV2, pBC12BI, and p91023, as well as lytic virus vectors (e.g., vaccinia virus, adeno virus, and bacculovirus), episomal virus vectors (e.g., bovine papillomavirus), and retroviral vectors (e.g., murine retroviruses).

Nucleic acid subsequences encoding selected polypeptides are placed under the control of a promoter. A extremely wide variety of promoters are well known, and can be used in the vectors of the invention, depending on the particular application. Ordinarily, the promoter selected depends upon the cell in which the promoter is to be active. Other expression control sequences such as ribosome binding sites, transcription termination sites, and the like are optionally included. For *E. coli*, example control sequences include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440–1448) ADH2 (Russell et al. (1983) *J. Biol. Chem.* 258:2674–2682), PH05 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids such as YEp6, YEp13, YEp4 can be used as expression vectors. A gene of interest can be fused, e.g., to any of the promoters in known yeast vectors. The above-mentioned plasmids have been fully described in the literature (Botstein et al. (1979) *Gene* 8:17–24; Broach, et al. (1979) *Gene,* 8:121–133). For a discussion of yeast expression plasmids, see, e.g., Parents, B., *YEAST* (1985), and Ausbel, Sambrook and Berger, all supra).

The present invention provides a variety of HRD nucleic acids, including the sequences provided herein, subclones of the sequences, PCR primers based upon the sequences, and molecular probes. All of these nucleic acids are optionally encoded by a vector. These nucleic acids are useful, inter alia, in the expression of the corresponding encoded polypeptides, as in situ probes to monitor expression of the corresponding genes, and as diagnostic markers for the presence of the corresponding nucleic acid in a biological sample.

Given the sequence of a nucleic acid of the present invention, such as HRD2p or HRD3p, one of skill can construct a variety of clones containing derivative sequences and subsequences. Cloning methodologies to accomplish these ends and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

The nucleic acid compositions of this invention, whether RNA, cDNA, genomic DNA, or a hybrid of the various combinations, are isolated from natural sources or synthesized in vitro. The nucleic acids claimed are present in transformed or transfected whole cells (eukaryotic or prokaryotic), in transformed or transfected cell lysates, or in a partially purified or substantially pure form.

In vitro amplification techniques are suitable for amplifying sequences, e.g., for use as molecular probes or for generating proviral nucleic acid fragments for subsequent subcloning. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as probes, e.g., in in vitro amplification methods, or for use as gene probes are typically synthesized chemically according to the solid phase phosphoramidite triester method described by Beaucage and Caruthers (1981), *Tetrahedron Letts.,* 22(20):1859–1862, e.g., using an automated synthesizer, as described in Needham-VanDevanter et al. (1984) *Nucleic Acids Res.,* 12:6159–6168. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

The polypeptides of the invention can be synthetically prepared in a wide variety of well-know ways. For instance, polypeptides of relatively short size can be synthesized in solution or on a solid support in accordance with conventional techniques. See, e.g., Merrifield (1963) *J. Am. Chem. Soc.* 85:2149–2154. Various automatic synthesizers are commercially available and can be used in accordance with known protocols. See, e.g., Stewart and Young (1984) *Solid Phase Peptide Synthesis*, 2d. ed., Pierce Chemical Co.

PCR Screening to Isolate HRD Homologues

From the extreme conservation of HMG-CoA reductase regulation, it is apparent that the yeast HRD genes have homologues throughout the eukaryotes. As described supra, probes can be designed from yeast HRD nucleic acid sequences, taking species codon bias into account, to isolate corresponding homologous genes from other species. In one embodiment, PCR primers are constructed for the isolation of HRD homologues from species other than yeast. For example, the following four primer pair sequences are designed to PCR amplify an approximately 260 base pair portion of the TRAP-2 gene specifically from human cDNA libraries, the HRD2 gene from *Saccharomyces cerevisae*, a degenerate oligonucleotide primer pair which amplifies both Trap-2 and HRD2, and a hybrid pair designed to preferentially amplify mammalian HRD2 homologs, respectively. The first four primer sequences listed amplify from the 5' to the 3' direction with respect to the structure of the gene; the last four primer sequences amplify from the 3' to the 5' direction. All sequences are written in the 5' to 3' direction.

5'

TRAP-2
  GCT GTT CTG GGG ATT GCC CTT ATT GC (SEQ ID NO:13)

HRD2
  GCA GTT TTG GGT ATT GCT TTG ATT GC (SEQ ID NO:14)

Degenerate:
  GCN GTT C/TTG GGN ATT GCN C/TTN ATT GC

Hybrid:
  GCT GTT CTG GGT ATT GCC TTT ATT GC (SEQ ID NO:15)

3'

TRAP-2
  AGC CAG ACG GGC ATT ATT GGT ACC A (SEQ ID NO:16)

HRD2
  AGC TAA CCT TGC ATT GTT AGT ACC A (SEQ ID NO:17)

Degenerate
  AGC T/CAN A/CCN G/TGC ATT A/GTT A/GGT ACC A (SEQ ID NO:18)

Hybrid
  AGC CAA CCG TGC ATT GTT GGT ACC A (SEQ ID NO:19)

Making Conservative Modifications to the Nucleic Acids and Polypeptides of the Invention One of skill will appreciate that many conservative variations of the nucleic acid and amino acid sequences disclosed herein yield a functionally similar or identical nucleic acid or polypeptide. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook, Innis, Ausbel, Berger, Needham VanDevanter and Mullis (all supra).

Most commonly, polypeptide sequences are altered by altering the corresponding nucleic acid sequence and expressing the polypeptide. However, polypeptide sequences are also optionally generated synthetically on commercially available peptide synthesizers to produce any desired polypeptide (see, Merrifield, and Stewart and Young, supra).

One of skill can select a desired nucleic acid or polypeptide of the invention based upon the sequences provided and upon knowledge in the art regarding nucleic acids and proteins generally. The general effects of many mutations are known. General knowledge regarding the nature of proteins and nucleic acids allows one of skill to select appropriate sequences with activity similar or equivalent to the nucleic acids and polypeptides disclosed in the sequence listings herein. The definitions section, supra, describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques.

Cloning by Complementation and Trans-Complementation

The general strategy for isolating genes by complementation in yeast is described, e.g., in Berger and Kimmel (supra), chapter 53 "Isolation of genes by complementation in Yeast" by Rose, and the references described therein. Cloning by complementation is described by Reed and Nasmyth, (1980) *PNAS, USA* 77(4):2119–2123. *Saccharomyces cerevisiae* has a genome of about 15, 000 kb. Therefore, large recombinant DNA libraries with inserts averaging 15 kb in size have each given fragment represented at a frequency of about 1 in 1,000. *Saccharomyces cerevisiae* are easily transformed using a variety of techniques, such as by preparation of spheroplasts, or by treatment with alkaline salts. Typically, DNA is integrated into the yeast chromosome by homologous recombination, or maintained as an episomal plasmid.

A common way of cloning genes in yeast is by using the ability of a clone to complement a mutant gene by providing the function of the gene in trans. Thus, mutant yeast are transformed with a wild-type library of clones, plated, and monitored for the restoration of wild-type function to particular yeast clones. For instance, in one embodiment, mutant yeast with lovastatin (or other HMG-CoA reductase inhibitor) resistance are transformed, plated in duplicate, and one of the duplicate plates is selected on lovastatin, or another HMG-CoA reductase inhibitor. Clones which are killed or whose growth is inhibited by the lovastatin are transformed with the wild-type gene, and selected from the duplicate plate. The nucleic acid is then isolated as appropriate, depending on the construction of the library vector used to transform the yeast. For instance, the clones typically include restriction sites or molecular tags to facilitate subcloning.

Thus, in one embodiment, the present invention provides a method for isolating genes which regulate HMG-CoA reductase degradation. In this method, a yeast strain which exhibits a non-mevalonate dependent HMG-CoA reductase phenotype (see, supra for a description of how to make an artificial HMG-CoA reductase gene which is not regulated by flux through the mevalonate pathway) is selected for resistance to an HMG-CoA reductase inhibitor, such as lovastatin, pravastatin or simvastatin, to isolate mutants which do not degrade HMG-COA reductase as rapidly as wild-type yeast. The mutants are then screened against a yeast library to isolate genes which restore the wild-type phenotype by trans complementation. The resulting clones are then isolated and characterized by standard techniques.

Use of The Nucleic Acids of The Invention as Molecular Probes

The nucleic acids of the invention, whether present in a vector or expressed from a vector, are useful as molecular probes, in addition to their utility in encoding the polypeptides described herein. For instance, the presence of yeast in a biological sample can be detected by monitoring the presence of the HRD nucleic acids of the invention. This is useful, for example, in assessing the purity of reagents, foods, cell cultures or other samples. For instance, yeast are a major contaminant for many mammalian and insect cell and tissue cultures, often causing the death of a particular cell culture. Thus, the ability to detect yeast is of commercial importance.

The nucleic acids of the invention are also useful as molecular probes for the isolation of homologous nucleic acids. For instance, the nucleic acids of the invention are useful for the isolation of allelic, species and strain variants of each nucleic acid. In addition, as demonstrated supra, the HRD nucleic acids are part of a fundamental biodegradative pathway, which is responsible for the regulation of cholesterol synthesis by modification of HMG-CoA reductase activity. As demonstrated herein, species as diverse as humans and yeast share homologous HRD genes. Accordingly, HRD genes of the present invention can be used to isolate homologous genes from all eukaryotes, including mammals, and, in particular, humans. Typically, a known HRD probe is optimized for probing for homologous genes by using conserved regions in the protein as probes, and by synthesizing probes taking into account species codon bias. Species codon bias tables are available to persons of skill, showing the relative frequency with which a particular species makes use of a particular codon coding for a particular amino acid. By converting all of the codons in a nucleic acid probe into the most common codons used by the particular species to be probed, the similarity of the probe to the species homologue is increased.

A wide variety of formats and labels are available and appropriate for nucleic acid hybridization, including those reviewed in Tijssen (1993) *Laboratory Techniques in biochemistry and molecular biology—hybridization with nucleic acid probes* parts I and II, Elsevier, N.Y. and Choo (ed) (1994) *Methods In Molecular Biology* Volume 33—*In Situ Hybridization Protocols* Humana Press Inc., N.J. (see also, other books in the Methods in Molecular Biology series); see especially, Chapter 21 of Choo (id) "Detection of Virus Nucleic Acids by Radioactive and Nonisotropic in Situ Hybridization".

For instance, PCR is routinely used to detect nucleic acids in biological samples (see, Innis, supra, for a general description of PCR techniques). Accordingly, in one class of embodiments, the nucleic acids of the invention are used as PCR primers, or as positive controls in PCR reactions for the detection of a HRD nucleic acid in a biological sample such as a yeast culture, or where the HRD nucleic acid is a human homologue, for detection of HRD nucleic acids in, e.g., human blood. Briefly, nucleic acids encoded by the nucleic acid constructs of the invention are used as templates to synthetically produce oligonucleotides of about 20–100 nucleotides with sequences similar or identical to the selected nucleic acid. The oligonucleotides are then used as primers in PCR reactions to detect the corresponding nucleic acids in biological samples. The nucleic acids of the invention (i.e., a nucleic acid corresponding to the region to be amplified) are also used as amplification templates in separate reactions to determine that the PCR reagents and hybridization conditions are appropriate.

Other methods for the detection of HRD nucleic acids in biological samples using nucleic acids of the invention include Southern blots, northern blots, in situ hybridization (including Fluorescent in situ hybridization (FISH), reverse chromosome painting, FISH on DAPI stained chromosomes, generation of Alphoid DNA probes for FISH using PCR, PRINS labeling of DNA, free chromatin mapping and a variety of other techniques described in Choo (supra)). A variety of automated solid-phase detection techniques are also appropriate. See, Tijssen (supra), Fodor et al. (1991) *Science,* 251: 767–777 and Sheldon et al. (1993) *Clinical Chemistry* 39(4): 718–719.

Expression of Hrd Polypeptides

Once a HRD nucleic acid or subsequence nucleic acid is isolated and cloned into a vector, one may express the nucleic acid in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for cloning and expression of HRD nucleic acids.

In brief summary, the expression of natural or synthetic nucleic acids encoding, e.g., a Hrd2, a Hrd3, or a Hrd1 polypeptide is typically achieved by operably linking a nucleic acid encoding the polypeptide of interest to a promoter (which is either constitutive or inducible), and incorporating the construct into an expression vector. The vectors can be suitable for replication and integration in prokaryotes, eukaryotes, or both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

To obtain high levels of expression of a cloned nucleic acid, it is common to construct expression plasmids which typically contain a strong promoter to direct transcription, a ribosome binding site for translational initiation, and a transcription/translation terminator. For example, as described herein, the polypeptides encoded by the nucleic acids of the present invention, which are useful as antigenic reagents and as components of diagnostic and drug screening assays, are optionally expressed in bacterial cells such as *E. coli*. Examples of regulatory regions suitable for this purpose in *E. coil* are the promoter and operator region of the *E. coli* tryptophan biosynthetic pathway as described by Yanofsky, C., 1984, *J. Bacteriol.*, 158:1018–1024, and the leftward promoter of phage lambda ($P_L$) as described by Herskowitz and Hagen, 1980, *Ann. Rev. Genet.*, 14:399–445. The inclusion of selection markers in DNA vectors transformed in bacteria such as *E. coli* is also useful. Examples of such markers include genes specifying resistance to ampicillin, tetracycline, or chloramphenicol. See, Sambrook, Ausbel, and Berger for details concerning selection markers, e.g., for use in *E. coli*. Expression systems for expressing polypeptides are available using *E. coli, Bacillus sp.* (Palva, I. et al., 1983, *Gene* 22:229–235; Mosbach, K. et al., *Nature,* 302:543–545) and *Salmonella. E. coli* systems are the most common, and best defined expression systems and are, therefore, preferred.

Polypeptides produced by prokaryotic cells often require exposure to chaotropic agents for proper folding. During purification from, e.g., *E. coli*, the expressed protein is optionally denatured and then renatured. This is accomplished, e.g., by solubilizing the bacterially produced antibodies in a chaotropic agent such as guanidine HCl. The antibody is then renatured, either by slow dialysis or by gel filtration. See, U.S. Pat. No. 4,511,503.

Methods of transfecting and expressing genes in eukaryotic cells are also known in the art. For example, synthesis of heterologous proteins in yeast is well known and described. See, e.g., Sherman et al. (1982) *Methods in Yeast Genetics*, Cold Spring Harbor Laboratory. Examples of promoters for use in yeast include GAL1,10 (Johnson and Davies (1984) *Mol. Cell. Biol.* 4:1440–1448) ADH2 (Russell et al. (1983) *J. Biol. Chem.* 258:2674–2682), PH05 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids like YEp6, YEp13, YEp4 can be used as expression vectors. A gene of interest can be fused to any of the promoters in various yeast vectors. The above-mentioned plasmids have been fully described in the literature (Botstein et al. (1979) *Gene* 8:17–24; Broach, et al. (1979) *Gene*, 8:121–133). For a discussion of yeast expression plasmids, see, e.g., Parents, B., *YEAST* (1985)).

Two procedures are commonly used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen, et al. (1978) *Proc. Natl. Acad. Sci. USA* 75:1929–1933. The second procedure does not involve removal of the cell wall. Instead, the cells are treated, e.g., with lithium chloride or acetate and PEG and put on selective plates (Ito, et al. (1983) *J. Bact.* 153:163–168).

The polypeptides of interest are isolated from yeast by lysing the cells and applying standard protein isolation techniques to the lysates. The polypeptides of this invention are purified to substantial purity by standard techniques well known in the art, including selective precipitation with such substances as ammonium sulfate, column chromatography, immunopurification methods, and others. See, for instance, Scopes (1982) *Protein Purification: Principles and Practice* Springer-Verlag New York. The monitoring of the purification process is accomplished by using Western blot techniques, radioimmunoassays or other standard immunoassay techniques, or by monitoring the protein directly, e.g., by coomassie blue or silver-stain polyacrylamide gel electrophoresis.

Transducing cells with nucleic acids can involve, for example, incubating viral vectors containing nucleic acids which encode polypeptides of interest with cells within the host range of the vector. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990) and the references cited therein. The culture of cells used in conjunction with the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells.

Illustrative of cell cultures useful for the production of polypeptides are cells of insect or mammalian origin. Mammalian cell systems often will be in the form of monolayers of cells, although mammalian cell suspensions are also used. Illustrative examples of mammalian cell lines include VERO and HeLa cells, Chinese hamster ovary (CHO) cell lines, W138, BHK, Cos-7 or MDCK cell lines (see, e.g., Freshney, supra).

As indicated above, the vector, e.g., a plasmid, which is used to transform the host cell, preferably contains nucleic acid sequences to initiate transcription and sequences to control the translation of the encoded polypeptide. These sequences are referred to generally as expression control sequences. When the host cell is of insect or mammalian origin, illustrative expression control sequences are obtained from the SV-40 promoter (*Science* (1983) 222:524–527), the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for the polypeptide of interest by means well known in the art.

As with yeast, when higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781).

Additionally, gene sequences to control replication in a particular host cell are incorporated into the vector, such as those found in bovine papilloma virus type-vectors. See, Saveria-Campo (1985), "Bovine Papilloma virus DNA a Eukaryotic Cloning Vector" in *DNA Cloning* Vol. II *a Practical Approach* Glover (ed) IRL Press, Arlington, Va. pp. 213–238.

Host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation and micro-injection of the DNA directly into the cells.

Transformed cells are cultured by means well known in the art. See, Freshny (supra), Kuchler et al. (1977) *Biochemical Methods in Cell Culture and Virology*, Kuchler, R. J., Dowden, Hutchinson and Ross, Inc. The expressed polypeptides are isolated from cells grown as suspensions or as monolayers. The latter are recovered by well known mechanical, chemical or enzymatic means. See, Scopes, supra.

Making Antibodies to Hrd Polypeptides and to HMG-CoA Reductase

Hrd polypeptides are optionally bound by antibodies in one class of embodiments of the present invention. The polypeptides are used as diagnostic reagents as described herein, or as immunogens for the production of antibodies which are also useful, e.g., as diagnostic reagents. In addition, the discovery presented herein that Hrd2p is the yeast homologue of the human TRAP-2 gene (see, GenBank™ accession numbers U12596 SEQ ID NO:9) and d78151) SEQ ID NO:11) provides one of skill with several additional uses for Hrd2p. It is known that TRAP-2 is associated with the protosome, a piece of the cellular machinery for degrading cytosolic proteins. From the discovery presented herein that Hrd2p regulates HMG-CoA reductase degradation, it is apparent that Hrd2p also interacts with the proteasome, and that the proteasome is responsible for degradation of proteins in the endoplasmic reticulum, such as HMG-CoA reductase. Accordingly, isolation of the proteasome is of commercial importance as an in vitro reagent for screening compounds which modulate HMG-CoA reductase inhibition. Antibodies to Hrd2p are used to isolate the proteasome by binding Hrd2p (which binds the proteasome).

The antibodies of this invention can also be used for affinity chromatography in isolating Hrd polypeptides generally. Columns can be prepared, e.g., with the antibodies linked to a solid support, e.g., particles, such as agarose, Sephadex, or the like, where a cell lysate is passed through the column, washed, and treated with increasing concentrations of a mild denaturant, whereby purified polypeptides are released.

The antibodies are used, e.g., to screen expression libraries for particular expression products such as mammalian Hrd proteins. Usually, the antibodies in such a procedure will be labeled with a moiety allowing easy detection of presence of antigen by antibody binding, or be amenable to simplified labeling using anti-species antibody labels.

Antibodies raised against Hrd polypeptides can be used to raise antiidiotypic antibodies. These are useful for detecting or diagnosing various pathological conditions related to the presence of the respective antigens.

Antibodies to Hrd polypeptides can also be used to regulate Hrd activity in vivo. By binding to Hrd proteins in vivo, antibodies can block the activity of Hrd proteins. Blocking the activity of Hrd proteins increases the level of HMGCoA reductase, thereby increasing the amount of cholesterol synthesized by a cell. This is useful in the treatment of hypocholosterolemia.

HMG-CoA reductase degradation is typically measured by western blotting or other immunoblotting or immuno detection techniques as described herein, using an antibody which binds HMG-CoA reductase, or an epitope tagged version of the enzyme. Dot-blotting of crude cellular extracts or reaction mixes, or proteins separated on PAGE gels are two preferred embodiments for quantitating HMG Co-A reductase in a biological sample. The immunoprecipitation techniques and assays described below are also suitable for HMG Co-A reductase quantitation.

Methods of producing polyclonal and monoclonal antibodies are known to those of skill in the art. See, e.g., Coligan (1991) *Current Protocols in Immunology* Wiley/Greene, NY; and Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

Frequently, the polypeptides and their corresponding antibodies will be labeled by joining, either covalently or non covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The immunogenic compositions of this invention (e.g., peptides, nucleic acids, viral particles which include the peptides or nucleic acids of the invention, etc.) are also used for affinity chromatography in isolating and quantitating Hrd antibodies and anti-sera. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified antibodies are released.

Immunoassay Formats

Hrd proteins, anti-Hrd protein antibodies, and the HMG CoA reductase enzyme can all be quantified in a biological sample by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, N.Y.

Immunoassays often utilize a labeling agent to specifically bind to and label the binding complex formed by the capture agent and the analyte (the Hrd polypeptides of the invention are either the capture agent, or the analyte, depending on the format of the assay; i.e., they are used to capture and detect an antibody, or are themselves captured and detected by an antibody). The labeling agent may itself be one of the moieties comprising the capture agent/analyte complex. Thus, the labeling agent is optionally a labeled polypeptide or a labeled antibody. Alternatively, the labeling agent is optionally a third moiety, such as another antibody, that specifically binds to the capture agent/polypeptide complex, or to a modified capture group (e.g., biotin) which is covalently linked to the peptide or antibody.

In one embodiment, the labeling agent is an antibody that specifically binds to the capture agent, which is a Hrd polypeptide. Such labeling agents are well known to those of skill in the art, and most typically comprise labeled antibodies that specifically bind antibodies of the particular animal species from which the capture agent is derived (e.g., an anti-species antibody). Thus, for example, where the capture agent is a mouse antibody, the labeling agent may be a goat anti-mouse IgG, i.e., an antibody specific to the constant region of the mouse antibodies.

Other proteins capable of specifically binding immunoglobulin constant regions, such as streptococcal protein A or protein G are also useful as labeling agents. These proteins are normal constituents of the cell walls of streptococcal bacteria. They exhibit a strong non-immunogenic reactivity with immunoglobulin constant regions from a variety of species. See, generally Kronval, et al., (1973) *J. Immunol.*, 111:1401–1406, and Akerstrom, et al., (1985) *J. Immunol.*, 135:2589–2542.

Alternatively, polypeptide can be labeled directly, e.g., by producing the polypeptide in a cell culture containing radioactive amino acids, or by radiolabeling purified polypeptides.

In another embodiment, the capture agent is a polypeptide and the analyte is an antibody. In this embodiment, the polypeptide is typically labeled directly (e.g., by radiolabeling with radioactive isotopes), or by using an antibody label distinct from the analyte antibody.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentration of capture agent and analyte, and the like. Usually, the assays are carried out at ambient temperature, although they can be conducted over a range of temperatures, such as 5° C. to 45° C.

Noncompetitive Assay Formats

Immunoassays for detecting a polypeptide or antibody may be either competitive or noncompetitive. Noncompetitive immunoassays are assays in which the amount of captured analyte is directly measured. In one preferred "sandwich" assay, for example, the capture agent is bound directly to a solid substrate where it is immobilized. These immobilized capture agents then "capture" or "bind" the analyte present in a test sample. The analyte thus immobilized is then bound by a labeling agent, such as an antibody bearing a label. Alternatively, the labeling agent may lack a direct label, but it may, in turn, be bound by a labeled third moiety, such as an antibody specific to antibodies of the species from which the labeling agent is derived.

Sandwich assays for an analyte are optionally constructed. As described above, the immobilized capture agent specifically binds to the analyte in the sample. The labeled anti-analyte (labeling agent) then binds to the capture agent-analyte complex. Free labeling agent is washed away and the remaining bound labeled complex is detected (e.g., using a gamma detector where the label is radioactive).

Competitive Assay Formats

In competitive assays, the amount of analyte present in the test sample is measured indirectly by measuring the amount of an added (exogenous) analyte displaced (or competed away) from a capture agent by the analyte present in the sample. In one competitive assay, a known amount of analyte is added to the sample and the sample is contacted with a capture agent that specifically binds the analyte. The amount of analyte bound to the capture agent is inversely proportional to the concentration of analyte present in the sample.

In a preferred embodiment, the capture agent is immobilized on a solid substrate. The amount of analyte bound to the capture agent is determined either by measuring the amount of analyte present in an analyte-capture agent complex, or alternatively by measuring the amount of remaining uncomplexed analyte. The amount of analyte in a sample to be assayed may also be detected by providing exogenous labeled analyte to the assay.

A hapten inhibition assay is another preferred competitive assay. In this assay, a known analyte is immobilized on a solid substrate. A known amount of anti-analyte is added to the sample, and the sample is then contacted with the capture agent. In this case, the amount of anti-analyte bound to the immobilized capture agent is proportional to the amount of analyte present in the sample. Again, the amount of immobilized analyte is detected by quantitating either the immobilized fraction of anti-analyte or the fraction of the anti-analyte that remains in solution. Detection is direct where the anti-analyte is labeled, or indirect where a labeled moiety is subsequently added which specifically binds to the anti-analyte as described above.

Cross-reactivity Determinations

Whether a protein specifically binds to, or is specifically immunoreactive with an antibody generated against a defined immunogen, such as an immunogen consisting of the amino acid sequence of SEQ ID NO: 3 or SEQ ID NO: 4 or those described in FIG. 8 (e.g., Hrd1p, Hrd2p and Hrd3p polypeptides), is determined in an immunoassay. The immunoassay uses a polyclonal antiserum which is raised to the immunogen of choice. This antiserum is selected to have low cross-reactivity against other yeast components and any such cross-reactivity is removed by immunoabsorbtion prior to use in the immunoassay.

In order to produce antisera for use in an immunoassay, the immunogen is isolated as described herein. For example, recombinant protein may be produced in a bacterial or yeast cell line. An inbred strain of mice such as balb/c is immunized with the immunogen using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and their cross reactivity tested, using a competitive binding immunoassay such as the one described in Harlow and Lane, supra, at pages 570–573.

Immunoassays in the competitive binding format are used for cross-reactivity determinations. For example, in one embodiment the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent cross-reactivity for the above proteins is calculated, using standard calculations. Those antisera with less than 10% cross-reactivity with the particular Hrd protein (e.g., Hrd3p) are selected and pooled. The cross-reacting antibodies are then removed from the pooled antisera by immunoabsorbtion with isolated yeast proteins which were previously immusorbed with an antibody to the immunogen being tested, or by immusorbtion with well-known general immusorbtive materials for elimination of non-specific binding, such as 5% powdered milk, BSA and the like.

The immunoabsorbed and pooled antisera are then used in a competitive binding immunoassay, as described herein, to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein. If a test peptide is specifically bound by the same antisera as the chosen immunogen, it is "immunologically cross reactive" with the chosen immunogen.

Compound Screening Assays

The present invention provides a variety of compound screening assays for detecting compounds which modulate the effect of Hrd proteins and the proteasome on the degradation of HMG-CoA reductase. Modulating the rate at which HMG-CoA reductase is degraded affects the amount of cholesterol synthesized by the cell, thereby modulating hypercholesterolemia or hypocholosterolemia, depending upon whether the compound increases or decreases the amount of HMG-CoA available for cholesterol synthesis.

Because the HRD genes and the proteasome represent points in the HMG-CoA reductase degradation pathway which were not previously described, the development of screening assays which monitor the effect of the HRD genes and the proteasome on HMG-CoA reductase degradation are of considerable commercial value.

The invention provides both in vitro and in vivo screening assays. In one embodiment, the genome reporter matrix of Saccharomyces to elevated degradation of HMG-CoA reductase is measured using the methods described in the copending and commonly assigned patent application for "Systems for Generating and Analyzing Stimulus-Response Output Signal Matrices and Methods for Drug Screening" (inventors: Nicholas Matthew Ashby and Jasper Rine; filed the week of Aug. 14, 1995; U.S. Ser. No. 08/365,884 docket No. UC Case No B-95-034), in which the genome reporter matrix is screened for a compound that produces the same, or a related response profile.

The principle of the genome reporter matrix is as follows. First, a set of reporters for all genes in a genome is constructed. These reporters can be either fusion proteins, such as the green fluorescent protein, or they can be nucleic acid arrays that can be hybridized to any mRNA or cDNA isolated from cells. Two types of data are collected. First, the response of the entire set of reporters to a mutation in each gene is collected, creating a set of about 6000 genetic response profiles, one for each gene in yeast. Next, chemical compounds are used to treat the cells carrying the reporters, and the response of the entire genome is collected for any changes caused by any compound. Thereafter, the compound response profiles are compared to the genetic response profiles, and any matches identify a protein that is a target of the compound. In this way, all possible protein targets in a cell can be screened in one step.

With respect to using the genome reporter matrix in connection with degradation of HMG-CoA reductase, there are two ways in which this is typically achieved. First, the genetic response profile of hrd mutants is measured. This profile differs from the response profile of wild type cells in the expression pattern of roughly 10% of genes, based upon comparable studies with other systems. Compounds are then screened to identify compounds which convert the response profile of a hrd mutant to that of wild type. Such compounds are those which upregulate the degradation of HMG-CoA reductase. One could use hrd genes that are not part of the proteasome for this purpose. Second, as taught supra, mutants can be found that accelerate the degradation of HMG-CoA reductase. These mutants can be used to create a genetic response profile. It is desirable to screen for chemical compounds that match the response profile of these mutants.

Other in vivo assays are also described herein. In one class of embodiments, methods of identifying compounds that modulate HMG-CoA reductase degradation are provided, in which test compounds are applied to a yeast strain containing elevated levels of HRD proteins (e.g., by cloning the HRD protein into an expression vector in the yeast, or by isolation of an appropriate mutant strain of yeast), in conjunction with application of the test compound to a strain of yeast with normal levels of HRD proteins. Compounds which differentially effect the growth of the two strains of yeast have an effect on the degradation of HMG-CoA reductase, and therefore an effect on the synthesis of cholesterol. Such compounds are then lead molecules for drug development.

Various in vitro assays are also provided for by the present invention. In one class of embodiments, HMG-CoA reductase, proteasomes, and Hrd polypeptides are provided in solution. The rate of HMG-CoA reductase degradation is monitored in the solution, and the effect of the rate of degradation upon the addition of a test compound is monitored. Compounds which effect the rate of degradation are lead molecules in cholesterol modulation drug discovery efforts. The ability to identify such lead molecules by the in vitro and in vivo techniques described herein are of considerable importance to pharmaceutical and biotechnological companies worldwide.

The particular format of the assays depend on the equipment available and the convenience of the investigator. The rate of degradation for HMG-CoA reductase is monitored in standard immunoassays as described herein. For example, in one assay format, the assay solutions are provided in microtitre wells on 96 well plates, and the resulting degradation monitored by ELISA or western blotting.

Each of the in vivo and in vitro screening assays described herein are suitable for incorporation into kits. Such kits typically comprise a container, instructional materials explaining the assay and reagents for practicing the assay.

Quantification of Polypeptides, Nucleic Acids and Antibodies

Antibodies as well as the polypeptides and nucleic acids of the invention can be detected and quantified by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling and scintillation counting, and affinity chromatography.

Reduction of Nonspecific Binding

One of skill will appreciate that it is often desirable to reduce nonspecific binding in immunoassays and during analyte purification. Where the assay involves a polypeptide, antibody, or other capture agent immobilized on a solid substrate, it is desirable to minimize the amount of nonspecific binding to the substrate. Means of reducing such nonspecific binding are well known to those of skill in the art. Typically, this involves coating the substrate with a proteinaceous composition. In particular, protein compositions such as bovine serum albumin (BSA), nonfat powdered milk, and gelatin are widely used.

Other Assay Formats

Western blot analysis can also be used to detect and quantify the presence of a polypeptide or antibody (peptide, transcript, or enzymatic digestion product) in the sample. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein (antibody or polypeptide). The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41).

Labels

Labeling agents include, for example, monoclonal antibodies, a polyclonal antibodies, proteins such as those described herein, or other polymers such as affinity matricies, carbohydrates or lipids. Detection proceeds by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, Southern blotting, northern blotting, southwestern blotting, northwestern blotting, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates and immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the desired component of the assay according to methods well known in the art. As indicated above, a wide variety of labels are used, with the choice of label depending on the sensitivity required, ease of conjugation of the compound, stability requirements, available instrumentation, and disposal provisions.

Nonradioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of antibodies. In this case, antigen-coated (e.g., Hrd polypeptide-coated) particles are agglutinated by samples comprising the target antibodies. In this format, none of the components need be labeled and the presence of the target antibody is detected by simple visual inspection.

Substrates

As mentioned above, depending upon the assay, various components, including the antigen, target antibody, or anti-human antibody, are typically bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic can be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which are appropriate depending on the assay include paper, glasses, ceramics, metals, metalloids, semiconductive materials, cements and the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials are optionally employed, e.g., as laminates, to obtain various properties. For example, protein coatings, such as gelatin can be used to avoid nonspecific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970) which are incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

The Proteasome

Normal cellular function requires that some proteins have long half-lives, that some proteins have short half-lives, and that some proteins have half-lives that are subject to physiological regulation. The degradation of short lived and regulated proteins occurs through a degradation pathway that begins with the conjugation of ubiquitin to the protein that is to be degraded, followed by its rapid degradation.

Ubiquitin is a marking mechanism for proteins that are to be degraded. The molecular machine that is responsible for the degradation is known as the proteasome complex. The proteasome complex is 26S in size with a mass exceeding 2 megadaltons. There is tremendous structural and functional conservation of the proteasome throughout the eukaryotes, from yeast to humans, and also with related bacterial proteins.

The 26S proteasome complex consists of a 20S particle known as either the proteasome itself or the multicatalytic protease. For a review of the proteasome, see Rechsteiner et al., (1993) *Journal of Biological Chemistry* 268(9):6065–8; Goldberg (1995) *Science,* 268(5210):522–3, and Tanaka et al. (1992) *New Biologist* 4(3): 173–87. For a discussion of the yeast proteasome, see, Chen, et al. (1995) *Embo Journal* 14(11):2620–30. Accessory proteins make up the remainder of the mass of the 26S proteasome complex. Some of these accessory proteins target the proteasome to specific target proteins. In effect, the accessory proteins make distinct subpopulations of proteasome complexes that can, in principle, carry out different and specific roles. Some alternate subunits of the proteasome in humans are encoded by genes in the MHC complex, implicating the proteasome in the process of antigen presentation.

Prior to the work described in this invention, there was no evidence that the proteasome was involved in the regulation of HMG-CoA reductase degradation. The discovery of the HRD genes and the similarity of HRD2 to TRAP-2 indicate that there are specific proteins that target the proteaosome to HMG-CoA reductase. Since the degradation of HMG-CoA reductase degradation is a regulated process, the activity of these proteins must also be regulated. Small molecules that activate these proteins have the capacity to trigger the degradation of HMG-CoA reductase, and effectively lower cholesterol synthesis. Thus, the present invention provides a major new commercial target for drug discovery, including commercially valuable screening assays.

Making HMG-CoA reductase Genes Which Are Not Regulated by Flux Through the Mevalonate Pathway With respect to the discovery of genes and proteins involved in the degradation of HMG-CoA reductase, one feature of this invention is the development of a form of HMG-CoA reductase whose degradation is no longer subject to regulated degradation by flux through the mevalonate pathway. That is, the degradation of this form of the enzyme is constitutive and is not stabilized by lovastatin treatment. Selection of lovastatin resistant yeast colonies led to the discovery of the HRD genes as described herein.

To make the unregulated form of HMG-CoA reductase, the HMG2 gene of yeast was cleaved at two restriction sites that correspond to the loop region between the first two transmembrane domains. The gene was cleaved at the AflII site and then was made blunt by treatment with klenow fragment of DNA polymerase 1. The gene was then cleaved with Spe1, effectively removing most of the coding information for the first loop. Into this gap, the 6-cmyc epitope coding fragment was inserted.

The 6-cmyc epitope fragment was obtained as a gift from Mark Roth of the Fred Hutchinson Cancer Research Center in Seattle (termed herein the pJR1265 plasmid). This plasmid was cleaved with HincII and Spe1, which liberated a fragment that could be cloned directly into the gapped HMG2 gene. The insertion preserved the original reading frame and resulted in the synthesis of a protein that was constitutively degraded and, hence, caused cells to be sensitive to lovastatin.

Use of Hrd Proteins and HRD Genes to Reduce Hypercholesterolemia in vivo

This invention shows that Hrd proteins and HRD genes are involved in controlling the rate of HMG-CoA reductase degradation. Specifically, it was shown that HRD2 and HRD3 are necessary for normal HMG-CoA reductase degradation. Increased levels of Hrd proteins, including Trap-2, result in increased levels of HMG-CoA degradation. Increased HMG-CoA degradation results in decreased cholesterol synthesis. Accordingly, in one embodiment of the invention, Hrd proteins are used as therapeutic agents to reduce hypercholesterolemia. The proteins are either supplied as polypeptides, or introduced by gene therapy into a hypercholesterolemic patient. Indeed, it is expected that certain forms of hypercholesterolemia are the result of mutant HRD genes, and that certain alleles of HRD genes are less active than other alleles, resulting in variations in blood cholesterol levels in various populations. Finally, hypocholosterolemia can be treated by blocking the activity of the Hrd proteins, for example, by binding an antibody to a Hrd protein in vivo.

Gene Therapy

Gene therapy provides a method for combating chronic diseases which are caused by deficient or defective expression of a gene. In the present invention, HRD nucleic acids (e.g., TRAP-2), in conjunction with appropriate promoter sequences, packaging sequences, integration or cellular targeting sequences are cloned into the gene therapy vector. Typically, the gene therapy vector is a retroviral clone derived from a human or murine retrovirus, in which the gene of interest is inserted between the viral LTR regions (which contain sequences necessary for replication and packaging of the vector into infectious particles). See, e.g., Poznansky et al. (1991) *Journal or Virology* 65(1): 532–536 for a description of the region flanking the HIV 5' LTR's ability to package vector nucleic acids. In another preferred embodiment, adenovirus vectors (AAV vectors) are used as gene therapy vectors. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. The packaged vectors can be used to transduce the cells of an organism by "infecting" the organism through the same pathway as the parent virus of the vector.

Ex Vivo Gene Therapy

Ex vivo methods for inhibiting viral replication in a cell in an organism involve transducing the cell ex vivo with a vector of this invention, and introducing the cell into the organism. See, e.g., Freshney et al., supra, and the references cited therein for a discussion of how to isolate and culture cells from patients. Alternatively, the cells can be those stored in a cell bank (e.g., a blood bank). Thus, a patient with hypercholesterolemia can be treated for the infection by transducing a population of its cells with a gene therapy vector comprising the nucleic acids of the invention, and introducing the transduced cells back into the organism as described herein.

In Vivo Gene Therapy

Gene therapy vectors containing nucleic acids encoding the polypeptides of the invention, or antibodies which specifically bind the polypeptides of the invention, can be administered directly to the organism for transduction of cells in vivo. In addition, the polypeptides of the invention are also administered directly to increase the rate of HMG-CoA reductase degradation and decrease the rate of cholesterol synthesis, and antibodies to the polypeptides of the invention are administered to decrease the rate of HMG-CoA reductase degradation, increasing the rate of cholesterol synthesis.

Administration of gene therapy vectors, antibodies, and Hrd polypeptides can be by any of the routes normally used for introducing a molecule into ultimate contact with blood or tissue cells. The vectors and peptides are administered in any suitable manner, preferably with pharmaceutically acceptable carriers. Suitable methods of administering such vectors and vaccines in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The vectors, alone or in combination with other suitable components, can be made into aerosol formulations to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the vector with a suppository base. Suitable suppository bases include natural or synthetic triglycerides or paraffin hydrocarbons. In addition, it is also possible to use gelatin rectal capsules which consist of a combination of the vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. Parenteral administration is a preferred method of administration. The formulations of gene therapeutic agent or peptide can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. For many vectors, this mode of administration will not be appropriate, because many virions are destroyed by lyophilization. Other vectors (e.g., vectors utilizing an AAV capsid; See, Samulski (1993) *Current Opinion in Genetic and Development* 3:74–80 and the references cited therein provides an overview of the AAV viral life cycle) tolerate lyophilization well.

Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, because cells are typically destroyed by lyophilization.

The dose administered to a patient, in the context of the present invention should be sufficient to effect a beneficial therapeutic response in the patient over time. Many simple tests are known for the detection of blood cholesterol levels, and doses should be increased over time until the desired blood cholesterol levels are obtained. The dose will be determined by the efficacy of the particular vector or peptide employed and the condition of the patient, as well as the body weight or surface area of the patient to be treated. The size of the dose also will be determined by the existence, nature, and extent of any adverse side-effects that accompany the administration of a particular vector, peptide, or transduced cell type in a particular patient. In determining the effective amount of therapeutic to be administered in the treatment or prophylaxis of hypercholesterolemia, the physician needs to evaluate circulating plasma levels, vector toxicities, and progression of the disease. In general, the dose of a naked nucleic acid composition such as a DNA vaccine or gene therapy vector is from about 1 $\mu$g to 100 $\mu$g for a typical 70 kilogram patient, and the dose of a peptide is on the order of 0.1 $\mu$g to 1 mg for a typical 70 kilogram patient.

In the practice of this invention, compositions can be administered, for example, by intravenous infusion, orally, topically, intraperitoneally, intravesically or intrathecally. The preferred method of administration will often be oral, rectal or intravenous, but the vectors can be applied in a suitable vehicle for the local and topical treatment of virally-mediated conditions. The vectors of this invention can supplement treatment of virally-mediated conditions by any known conventional therapy, including HMGCoA reductase inhibitors, blood pressure medications and biologic response modifiers.

For administration, vectors, peptides and transduced cell types of the present invention can be administered at a rate determined by the LD-50 of the composition, and the side-effects of the composition at various concentrations, as applied to the mass and overall health of the patient. Administration can be accomplished via single or divided doses.

Discussion of the Accompanying Sequence Listing

SEQ ID NO:1 provides the sequence of the HRD2 gene from yeast. SEQ ID NO:2 provides the sequence of the HRD3 gene from yeast. SEQ ID NO:7 provides the sequence of the HRD1 gene from yeast. In each case, the information is presented as a DNA sequence. One of skill will readily understand that the sequence also describes the corresponding RNA (i.e., by substitution of the T residues with U residues) and a variety of conservatively modified variations thereof. In addition, the nucleic acid sequences provide the corresponding amino acid sequences by translating the given DNA sequence using the genetic code.

SEQ ID NO:3 provides the protein sequence of the Hrd2p protein from yeast. SEQ ID NO:4 provides the sequence of the Hrd3p protein from yeast. FIG. 8 also provides Hrd3p and Hrd1p polypeptide sequences. In each case, the information is presented as a polypeptide sequence. One of skill will readily understand that the sequences also describe all of the corresponding RNA and DNA sequences which encode the protein, by conversion of the amino acid sequence into the corresponding nucleotide sequence using the genetic code, by alternately assigning each possible codon in each possible codon position. The sequences also provides a variety of conservatively modified variations by substituting appropriate residues with the exemplar conservative amino acid substitutions provided, e.g., in the Definitions section above.

EXAMPLES

A. MATERIALS AND METHODS

1. Materials

The anti-myc 9E10 antibody was used either as ascites fluids (provided by R. Schekman, UC Berkeley) or as cell culture supernatant obtained by growing the 9E10 hybridoma (ATCC # CRL 1729) in RPMI culture medium (Gibco BRL, Grand Island N.Y.) with 10% fetal calf serum. Affinity-purified polyclonal antiubiquitin antibody was generously provided by Arthur Haas ((Tierney et al., *Arch Biochem Biophys* 293: 9–16, 1992); in Medical College, Milwaukee Wis.). All other reagents were obtained as described previously (Hampton and Rine, *J Cell Biol* 125: 299–312, 1994; Hampton et al., *Proc. Natl. Acad. Sci. USA.* 93: 828–833, 1996).

2. Yeast culture and strains

Yeast were grown and transformed using the media, conditions and techniques described earlier (Hampton and Rine, *J Cell Biol* 125: 299–312, 1994; Hampton et al., *Proc. Natl. Acad. Sci. USA.* 93: 828–833, 1996). All experiments were conducted in yeast minimal medium (0.67% yeast nitrogen base; Difco) supplemented as needed. RHY244, the parent strain for the HRD selection, was prepared by transforming the mevalonate auxotrophic strain RHY468 (alias JRY1593; a, ade2-101, his3Δ200, lys2-801, ura3-52, met, hmg1::LYS2, hm 2::HIS3) with plasmid pRM44, that expresses the 6MYC-HMG2 coding region (see below) at the StuI site in the ura3-52 locus. RHY244 was thus a Ura$^+$, Mev$^+$ strain that produced only the 6myc-Hmg2p variant, whose half-life was unregulated, from a single copy of the coding region expressed from the strong, constitutive GAPDH promoter (previously called the GPD promoter (Hampton and Rine, 1994; Hampton et al., *Proc. Natl. Acad. Sci. USA.* 93: 828–833, 1996)). Strain RHY183 expresses normal Hmg2p from the same GAPDH promoter (Hampton and Rine, *J Cell Biol* 125: 299–312, 1994). Candidate mutants from the HRD selection were cured of the original integrated pRH244 and, thus, were restored to Ura$^-$, Mev$^-$ status, by growth of each strain on 5-FOA plates supplemented with 10 mg/ml mevalonic acid (Boeke et al., *Methods Enzymol* 154: 164–75, 1987). These strains were used to test each mutant for plasmid-independence of the mutant phenotypes under study by retransformation with pRH244 to restore the expression of 6myc-Hmg2p, and testing for phenotypes. The same Ura⁻, Mev⁻ strains were also transformed with plasmids expressing normal Hmg2p from the GAPDH promoter in order to examine the effects of each mutation on the degradation of normal Hmg2p. Ura⁻ versions of each mutant strain and the original parent were also prepared from the resulting Ura⁻, Mev⁻ auxotrophs by integrative transformation with pRH405, a variant of pRH244 that had an AatII/PpuMI fragment containing the entire promoter and 5' coding region of URA3 removed. The resulting plasmid could still be integrated at the ura3-52 StuI site, and resulted in a strain that expressed the 6myc-Hmg2p (Mev⁺), but remained Ura⁻. Such Mev⁺, Ura⁻ strains were prepared from the wild-type parent and the three mutants hrd1-1, hrd2-1, and hrd3-1, and were named RHY400, 401, 402 and 403, respectively. The resulting three mutant strains were used as recipients of a YCp50-based genomic library (URA3 marker) in order to clone the wild-type HRD genes (Rose et al., *Gene* 60: 237–43, 1987). Strains RHY513 and RHY514, which expressed the normally regulated Hmg2p-GFP florescent reporter protein (Hampton et al. *Proc. Natl. Acad. Sci. USA*. 93: 828–833, 1996), were made by transforming RHY400 (Hrd⁺) and RHY401 (hrd1-1) with pRH469, an integrating plasmid containing the HMG2::GFP coding region (with the S65T bright mutation in the GFP coding region) under the control of the GAPDH promoter to examine the dynamics of the Hmg2p-GFP reporter protein in a hrd1-1 mutant. pRH469 was integrated at StuI site of ura3-52, and transformants were selected for Ura⁺.

3. Molecular cloning

The 6myc-Hmg2p protein was expressed from plasmid pRH244. pRH244 was made by altering the HMG2 coding region in the integrating HRA3 plasmid, pRH144-2, that expressed the HMG2 coding region from the GAPDH promoter (Hampton and Rine, *J Cell Biol* 125: 299–312, 1994). The term GPD has been used on numerous occasions (e.g., Schena et al., *Methods Enzymol* 194: 389–98, 1991) to indicate the glyceraldehyde 3-phosphate dehydrogenase promoter as cloned and characterized by Bitter and Egan (*Gene* 32: 263–74, 1984). However, there are two other yeast genes designated GPD1 and GPD2 that do not encode glyceraldehyde 3-phosphate dehydrogenase, but rather sn-glycerol-3-phosphate dehydrogenase (NAD⁺), which are highly regulated enzymes subject to numerous controls (Eriksson et al., *Microbiol* 17:95–107 1995). Therefore, the strong constitutive promoters used herein and in our previous studies pGAPDH are now referred to so as to distinguish them from the unrelated GPD genes.

The 6MYC-HMG2 coding region was prepared by inserting a 299 bp HincII/SpeI fragment containing 6 tandem myc epitopes from pRH360 into the AatII (blunt) and SpeI sites of pRH144-2 (Hampton and Rine, *J Cell Biol* 125: 299–312, 1994). The result of this cloning is to replace most of the first putative cytosolic loop of Hmg2p with a similarly sized, in-frame fragment encoding 6 tandem myc epitope tags (Evan et al., *Mol Cell Biol* 5: 3610–6, 1985) (FIG. 1a). The YCp50-based (ARS/CEN, URA3) yeast genomic library used to clone the three HRD genes was provided by Paul Herman (UC Berkeley). Plasmid pRH469, which expressed the HMG2::GFP(S65T) "bright" version of the previously described HMG2::GFP coding region (Hampton and Rine, *J Cell Biol* 125: 299–312, 1994), was prepared by replacing the MscI/SalI of pRH408 with the corresponding MscI/SalI fragment of pS65T-C1 (Clonetech) in order to introduce the S65T mutation into the GFP portion of the HMG2-GFP coding region. The TRAP-2 coding region was cloned from the plasmid pTRAP-SK, with the TRAP-2 coding region cloned into Bluescript II SK, provided by Dr. David Donner (University of Indiana Medical Center), into the integrating URA3 plasmid pRH98-1 (ARS/CEN, URA3) so that the coding region was under the control of the GAPDH promoter. pRH98-1 was made in the same manner as pRH98-2 (Hampton and Rine, *J Cell Biol* 125: 299–312, 1994), but with the ARS/CEN parent vector Yplac33 instead of the integrating Yplac211 (Gietz and Sugino, *Gene* 74: 527–34, 1988). It was noted that a portion of the TRAP-2 cDNA, originally designated as a portion of untranslated leader upstream of the ATG codon, in fact encoded ~37 more amino acids that were nearly identical to the corresponding amino acids in the longer submission in the database called "human 26S proteasomal subunit p97" (see, below). The 37 extra amino acids encoded in the leader region are SGGT-DEKPSGKGRRDAGDKDKELELSEEDKQLQDELV SEQ ID NO:21. Accordingly, a synthetic linker was designed that provided a new ATG in-frame to this upstream portion in order to produce a protein in yeast that included these extra amino acids. The linker was produced by annealing the two oligonucleotides: 5'-GATCCCCATGGCCTGCA-3'SEQ ID NO:22 and 5'-GGCCATGGG-3'(SEQ ID NO:23). When used as described, the linker adds the peptide MACRN to the 37 amino acid extension to TRAP-2 listed above, thus providing a new upstream start codon. The distal Pst1 site 3' to the stop codon of TRAP-2 was removed. The ATG-providing linker was next cloned into the remaining Pst1 and BamHI sites immediately 5' to the start of the coding region. Finally, the BamHI/SalI fragment with the now-extended coding region was placed in the same sites of pRH98-2 to yield pRH497.

4. The HRD selection

The "wild-type" (Hrd⁺) parent strain was RHY244 (hmgl::LYS2, hmg2:.HIS3, ura3-52:.pGAPDH-6MYC-HMG2::URA3) which expressed only the 6myc-Hmg2p, whose half-life was unregulated, as its sole source of essential HMG-R activity. Selection plates consisted of minimal solid medium (0.67% Difco Yeast Nitrogen Base/2% glucose), supplemented with adenine sulfate (30 mg/l) and methionine (30 mg/l), and containing 200 μg/ml of lovastatin, a competitive inhibitor of HMG-CoA reductase. Cells from individual clonal liquid cultures of non-mutagenized RHY244 were plated onto solid supplemented minimal medium containing lovastatin at a density of ~2×10⁶ cells per plate, and incubated at 34° C. until discrete colonies appeared in 1–2 weeks. Typically, a plate had between 1-10 colonies. A total of 20 plates was used for the HRD selection. Individual colonies from the plates were grown on supplemented minimal medium plates without lovastatin, and then tested for maintained resistance following non-selective growth. True-breeding candidates were evaluated for steady-state levels of the 6myc-Hmg2p protein by immunoblotting lysates from log-phase cultures for myc immunoreactivity. Finally, strains were tested for stabilization of the 6myc-Hmg2p by immunoblotting after growth into stationary phase (see, below). Promising candidates were chosen such that each candidate came from a different selection plate and were thus independent. Final candidates were tested by cycloheximide-chase and pulse-chase to determine whether the effects on the steady-state level of 6myc-Hmg2p were attributable to alterations in the gradation. Each candidate with stabilized 6myc-Hmg2p was cured of the original 6myc-Hmg2p expression plasmid (to give Mev⁻, Ura⁻ cells), and then retransformed with pRH244 to test for plasmid-independence of phenotypes. The same Mev⁻, Ura⁻ cells were also transformed with a plasmid expressing normal Hmg2p from the GAPDH promoter to test the ability of each candidate to degrade normal Hmg2p protein.

5. Genetic analysis of the hrd mutants

The mutations that stabilized 6myc-Hmg2p were tested for dominance by mating each to an a version of the parent strain and by isolating zygotes from a mating mixture to form diploids that were isogenic (except for any mutations) to the original strain. The resulting diploids were then tested for lovastatin resistance and stabilization of the 6myc-Hmg2p protein. The diploids were sporulated and the resulting haploid progeny analyzed for lovastatin resistance and stabilization of the 6myc-Hmg2p protein. The distribution of the Hrd-phenotype among the progeny was used to evaluate the number of loci underlying the phenotype of each mutant.

To perform complementation analysis of the mutants, a representative a mating type strain was recovered for each mutant from the tetrad analysis. Mutant strains of both mating types were used to make diploids heterozygous for different mutations. Each diploid was tested for stabilization of 6myc-Hmg2p. Each heterozygous diploid was then sporulated and separated into haploid progeny. The pattern and frequency of lovastatin resistance among the progeny indicated whether the two combined mutations in a given heterozygotes were allelic or unlinked. These analyses revealed the existence of three unlinked loci, HRD1, HRD2 and HRD3, in which recessive mutations stabilized both 6myc-Hmg2p and Hmg2p.

6. Cloning of the HRD genes

Representative hrd mutants were chosen for cloning the wild-type allele by plasmid complementation. These mutants are referred to as hrd1, hrd2-1 and hrd3-1. For each of these mutants, the Mev⁻, Ura⁻ strain that was made by 5-FOA-selected loss of the 6myc-Hmg2/URA3 plasmid was transformed with a variant of the pRH405 plasmid (6myc-Hmg2p, ura3Δ see above), allowing restored expression of the 6myc-Hmg2p, in cells that were URa⁻. The resulting Hrd⁻, Mev⁺, Ura⁻ strains, each bearing a single recessive hrd mutation, were called RHY401, 402 and 403, and harbored the hrd1, hrd2-1 and hrd3-1 mutation, respectively. Each mutant was transformed with a yeast genomic library (YCp50 (ARS/CEN); Rose et al., *Gene* 60: 237–43, 1987) selecting for Ura⁺ transformants. Master plates of the resulting Ura⁺ colonies were replica-plated onto supplemented minimal medium with lovastatin to identify colonies that regained wild-type sensitivity to lovastatin. Plasmids were recovered from candidate lovastatin-sensitive colonies and retested by retransformation of the mutant strain. Purified plasmids that could restore wild-type lovastatin sensitivity and 6myc-Hmg2p degradation to a given hrd mutation were analyzed by sequencing the flanks of the particular ends of the insert DNA using sequencing primers flanking the YCp50 BamHI site. This information was used to ascertain the genomic location of the insert. Each plasmid was then analyzed by subcloning to test each candidate coding region in a given insert for the ability to complement the appropriate hrd mutant. Finally, each single candidate coding region was cloned into an integrating (YIp, URA3) plasmid, integrated at its homologous genomic location in a α, ura3 version of Hrd⁺ parent strain (RHY454). The resulting strain with the cloned locus marked with the URA3 gene was crossed to the corresponding URA⁻ hrd mutant. The resulting diploid with the cloned gene marked with URA3 were then subjected to tetrad analysis and examined for segregation of the URA3 marker and the hrd mutation. The segregation of 2 Hrd⁺; 2Hrd⁻ and 2 Ura+: 2 Ura⁻ in all tetrads such that the Ura+ cells were always Hrd+ (and the Ura– cells were always Hrd) was genetic proof of having cloned the wild-type gene underlying the hrd mutation under study.

7. Access to sequence information

Unless otherwise noted, the numbers are for GenBank entries for the following protein and corresponding nucleotide sequences are: Hrd2p: U10399, coding region YHR027c; TRAP-2: U12596; "human 26S proteasome subunit p97": D78151; Sen3p: L06321; Hrd3p: PIR database S48558; sel-1: U50828 and U50829; Ibd2: U11037; *S. pombe* unknown protein: D83992, coding sequence 3030–3566; Sktsp: S65415. The HRD1 gene can be accessed on the World Wide Web (http://genome-www.stanford.edu/Saccharomyces/). HRD1 is on chromosome XV fragment #0295, nucleotides 295001–305000. The start of the coding region has the following sequence: ATG GTG CCA GAA AAT AGA AGG AAA CAG TTG GCA ATT TTT G (SEQ ID NO:24). The predicted HRD1 coding region is on the complementary strand, and begins 97 bp away from the unique SAlI site in the fragment.

8. Analysis of protein stability

The stability of 6myc-Hmg2p and Hmg2p were assayed in three ways, each of which has previously been described (Hampton and Rine, *J Cell Biol* 125: 299–312, 1994; Hampton et al., *Proc. Natl. Acad. Sci. USA*. 93: 828–833, 1996). Briefly, they are: (1) pulse-chase analysis using [³⁵S] labeling followed by immunoprecipitation; (2) cycloheximide chase in which log-phase cells treated with cloheximide and periodically immunoblotted to follow the degradation of the entire pool of a particular protein; and (3) "stationary chase" in which cells are grown ~12–15 hours at 30° C. after the cells have attained a mid-log phase (~0.5 $OD_{600}$) culture density to achieve stationary phase, followed by immunoblotting. The "stationary chase" reports the continued degradation of the pool of protein under study after protein synthesis has ceased due to depletion of nutrients. This method reports the regulated degradation of Hmg2p as well as that of Hmg2p-GFP (Hampton et al., *Proc. Natl. Acad. Sci. USA*. 93: 828–833, 1996). Preparation of cell lysates for immunoblotting were made as described by Hampton and Rine, (*J Cell Biol* 125: 299–312, 1994). The myc tag was sufficiently specific in these strains to allow dot-blotting of the crude lysates for the specific detection of the 6myc protein. Lysates were placed in a 96 well dish and transferred by a multi-prong transfer device (Sigma) to a piece of dry nitrocellulose which was then processed for immunoblotting. Immunoblotting for the myc tag, whether by dot blotting or gel immunoblotting, was performed as described for anti-Hmg2p by Hampton and Rine, (*J Cell Biol* 125: 299–312, 1994), except that the 9E10 monoclonal anti-myc antibody was used at a 1/2000 dilution of murine ascites fluid, or a 1/9 dilution of hybridoma supernatant, and the secondary antibody was goat-anti-mouse-HRP (Gibco BRL, Grand Island, N.Y.). The ECL detection reagents (Amersham, Arlington Heights, Ill.) were used in all immunoblotting procedures.

9. GFP fluorescent microscopy

The fluorescence of strains expressing the HMG2::GFP (S65T) gene in a wild-type (RHY513) or hrd1-1 (RHY514) background was evaluated by fluorescence microscopy using a Nikon Optiphot II microscope with a Cohu (San Diego Calif.) CCD, a Colorado Video Integrator (Boulder, Colo.) and a Sony Graphic Printer. The images shown were directly digitized on a Hewlett-Packard Scanjet 3C scanner. The cells were grown into stationary phase from cultures of $OD_{600}$ 0.5 for 15 hours and photographed directly from the cultures.

10. Global ubiquitination assay

Ubiquitination of total cellular proteins was assessed by immunoblotting whole cell lysates with an affinity-purified polyclonal rabbit anti-ubiquitin antibody.

B. Results

To study the regulated degradation of yeast Hmg2p in isolation from any other possible form of regulation, strains were used that express Hmg2p, but not the Hmg1p isozyme, from a single integrated copy of the HMG2 gene whose promoter has been replaced by the more powerful constitutive GAPDH promoter. As previously demonstrated (Hampton and Rine, *J Cell Biol* 125: 299–312, 1994; Hampton et al., *Proc. Natl. Acad. Sci. USA.* 93: 828–833, 1996), Hmg2p released in this manner is subject to regulated degradation. Thus, strains constitutively expressing Hmg2p in this way have a steady-state level of HMG-CoA reductase activity that is determined entirely by the high constitutive synthesis rate combined with the rate of degradation.

The selection for mutants deficient in Hmg2p degradation was based on the prediction that such mutants would have a higher steady-state level of Hmg2p. Because the HMG-R enzyme activity is essential, drugs that inhibit HMG-R, such lovastatin, kill cells in a dose-dependent fashion. Thus, mutants with a higher steady-state level of HMG-R would be expected to have heightened resistance to lovastatin, and so be selectable from wild-type cells in growth medium containing a normally toxic dose of the drug.

The selection for degradation mutants was first attempted with a strain that lacked both endogenous HMG-R genes (hmg1::LYS2 and hmg2:H153) and had a single integrated copy of the HMG2 gene driven by the constitutive GAPDH promoter. Growth of this strain was blocked by lovastatin in a dose-dependent fashion (FIG. 1d, ovals). However, even at the highest practical doses of the drug, the plating efficiency of surviving colonies was on the order of 0.1–1% for non-mutagenized cells. Furthermore, the survivors did not remain lovastatin resistant after outgrowth in the absence of the drug. Thus, the lovastatin resistance that the surviving colonies acquired was the result of physiological, rather than genetic, changes in the cells. It was reasoned that the high plating efficiency on medium containing lovastatin might be due, at least in part, to the cell's ability to slow Hmg2p degradation, increasing Hmg2p steady state level, when lovastatin slowed the mevalonate pathway. In effect, lovastatin would induce higher levels of its own target. In this way, the normal regulation of Hmg2p stability would blunt the effects of lovastatin and hinder the recovery of mutants.

1. 6myc-Hmg2p: an unregulated reductase

To remove the contribution of regulated degradation to the high survival rate in the selection, a variant was developed of the Hmg2p molecule, 6myc-Hmg2p (FIG. 1a), whose degradation was not regulated by alterations in the mevalonate pathway (FIGS. 1b and 1c). The addition of a small dose of lovastatin to cultures dramatically stabilized wild-type Hmg2p, whereas the degradation of the 6myc-Hmg2p molecule was unaffected. Two independent assays of whole-pool degradation were used: addition of cycloheximide to the cells followed by immunoblotting (FIG. 1b), and growth of cells into early stationary phase such that the synthesis of protein ceases while degradation proceeds, also followed by immunoblotting (FIG. 1c). In both procedures the degradation of Hmg2p was strongly inhibited by slowing the mevalonate pathway, whereas the degradation of the 6myc-Hmg2p protein was unaffected. Thus, conditions known to stabilize Hmg2p had no effect on 6myc-Hmg2p. In all other ways, the 6myc-Hmg2p protein behaved like Hmg2p. 6myc-Hmg2p complemented lethal mutations in the wild-type HMG-R genes. Like Hmg2p, 6myc-Hmg2p protein was an integral membrane protein that could be solubilized only by detergent treatment. Finally, 6myc-Hmg2p was degraded at a similar rate to Hmg2p under normal growth conditions (0.5–1 hour half-life), and degradation was independent of vacuolar proteases or the secretory pathway. Curiously, the electrophoretic ability of the 6myc-Hmg2p protein was less than would be predicted from the sequence of the coding region. Although the protein would be expected to be near identical in mass to normal Hmg2p (~115 kD), the mobility of 6myc-Hmg2p reproducibly ran at a position on denaturing SDS-PAGE gels that was expected for a protein of ~140 kD. This difference in mobility is shown in FIG. 1c, in which the panels are aligned as on the original gel. The altered mobility of the 6myc variant was not due to N-linked glycosylation.

A comparison of otherwise isogenic strains expressing either the HMG2 gene or the 6MYC-HMG2 gene from the strong GAPDH promoter at the same integration rate revealed that the strain expressing the 6myc-Hmg2p unregulated construct was more sensitive to lovastatin in liquid medium (FIG. 1d, diamonds). When cells that expressed 6myc-Hmg2p (RHY244) were plated on solid lovastatin-containing medium, the plating efficiency was on the order of 1 in $10^6$, as compared to the ~1% observed with the isogenic strain (RHY183) that expressed wild-type Hmg2p. It would appear that the loss of regulation of 6myc-Hmg2p degradation indeed resulted in a greater sensitivity to lovastatin. It should be noted that the steady-state of the 6myc-Hmg2p, as measured by immunoblotting, was approximately three-fold less than the steady-state level of wild-type Hmg2p expressed in the same strains under the same conditions. The reason for this quantitative difference was unknown. Nevertheless, the drastically decreased plating efficiency of strains with 6myc-Hmg2p on lovastatin allowed the successful selection of hrd mutants, described below.

2. The HRD selection

Mutants defective in the degradation of HMG-CoA reductase would identify the underlying machinery that brings about the degradation of this enzyme. The mutants defined the HRD genes (pronounced "herd", for Hmg-CoA Reductase Degradation). The selection that resulted in isolation of these mutants, known as the HRD selection, is represented in FIG. 2. In a strain expressing only the 6myc-Hrng2p protein, which had an unregulated half-life, lovastatin sensitivity was a simple indicator of Hmg2p steady-state levels because the drug itself no longer slowed the degradation of Hmg2p. Cells with an elevated steady-state level of 6myc-Hmg2p caused by a hrd mutation (left panel, "X") were selected by plating cells expressing the 6myc-Hmg2p as their only form of HMG-CoA reductase on medium containing ~1 in $10^6$ plating efficiency. The plates were incubated at 34° C. and allowed to grow for ~1 week. The elevated temperature was chosen because the selection works quickly at this temperature.

Resistant colonies were tested for three different phenotypes as described in Section A, Materials & Methods: 1) continued lovastatin resistance following nonselective growth; 2) increased steady-state levels of 6myc-Hmg2p; and 3) increased half-life of 6myc-Hmg2p, as shown for the hrd1-1 mutant (FIG. 3a). The hrd1-1 mutant clearly was more resistant to lovastatin than the wild-type parent (FIG. 3a, left panel). The concentration of lovastatin used in this experiment was significantly higher than that used in the selection itself (500 vs. 200 μg/ml). To assess the stability of the entire 6myc-Hmg2p pool, log-phase cultures were treated with cycloheximide at time zero and subjected to immunoblotting analysis with the 9E anti-myc monoclonal antibody after cessation of protein synthesis (FIG. 3a, middle panel). The 6myc-Hmg2p was more stable in the mutant than in the wild type. Furthermore, comparison of the 0 hour lanes demonstrated that the steady-state levels of the 6myc protein was elevated in the mutant, presumably as a result of slowed degradation. Finally, the 6myc-Hmg2p protein was also stabilized in a pulse-chase experiment, but the synthesis rates of the protein, as approximated from the pulse-labeled intensity at time 0, were comparable between the mutant and the wild type (FIG. 3a, right panel). The similarity in the initial amount of pulse-labeled protein between the mutant and parent strain indicated that the primary defect of the mutants was in the degradation of the 6myc-Hmg2p protein. All mutants described here showed similar mutant phenotypes: increased lovastatin resistance, elevated steady-state levels of 6myc-hmg2p and slowed degradation of this protein assured both by immunoblotting or by pulse-chase experiments.

3. Analysis of the hrd mutations

The HRD selection was sufficiently powerful to allow selection of mutants from a non-mutagenized culture. Eleven independent mutants were isolated that passed all of the phenotypic tests. Heterozygous diploids formed by mating each mutant to an isogenic parent strain the opposite mating type were all sensitive to lovastatin and degraded 6myc-Hmg2p at nearly wild-type rates. Therefore, all mutants were recessive to wild-type for lovastatin resistance and stabilization of 6myc-Hmg2p. Sporulation of these heterozygous diploids and analysis of phenotypes of the meiotic progeny revealed that the lovastatin resistance and stabilization of the 6myc-Hmg2p protein cosegregated. At least 20 tetrads were analyzed for each heterozygous diploid. 9 of 11 mutations segregated as single Mendelian alleles into the meiotic progeny, mg a pattern of 2:2 hrd:hrd$^+$ as shown for the hrd1-1 mutant in FIG. 3b. The remaining two mutants showed a segregation pattern consistent with two unlink mutations that were both required for the Hrd$^-$ phenotype. Although these 2 mutants were not studied further, their isolation indicated the power of the hrd selection, since these double mutations were selected from non-mutagenized cells.

4. The three HRD genes

The 9 remaining mutants were characterized by complementation analysis. hrd mutants of each mating type were recovered from meiotic progeny described above. These segregants were used to make heterozygous diploids between pairs of the various hrd mutants. The resulting diploids were then analyzed for lovastatin sensitivity and subsequently sporulated, dissected, and tested for the segregation of the mutant phenotypes into the meiotic progeny. The results of these tests indicated that the 9 single recessive mutations fell into 3 unlinked complementation groups. The underlying wild-type genes were referred to as HRD1, HRD2, and HRD3. Among the 9 independent isolates, 5 were hrd1 mutants, 3 were hrd3 mutants, and hrd2 was represented by a single allele.

5. Mutants stabilized normal Hmg2p

Figure 1:
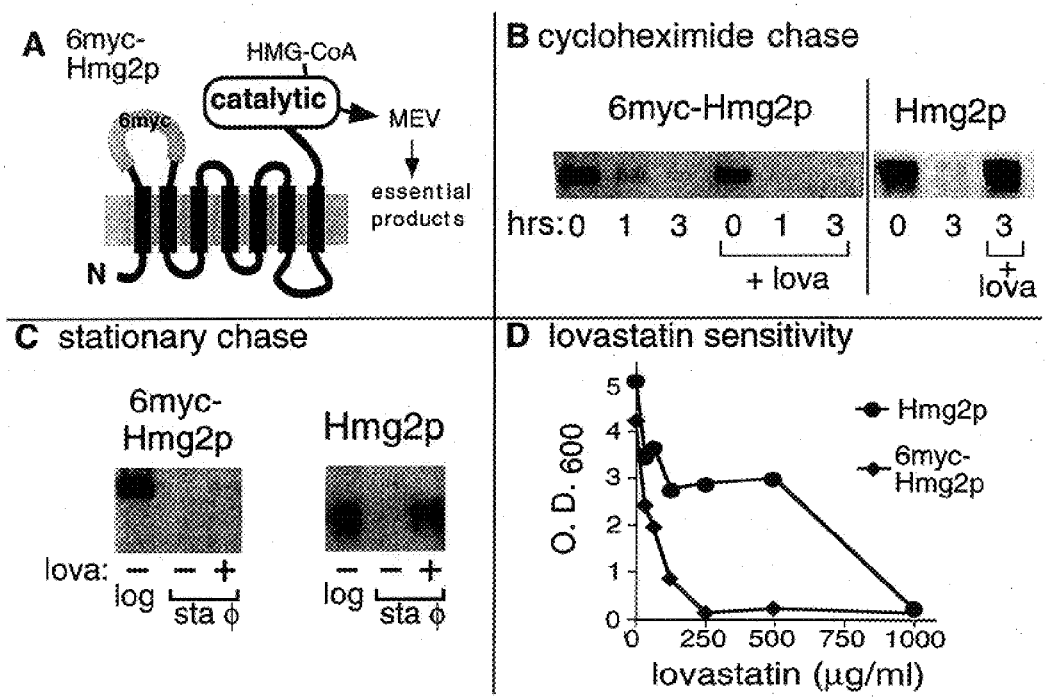
FIG. 1. 6myc-Hmg2p: an unregulated variant of Hmg2p. A) schematic diagram of the unregulated 6myc-Hmg2p. The 6myc protein had a portion of the protein sequence replaced between the first two putative transmembrane spans (see Basson et al., *Mol Cell Biol* 8: 3797–808, 1988)) with 6 tandem myc epitope tags. The tagged protein was still capable of catalyzing the reduction of 3-hydroxy-3-methyl glutaryl CoA (HMG-CoA) to mevalonate (MEV), an essential intermediate of cholesterol biosynthesis. B) The degradation of 6myc-Hmg2p was not regulated by the mevalonate pathway. Cells expressing 6myc-Hmg2p (RHY244) or Hmg2p (RHY183) were examined for degradation of each protein by addition of cycloheximide at time zero and subsequent immunoblotting, as described by Hampton and Rine (*J Cell Biol* 125: 299–312, 1994). In the indicated samples, 50 µg/ml of lovastatin was added along with the cycloheximide at t=0. The 6myc-Hmg2p lanes (left panel) were immunoblotted using the 9E10 anti-myc antibody, and the Hmg2p lanes (right panel) were immunoblotted with affinity purified anti-Hmg1p protein. Each lane contained lysate from ~0.2 O.D.$_{600}$ units of cells. C) Test of 6myc-Hmg2p degradation by "stationary chase." Log phase (OD$_6$~0.5) cultures of the strains used in Panel B were allowed to grow for an additional 15 hours at 30° C., and then subjected to lysis and immunoblotting to evaluate degradation of the expressed reductase (Hampton et al., *Proc. Natl. Acad. Sci. USA.* 93: 828–833, 1996). In the samples labeled "+lova", 50 µg/ml lovastatin was added to the cultures at the mid log phase, and cultures were then incubated an additional 15 hours. The lanes labeled "log"

The 6myc-Hmg2p protein structure was sufficiently different from the parent protein to abrogate regulation of degradation (FIG. 1). Since there are examples where a mutant protein is degraded differently from its wild-type counterpart (Tsuji et al., *Biochemistry* 31:11921–7C, 1992; Papavassiliou et al., *Science* 258: 1941–4, 1992), it was important to determine whether the mutants obtained from the hrd selection were deficient in the degradation of normal Hmg2p. Accordingly, all isolated mutants were cured of the 6myc-Hmg2p-expression plasmid, re-transformed with plasmid expressing the HMG2 gene from the same GAPDH promoter, and tested for degradation of Hmg2p. In all cases, the mutants stabilized the natural Hmg2p (FIG. 4). This experiment was a cycloheximide-chase analysis of Hmg2p in wild-type (left pair) or isogenic strains with single representative mutations, hrd1-1, hrd2-1 and hrd3-1. Each strain had elevated steady-state levels of the Hmg2p, and a concomitant stabilization of that protein. Importantly, the degree to which a given mutant affected the steady-state levels of the 6myc-Hmg2p and wild-type Hmg2p was similar. For example, the hrd1-1 mutation caused a strong stabilization of myc-Hmg2p and a correspondingly high resistance to lovastatin. In contrast, the hrd2-1 mutation stabilized the 6myc-Hmg2p protein to a lesser extent and was relatively less resistant to lovastatin. Similarly, the hrd1-1 mutation also has a greater effect on the size and stability of the Hmg2p pool than did the hrd2-1 mutation. In addition to the three mutants featured in FIG. 4, all isolates from the HRD selection stabilized both Hmg2p and 6myc-Hmg2p.

The ability of hrd mutants to stabilize authentic Hmg2p established that the HRD genes encoded bonafide components of a mechanism for degrading Hmg2p. An interesting question is whether hrd mutants would similarly affect the stability of the Hmg2p-GFP. This Hmg2-GFP fusion protein is degraded and regulated in a manner similar to normal Hmg2p (Hampton et al., *Proc. Natl. Acad. Sci. USA*. 93: 828–833, 1996). However, this fusion protein lacks the entire catalytic domain and, thus, offered a test of whether the membrane-associated domain of Hmg2p was sufficient to confer HRD-mediated degradation of a heterologous protein. The Hmg2-GFP reporter protein was strongly stabilized when expressed in a hrd1-1 strain (FIG. 5). A parallel analysis of the GFP reporter degradation by FACS analysis confirmed the results from microscopy with large numbers of cells (>10,000 per strain). Furthermore, CS analysis of hrd1-1, hrd2-1 and hrd3-1 mutants corroborated the observation that the hrd1-1 and hrd3-1 mutants had stronger degradation phenotypes than the hrd2-1 mutant. Thus, the membrane-associated region of Hmg2p was sufficient for HRD-mediated degradation of fusion proteins.

The hrd mutants were tested for growth at various temperatures, because many classes of mutants with deficiencies in protein degradation are temperature sensitive (ts) (Finley and Chau, *Annu Rev Cell Biol* 7: 25–69, 1991; Hilt and Wolf, *Mol Biol Rep* 21: 3–10, 1995). The hrd2-1 mutant was growth compromised with a doubling time about 60% of the wild-type strain at all temperatures tested, but was not ts. The growth defect of the hrd2-1 strain co-segregated with lovastatin resistance in the haploid progeny from a cross with the isogenic parent strain, indicating that the growth defect was a consequence of the hrd2-1 mutation. In contrast, all of the hrd1 and hrd3 mutants were robust, and grew at rates comparable to the wild-type parent strain at all temperatures tested.

6. Cloning of the HRD genes

Plasmids that complemented hrd1-1, hrd2-1 or hrd3-1 were cloned by transformation of the appropriate strains with a YCp5O-based genomic library, and replica-plating transformants onto lovastatin-containing medium. Plasmids were recovered from transformants that had regained wild-type sensitivity to lovastatin and re-tested for their ability to complement the appropriate mutants. In each case, the candidate plasmid also complemented the defect in 6myc-Hmg2p degradation. The identities of the yeast genomic DNA in each plasmid were determined by sequencing a small portion of each insert with a sequencing primer derived from the regions of the YCp5O parent vector that flanked the BamHI insert site. These sequences were compared to sequences in national databases to determine the sequence and restriction maps of each gene. This information was used to test all candidate coding regions by subcloning and testing for complementation. The genetic linkage of the cloned gene to the mutant loci was tested as described above.

7. The HRD2 gene encoded a subunit of the 26S proteasome

The coding region (YHR027c) that complemented the hrd2-1 mutant encodes a 109 kD protein that was homologous throughout (40% identical and 65% similar) to a human protein that been proposed to be a subunit of the 26S proteasome (FIG. 6). The human protein, referred to as p97, is a member of the PA700 complex that binds to and activates the mammalian 20S proteasome in vitro. Thus, the combined PA700-20S complex has been posited to be the eukaryotic 26S proteasome (DeMartino et al., *J Biol Chem* 269: 20878–84, 1994). It would appear that the YHRO27c coding region is the yeast version of the p97 subunit of the proteasomal PA700 complex. The p97 coding region was first isolated in a search for proteins that can interact with the 55kD TNF receptor, and was referred to in that work as TRAP-2 (Song et al., *J Biol Chem* 270: 3574–81, 1995). A slightly longer version of the same coding region (908 aa vs. 853 aa) was subsequently deposited into Genbank (Accession No. D78151) as that encoding "human 26S proteasome subunit p97", by the laboratory of K. Tanaka.

8. HRD2 was a functional TRAP-2/p97 homologue

The slow growth phenotype of the hrd2-1 mutants would be consistent with hrd2p being a proteasomal component. This possibility was further investigated by examining several other phenotypes. The sensitivity of the hrd2-1 mutant to canavanine, an amino acid analogue of arginine which often shows heightened toxicity towards yeast strains with deficiencies in proteasomal components (Hilt and Wolf, *Mol Biol Rep* 21: 3–10, 1995), was tested. Only hrd2 mutants had heightened sensitivity to canavanine (FIG. 7a). All other alleles of hrd1 or hrd3 were no more sensitive to canavanine than was the isogenic parent strain. The proteasome is the site of degradation of many, but not all, ubiquitinated proteins (Hicke and Riezman, *Cell* 84: 277–87, 1996; Egner and Kuchler, *Febs Lett* 378:177–81, 1996)). Therefore, mutations in proteasome components often result in a general increase in the steady-state levels of ubiquitinated proteins since the degradation rate of these intermediates is decreased when the proteasome is compromised (Hilt and Wolf, *Mol Biol Rep* 21: 3–10, 1995; Papa and Hochstrasser, *Nature* 366: 313–9, 1993). Therefore, the amount of ubiquitin immunoreactivity in whole cell lysates, which was visualized as a characteristic ladder in whole-cell lysates, was compared in wild-type, hrd1-1, hrd2-1 and hrd3-1 strains (see, below) (FIG. 7). Only the hrd2-1 strain showed an elevation in the tensity of the ubiquitin immunoreactivity. Finally, expressing the human TRAP-2 coding region in the hrd2-1 strain restored wild-type sensitivity to lovastatin (FIG. 7c), and wild-type rapid degradation of 6myc-Hmg2p.

Since many proteasomal proteins are essential for viability, we evaluated the phenotype of a hrd2Δ null was evaluated by disrupting the gene in a wild-type diploid, and then sporulated the resultant heterozygous diploid to assess viability of the haploid progeny. In all tetrads dissected, there were 2 live and 2 dead segregants, and none the live haploids bore the marker gene (URA3) used to disrupt the HRD2 gene. Thus, at least in this strain background, the HRD2 gene was essential. Taken together, the combined phenotypes associated with the HRD2 gene (i.e., canavanine sensitivity, slow growth of the hypomorph, lethality of the null allele, ubiquitin conjugate buildup, and complementation by human TRAP-2) all corroborated the identity of Hrd2p as the yeast homologue and analogue of the mammalian p97 unit. Moreover, these data provided in vivo evidence that Hrd2p/TRAP2 is a functional component of the 26S proteasome.

9. Both HRD1 and HRD3 gene encoded novel proteins

Analysis of the sequences of the HRD1 and HRD3 genes indicated that each encoded a novel protein (FIG. 8). Both proteins appeared to have membrane-spanning domains. The HRD3 gene encoded a protein with four features consistent with Hrd3p being a transmembrane protein oriented with the amino terminus on the lumenal site of membrane (see, Sipos and von Heijne, *Eur J Biochem* 213: 1333–40, 1993), and references cited therein, and R. Doolittle, personal communication). These features included: a candidate cleavable hydrophobic N-terminal signal sequence; several asparagine-linked glycosylation consensus sites (NxT/S) in the hydrophilic region following the signal sequence; a hydrophobic region of 22 amino acids with flanking charge density and hydrophobic moment predicted for a transmembrane span; and a relatively small cytoplasmic domain with a stop-transfer sequence immediately adjacent to the transmembrane span. By this model, the short C-terminal region following that transmembrane region would be in the cytosol.

The predicted sequence of Hrd3p was used to design oligonucleotides to generate a disrupting PCR product that would exactly replace the predicted coding region with the URA3 gene (Lorenz et al., *Gene* 158: 113–7, 1995). The disruption was successfully produced in the haploid parent strain used in the HRD selection. The resulting Ura$^+$ transformants in which the marker gene replaced the HRD3 coding region are all strongly Hrd$^-$, that is, they were resistant to lovastatin and displayed stabilization of the 6myc-Hmg2p reporter. These observations indicated that the HRD3 gene was not essential, but was required for the degradation of 6myc-Hmg2p related substrates. In spite of the strong Hrd– phenotypes, the hrd3Δ strain had none of the pleiotropies associated with global deficiencies in protein degradation characteristic of the hrd2-1 mutant and other mutants with proteasomal deficiencies.

The Hrd1p predicted protein was also novel. Again, the protein appeared to have multiple segments that could span membranes (FIG. 8). The hydropathy plot of the predicted Hrd1p protein was more complex than the simple pattern of Hrd3p and, thus, the number of transmembrane domains and putative orientation of the protein was harder to predict. However, it appeared that the N-terminus had more than one transmembrane span, followed by a segment with hydrophobic patches of insufficient length to span a membrane, and a hydrophilic C-terminal region. The first two hydrophobic regions, which are also the longest, are underlined in the Hrd1p sequence in FIG. 8. A simple, yet tentative, model for Hrd1p's structure posits an amino-terminal membrane-associated region with a C-terminal cytosolic domain.

The library plasmid bearing HRD1 was used to make a disruption cassette by insertion of the functional URA3 gene into a gap in the HRD1 coding region created by removal of a 750 bp BstEII fragment directly centered in the coding region. Transformants of the haploid parent strain to Ura$^+$ with an SphI/SalI fragment resulted in lovastatin resistant, Ura$^+$ transformants. Furthermore, the lovastatin resistance was allelic to the genetically isolated hrd1-1 mutation, and linked to the URA3 marker. However, the transformation of haploids with the disruption fragment reliably resulted in ~10 times fewer colonies than identical transformation of a homozygous diploid. Dissection of the diploid resulted in four viable progeny, and the 2 Ura$^+$ offspring showed enhanced lovastatin resistance. These results indicated that the HRD1 null mutation can be generated in a haploid, but that there are perhaps other physiological consequences that must be overcome in the haploid to harbor the null phenotype. Such possible functional features of the HRD1 gene are currently being investigated.

C. DISCUSSION

The foregoing experiments represent a systematic analysis of how HMG-CoA reductase is degraded and how the degradation is regulated. The results obtained indicate that the degradation of HMG-R involved the 26S proteasome, possibly working in tandem with at least two novel proteins to bring about the degradation of Hmg2p. Such results bring several key issues into focus.

In previous studies, it was established that degradation of Hmg2p and of the Hmg2-GFP fusion protein is regulated by the flux through the mevalonate pathway, so that degradation is slowed when the flux is lowered, such as by treatment of cells with lovastatin. The 6myc-Hmg2p protein, constructed herein, was refractory to the stabilization that occur in cells with reduced flux through this pathway. Thus, the amino acid sequence between the first and second of the transmembrane domains of Hmg2p, which are substituted by myc epitopes in the 6myc-Hmg2p, must contribute to the regulation of Hmg2p's degradation. Whether this tract of amino acids is providing specific linear determinants, or structural information needed for regulation is currently being evaluated. In any event, the inability of 6myc-Hmg2p to be stabilized allowed the isolation of hrd mutants defective in Hmg2p degradation.

Mutants in HRD genes, which stabilized Hmg2p, also stabilized wild-type Hmg2p and an Hmg2-GFP fusion protein. Therefore, the HRD genes were part of a mechanism for degrading bona fide HMG-CoA reductase, rather than a mechanism degrading mutant or misfolded proteins. Moreover, the stabilization of the Hmg2-GFF S fusion proteins established that the membrane-associated region of Hmg2p was sufficient to confer HRD-mediated degradation.

The selection of Hrd-mutants and the analysis of the genes identified in this screen offered a window into how HMG-CoA reductase and potentially other membrane proteins are degraded.

1. The HRD genes

The HRD2 gene encoded the yeast homologue of a mammalian protein associated with the 26S proteasome. This mammalian protein known as TRAP-2 and as the "p97" protein was first purified by DeMartino and colleagues as part of the PA700 complex, a complex which associates with the core 20S proteasomal particle. The association of the PA700 complex with the 20S proteasome particle results in the formation of a 26S particle which is proposed to be the mature 26S proteasome. Hrd2p was also significantly homologous, albeit to a much lesser extent, to the yeast Sem3p protein. Sem3p has recently been shown to be a distinct component of the yeast 26S proteasome, corresponding to the "p112" protein of the PA700 complex (DeMarini et al., Mol Cell Biol 15: 6311–21, 1995). Consistent with these sequence similarities, the hrd2-1 mutants had numerous phenotypes consistent with a deficiency in proteasomal function including: slow growth, canavanine sensitivity, a global increase of ubiquitin-conjugated proteins, and implementation by the human homologue TRAP-2. Furthermore, a hrd2::URA3 null allele caused lethality, indicating that the HRD3 gene was essential for viability in at least some strains. The most straightforward interpretation of these data was that the proteasome plays a role in the degradation of the Hmg2p protein and of related substrates, such as the unregulated 6myc-Hmg2p substrate. The data on hrd2-2 mutant also lend in vivo support to the hypothesis that the PA700 complex is important in the global functions of the 26S proteasome.

The identity of the Hrd2p protein as a proteasomal activator implied that the proteasome was involved in the degradation of HMG-R in yeast. These data provided a genetic counterpart to the biochemical studies implicating the proteasome in the ER degradation of the integral membrane protein CFTR and it clinically important Δ508 variant (Jensen et al., Cell 83: 129–35, 1995; Ward et al., Cell 83: 121–7, 1995). Moreover, our data indicated that the proteasome may play a broader role in the degradation of membrane proteins of the ER, and possibly those of other cellular compartments as well. Previous studies on mammalian cells have shown that the degradation of mammalian HMG-R is inhibited by the peptidyl-aldehyde ALLN (Inoue et al., J Biol Chem 266: 13311–7, 1991; Lecureux and Wattenberg, Gene 158: 113–7, 1994). Originally this inhibition was interpreted to mean that HMG-R degradation included the action of a cysteine protease. However, this agent is also a potent inhibitor of the proteasome (Jensen et al., Cell 83: 129–35, 1995). New studies with other inhibitors, as well as in vitro biochemical approaches, now indicate that inhibition of mammalian HMG-R degradation by ALLN may in fact be due to its actions on the proteasome (R. Simoni, personal communication).

In contrast to HRD2, the HRD1 and HRD3 genes each encode proteins that have no other known biochemical functions. Furthermore, none of the hrd1 and hrd3 mutants had any of the pleiotropic phenotypes associated with the hrd2-1 mutant, and with many other protein degradation mutants. However, mutants defective in HRD1 or HRD3 are phenotypically stronger than the hrd2-1 mutant at stabilizing Hmg2p, in spite of the lack of other phenotypes. Presumably, the Hrd1p and Hrd3p proteins have fewer functions than the globally employed Hrd2p proteasomal subunit. Perhaps they act at an early or specific step in the delivery of the Hmg2p protein to the 26S proteasome. Alternatively, they may be involved in a separate degradation pathway for Hmg2p that is more specific for this class of substrates. The prevalence of the proteasome in degradation processes favors the former model. Since both Hrd1p and Hrd3p appear to be membrane proteins, their possible functions could include recruitment of Hmg2p to the degradation pathway, removal of Hmg2p from the ER membrane, or assembly of a degradation complex includes a subset of 26S proteasomes bound to the ER membrane. However, the observation that the disruption of the HRD1 gene appeared to cause transient problems in haploid survival may mean that the HRD1 gene has broader cellular functions than the HRD3 gene.

The C-terminal region of the predicted Hrd1p contained a member of the motif class called an "H2 ring finger" based upon both the order and distance of the cysteine and histidine residues and the flanking amino acids (Freemont, *Ann N Y Acad Sci* 684: 174–92, 1993). Although the function of the H2 ring finger is not known, it has been proposed to bind $Zn^{+2}$ ions, and may be involved in the interaction of the "ringed" protein with other proteins. Interestingly, this particular class of ring fingers is most common in membrane proteins, and the H2 variant of the ring finger is more likely to be found in the C-terminal region of such proteins. The role of the Hrd1p ring finger motif is under study, with a goal of identifying the other proteins that might interact with Hrd1p through this conserved region.

The most obvious feature of the Hrd3p protein is that the majority of the sequence is predicted to be in the lumen of a membrane-bound compartment, presumably the ER, and not in the cytosol where the 26S proteasome is found. In this sense, Hrd3p is reminiscent of the US 11 protein of human cytomegalovirus. US11 appears to function in the degradation of unloaded (ER localized) MHC-I molecules by causing their "retrotranslocation" out of the ER membrane and into the cytosol for degradation by the proteasome (Wiertz et al., *Cell* 84: 769–779, 1996). Since the degradation of HMG-R appears to be a progressive process, a similar function may be required for the presentation of polytropic substrates such as HMG-R to the cytosolic 26S proteasome. Parallel studies on the degradation of soluble proteins of the ER lumen have hinted that the proteasome may also be involved in the degradation of those proteins as well, and some evidence supporting retrotranslocation to the cytosol has been provided for this class of substrates (McCracken and Brodsky, *J Cell Biol* 132: 291–298, 1996). Thus, it may be that the movement of peptide sequences, either as part of polytropic membrane proteins or as free lumenal proteins, from protected lumenal regions to the cytosolic proteasome is a common theme in the ER degradation of a disparate set of proteins.

2. Hrd3p homologues and the "HRD3" motif

The Hrd1p and Hrd3p proteins are not full length homologues of a well-studied protein, as is Hrd2p. However, the Hrd3p protein contains a region homologous to numerous proteins. The most homologous portion of HRD3 is in the region of a 625–666. This sequence has significant homology to regions of human, *C. elegans* and *S. pombe* proteins in the public databases (FIG. 9). Furthermore, this region of Hrd3p also has homology to a more N-terminal portion of the Hrd3p protein itself, implying that the evolution of the modern sequence might have included an ancient duplication of the conserved motif. The *C. elegans* protein sel-1 is the highest scoring Hrd3p orthologue in the database. The overall identity of sel-1 and Hrd3p is ~20%, with regions that are much higher (FIG. 9). The predicted sel-1 protein also appears to have a similarly duplicated region, as well as regions of homology to Hrd3p outside the duplicated motif. Unlike the Hrd3p peptide, the sel-1 protein has no C-terminal transmembrane region, but rather resembles a version of the Hrd3p protein that is terminated before the transmembrane span. The first 80 amino acids of the sel-1 protein encode a function signal sequence. Based on these features, the sel-1 protein was predicted to be extracellular (Grant and Greenwald, *Genetics* 143:237–247, 1996). However, sel-1 may be associated with intracellular vesicles (B. Grant and I. Greenwald, *Genetics* 143:237–247.

There is also a homologue of Hrd3p in yeast itself, called Skt5p. Although significantly less similar to the Hrd3p protein than sel-1, the characteristic "Hrd3p motif" is present, and an ancient duplication of the motif is present in a more N-terminal part of the molecule protein, as in sel-1 and Hrd3p. Furthermore, it appears that the Skt5p C-terminus has a farnesylation site. Thus, the Hrd3p and Skt5p proteins appear to have distinct, familiar features that allow membrane association, i.e., a transmembrane span or a farnesylation site, respectively. Perhaps the conserved function(s) of the "Hrd3 motif" somehow require proximity of the C-terminus to a membrane, as promoted by each of these distinct C-termini.

Although none of the proteins with homologies to Hrd3p have a well understood function, sel-1 mutants have some suggestive phenotypes. sel-1 was isolated as a suppressor of a hypomorphic mutation in the lin-12 -encoded transmembrane receptor. The same sel-1 mutation also partly relieves the phenotype of a hypomorphic mutation in the related, but distinct, glp-1 -encoded transmembrane receptor. The original sel-1 mutation appears to be a null allele. Accordingly, the sel-1 protein is described as a negative regulator of each of these receptors since less sel-1 activity results in more lin-2 and more glp-1 signals from the mutant proteins. Importantly, the sel-1 mutation cannot bypass null mutations of either lin-12 or glp-1. Furthermore, the sel-1 mutation has no phenotype in worms with wild-type lin-12 and glp-1 genes. It may be that the sel-1 protein is involved in the degradation of hypomorphic lin-12 and glp-1 proteins. In this way, the loss of sel-1 function might suppress the mutant phenotypes by allowing elevated levels of the degraded mutant receptors much as hrd3 mutants increase the level of Hmg2p. However, it is certainly possible that the homology is due to shared motifs that function in very distinct ways.

3. HRD genes and the mevalonate pathway

The HRD selection presented herein relied on the use of a variant of Hmg2p whose half-life was not affected by alterations of the mevalonate pathway. Nevertheless, the resulting mutants all stabilized normal Hmg2p. Thus, the HRD-gene encoded degradation process cannot distinguish between regulated and unregulated degradation substrates. In contrast, alteration of the mevalonate pathway only affects the degradation of normal Hmg2p and some variations of Hmg2p, such as Hmg2p-GFP, but not 6myc-Hmg2p (Hampton et al., *Proc. Natl. Acad. Sci. USA.* 93: 828–833, 1996). Clearly, the regulation of Hmg2p degradation by the mevalonate pathway cannot occur by simply altering the action of one or more Hrd proteins. If this were the mechanism, then any protein degraded by the actions of the Hrd proteins would be regulated by the mevalonate pathway. In fact, only a subset are regulated, such as Hmg2p and Hmg2p-GFP. Therefore, these data indicated that the regulation of Hmg2p degradation by the mevalonate pathway occurs by altering the susceptibility of a regulated protein to degradation by the HRD-encoded machinery.

All publications and patent applications cited in this specification are herein incorporated by reference for all purposes as if each individual publication or patent application were specifically and individually indicated to be incorporated by reference in their entirety for all purposes.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide having an amino acid sequence selected from the group consisting of SEQ ID NO:8, conservatively modified SEQ ID NO:8, SEQ ID NO:25, and conservatively modified SEQ ID NO:25.

2. The isolated polypeptide of claim 1, wherein said polypeptide is encoded SEQ ID NO:7.

3. An isolated polypeptide encoded by a vector comprising a nucleic acid which hybridizes under highly stringent conditions to a nucleic acid which encodes a polypeptide selected from the group consisting of SEQ ID NO:8, conservatively modified SEQ ID NO:8, SEQ ID NO:25, and conservatively modified SEQ ID NO:25.

4. The isolated polypeptide of claim 1, wherein said polypeptide has the amino acid sequence of SEQ ID NO:8.

5. The isolated polypeptide of claim 1, wherein said polypeptide has the amino acid sequence of SEQ ID NO:25.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
       (A) LENGTH: 4982 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:1:

```
TAGCCAAGGC CAGTTGATTG ATTTAGCCAC AAGTATCATT CAACGTAATA TCCACAGGTG      60
TTTTTTTTCT CACCGGAAGG CGAATAAAAT ACAGGAGCTA GAGCGTGTAA GATAATGAAC     120
AAGGAATCTA AAGATGATGA TATGTCCTTG GGGAAGTTTT CCTTCTCCCA CTTCCTATAT     180
TACTTGGTGC TAATAGTAGT AATAGTGTAC GGTTTGTACA AGCTTTTCAC TGGACATGGA     240
TCCGACATTA ATTTCGGGAA GTTCTTGTTA AGGACATCCC CTTATATGTG GGCCAATCTT     300
GGTATTGCCC TTTGTGTAGG CTTAAGTGTC GTGGGGCAG CATGGGGTAT TTTCATTACT      360
GGTTCATCCA TGATTGGTGC CGGTGTGCGT GCTCCAAGGA TTACCACCAA GAATTTAATT     420
TCCATTATTT TCTGTGAAGT GGTTGCCATT TACGGTCTGA TTATTGCCAT TGTCTTTTCT     480
TCGAAATTGA CTGTGGCTAC TGCTGAGAAC ATGTACTCGA AATCAAACCT GTACACTGGT     540
TATTCTCTTT TCTGGGCAGG TATCACTGTC GGTGCTTCCA ATTTGATTTG TGGTATCGCT     600
GTCGGTATCA CCGGTGCGAC TGCTGCCATT TCCGATGCTG CTGATTCCGC ATTGTTTGTT     660
AAAATTTTGG TCATTGAAAT TTTCGGGTCC ATTTTAGGTT TATTAGGTTT GATTGTTGGT     720
TTATTGATGG CCGGTAAAGC TTCTGAATTT CAGTAAGCGC TCAAACCAGG CTTTTCTTTT     780
CCGTTTTTAC GAGCTAGATA AGCGCATCCA TATTTACTAA TAGATATAAT GAGATATCTG     840
AGATACATGT GTATGTATAT ATGCACGTTT TCTTTTATTA TCTAAAAATC ATATTATATT     900
AAGTAAGAGA AAAAAATGTA CAACTATATA AATATATATT TATTTAAAAT GGTTTTGAAT     960
TTTTCCTATT CTGGTTGATA TTGCCCAAAA GCTATTCAGT TTACTCCTCT TCACGATAGT    1020
CAGGGTTCTT CTTTAAAATT ACTACGCCCT CAATATGGCT TGTGTAACTA ATATATTCAT    1080
CAGTTTCTAG TTCTGCTCTT TCGCCATGAT TTAGTAAAAC AGGAGTGGAT TGCGTAATCC    1140
AGCCAGTAAT CTTTTTTGGT CTGCCTGCTT GGCCGACAGT TTCCACTGCT TGACCAACGC    1200
GCACATTAAC CTTTATTGGC TCTCCCTCAT CGTTTAATGC TAGAATAAAC TTTGGCCTTA    1260
TACCGGCATT CAACATGTAG AACAATTGAT GATGCTTCAA CATGAAACTT GGCGATACTA    1320
AACCAACTGC GGTAGTTAAT ATTGATGCTA ATGTCACCTT ATTCAAAACA TGTGCATCAT    1380
TGAACACATC CATTGTCATA GTACCTTTAC CAAGATGCAA TAACCCTTGT GCTAATCTGG    1440
TGATAAACAA AGCGTCTTGT TCACGTGAAT AATAACTTGC CAACTGTCTT AATAGTTGAG    1500
CTAACCTTGC ATTGTTAGTA CCAGCACCAC ATAGACCCAT AGCGAAAATT GAATTCATTG    1560
AAACTTCTAA ATCGGCGTCA TGTGAAAAAC GAGTTAAGGT ATCGAACACC TTCATTTGTG    1620
GATCAGAAAC GGAAACAATA CCCATCGCTA AGGAACCAT ACGACGGATG TGTTCATTAC     1680
CATAATGCAT TAAATGACCA AAATGACGTA AAGACATTTC CTTGCCAATA TCTTCACCAA    1740
GGGCAATCAA AGCAATACCC AAAACTGCAT AAGCAAGTTC ATCGACTATG CCTGCTTCTT    1800
```

```
TTTCTTCCTC CTCATCATCA TTTTTCCCGT CCGTAGTAGC ATCCTTATCG GAAGATTTTC    1860

CCTTCTTTTC TTCGGATTTT ATCTCTTCAC CTTCTAAACT CTCACCATTC TTCTTCTCTG    1920

TTATTTCTGC TTTAACTTCA ACTTCCTCTC CTTCGGCATC AACCTCCATT TCGTCCACTT    1980

CGATCTCAGC TTCCTCGTTC TTGGTAGGTT CATTCACTTG CTCACCCAAA AAGTCACTTA    2040

TGCTATTAGT CTGTCCTTCG GCAGTTTCTT CTTCATCTGC ATCTTCTTCA CCTTTTACGT    2100

TTTTAGGGGT CAAACGATGT AACAAATCTT GAATTAACAA ACATCACCC GTACCAGTAT     2160

AAGCACATGA ACCAACTAAT ACTTCAATAG CTGATGTCAT TGGATGTTCA ATAGCACTAA    2220

TAGTTTCTAA AACATCATCC ACCTGTTCAC CTTGGCCCAT GTATAGAATA CCTAAAGCAA    2280

GTGCCAAAAA CCTTACCCAG TCGGTCTTCA ACTCGATGGC TGTACGCTCT AAAAAGTTGT    2340

CCATGATAGA AGTTGTAATG TCACCATTAC AAGTACCAAC GAAAACATGA GCCAAAGCTA    2400

AGGAAGCCAT AGCTGCAGTT TCAATAGGCA AGTCAGTGGA TGCGGCAATT GGTAATAACA    2460

AACCCAACAC TTCGTCATTC TTGCTACCAG CAAATGCAAT ACCCAGGCCA AGAATAGCTG    2520

CTGAACTAAT TTTAGTGTCT GGGTTAGTAA CATAATCTTG CAAAAGTAAC AAAGCTGGTT    2580

CAACTTCACC ATCATGCACA CCGGAAGCGG AAATACCAAT ACCTAATAAT GCACCAGCTT    2640

TAACTTCTGG CTCATCAACG TAGAGATACT TATCCAGTTG TTGCAAACCA TCGAGATTCC    2700

ACTGGTATAT AGATCCAATA CTAGCTACCG CGGAAGTCAT ACCGTCACCT TTGGTTTTAT    2760

ATACCCAATT ATCATTATCC ACAATTAATT TATCGTTACA ATAACCTAAG TTTAAGAACC    2820

CGTTGACAAA TGACGAAGCT AGATTTTGTT GAGCAGAATC TAGGCCGGCG CTTGAGAACA    2880

CAGATTTAGA GTTATCCAAA TGGCTCTTAT AAATGTCTTC TGGGACTTTT GGCCCAGTTA    2940

GATTCAATTC TTTAGCAAGA TATAAAAAGT GTTCAGACAA TTTACCATTT CCAATTATAT    3000

CCTGAACACC TTCATACTCA AACGATGTCT TTTGTGCGGC TAAAATATAT GCTAATTGTT    3060

TATGCATCAC TGGATCGCTA GTAGCATCGA AAACGGATCT GATCATATCC TCTTCCCCTA    3120

GTCTAACTGC CAAAGCAATT GCATCTGTAA GTTCGTTCTG AGATAGATAA ATAGAATATG    3180

CGGTTTTTAA AAAGGCAACG TCTTCAGGAG GTGGCAAAAG TGGAACACAT GCAACCTAT     3240

ATTGACAAAC TCTTTGGAAG GTATTCTCAT CGACAAATTG AGGTAGCTTG TCAATAGATT    3300

CAATTTCCAA AAGCAAATCT ACCGCGTCTT CTTCACCGTT GTGTTTCAAA AGTATGGGA    3360

CAATGTCTAA ACATAGACGA AGAGTATCTT CCTTGGAAAA TTCGAACCCG GAAGTAGCCG    3420

CAGATCCATC GCTTTTAGAT CCATCAGATG ATGTTTCATC TTCAGCATCT TTTTCCACTT    3480

GATCATTATA TACTTCACCG ATCTCCAAAG CTAAATGACG GATGTACTCA TGTCCCCACC    3540

CTTCAAAATC AGAAACGTCG GAGAGTAATC TATATCTCAA TGAATCGTGT TTACCATTTT    3600

CAGAGTATGT CATGGCTAAA ATGGACAAGA CATCCGCTAA AGAGGATTTC AAGTTTGGAT    3660

CTGTCCATTT GTCGTAGATA GAACATAGGT CTGGATATGT CGGACGAAGG AATTTCAAAG    3720

GTTTGGGAAC GGCGGTCATA GAACTCGTAG AATTTTTGAT CGATTCCTTT AAGGCATTCA    3780

AAGACGCTTC ATATAAAGAT GAATCGTCTT CTTTCAGCCT TTCAACCAAT AGCTCTAAAT    3840

CTGTTTTAAG CTTTGCATCT TCTTCGGATA GCTGCTCCTC TTCCTCCTTT TTTTTATCCT    3900

TCTTATTTGG TGTCTGCTTT TCAGGACTTA TCTGCGATTG TTCATCAATA GTCTGTTGTT    3960

TCTTATCACT TTCGTCTACC ATTTTCTTGC AATTGTCTTC CAAATTTATA CGAATCGCAC    4020

CTTATGTAGA CCAATGGGCA AGTTTGTTAG TGAAGAATTA TAGATTTGAC CAAATTTGCT    4080

TAATTACTTA TACCCTTTGC CAAATTTCGT GCTCGCCTTT TGCCACCGTA AAACACATCA    4140

TCTTCTACGA ACATTAATCT GTTATATTAC CAATTTTATA TATACATAGT ATGTAAATAT    4200
```

-continued

```
GAAAATGTTT TATGAATGTC TCTATGAGAT GAGCTGTAAA TAGTCAACTC ATTTGACAAA      4260

TTGCCCATCG AAAGCACGCT TGCCCAATC CAATAGCTTG TCAAAAACGA TTACATTCGC       4320

ATTATGGTAT CTTATACTAT GATCTGAGTC AGGAAAGACG TGGACGTCAT AATTTTCCAC      4380

ACCATTTAGA TCCAAAAGGT CCAGAAACTT TAGGGAATTT TGAAAGTGAA CGTTATCATC      4440

TCCTGTTCCG TGCATCAACA AAAATCTATT TGCTTGTGCC AAAGCAGTGA CATTATGAAC      4500

GCTTGATTCT ACGTATCCAT CAAAGTTTTC TTGAGGAGTA TGCATGTACC TCTCAGTATA      4560

AACAGAATCG TAAAATCTCC AGTCGGTTAC TGGCGCAACT GACATCCCGT ATTTGAAATG      4620

TCTTCCGCCA TCTTTCTCCA AAGTTTTTAG TGTCAGGTAC CCCCCGTATG ACCAACCAAA      4680

TAAGGAAATC TTTTGCGGAT CAACAAAAGT TAAAGAACCA TATAAGGAAG CCGCAGATAT      4740

TTGGTCGCGG GCCTCGTAAT CACCGAGCCT ATCGCGAACA AGGGATCTAA AGTCTTGACC      4800

TTTGAAGCCA GTACCACGAC CGTCAACAAC AACTACAATT GCGTTTAATT GTGAAGCTAC      4860

CACTTCATTA AATCCTACGG AAAACGTTTT GACAACTTGT TGAGAATTCG GTCCCCCATA     4920

TGCAAAGAAA AATACAGGAT AGTGGTCACT TAACGTTTCA TCGAAATCAT TTGGTAGGAT      4980

TT                                                                    4982
```

(2) INFORMATION FOR SEQ ID NO:2:

(i) SEQUENCE CHARACTERISTICS:
        (A) LENGTH: 2499 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

```
ATGATAACAC TCTTATTATA CCTGTGCGTA ATATGTAACG CAATAGTGTT AATAAGGGCT       60

GATTCGATAG CGGACCCTTG GCCTGAAGCG CGACATCTAC TAAATACCAT AGCTAAGTCC      120

AGAGACCCAA TGAAAGAAGC TGCTATGGAA CCCAATGCAG ATGAATTTGT TGGATTCTAT      180

GTACCGATGG ATTATTCCCC ACGTAATGAG GAAAAAAACT ACCAGAGCAT TTGGCAAAAC      240

GAAATCACAG ATTCTCAACG TCATATTTAT GAATTACTTG TACAATCAAG TGAACAATTC      300

AACAACTCAG AAGCAACATA TACACTTAGC CAGATTCACC TTTGGAGTCA ATATAATTTC      360

CCGCATAATA TGACTTTGGC ACACAAATAC TTAGAAAAAT TCAATGATCT AACCCACTTC      420

ACCAATCATT CGGCCATCTT CGACTTAGCT GTGATGTATG CCACTGGGGG ATGTGCTTCT      480

GGTAATGATC AAACCGTGAT CCCTCAGGAT TCTGCTAAAG CACTGCTATA TTACCAAAGG      540

GCTGCCCAAC TAGGGAATTT AAAGGCTAAG CAAGTGCTAG CTTATAAATA CTATTCTGGC      600

TTCAATGTCC CACGAAATTT TCATAAATCT TTAGTATTGT ACAGGGACAT TGCTGAACAG      660

CTGAGAAAGT CGTACTCCAG GGACGAATGG GATATTGTCT TCCCCTATTG GGAAAGTTAC      720

AACGTGAGAA TATCGGATTT TGAGAGTGGC CTATTAGGTA AAGGTTTGAA TTCCGTTCCA      780

TCTTCTACAG TAAGGAAAAG AACTACGAGA CCAGATATTG GTTCACCCTT TATTGCGCAA      840

GTTAACGGTG TACAGATGAC CTTGCAAATC GAACCGATGG GTAGGTTCGC TTTCAACGGT      900

AACGATGGCA ACATAAATGG CGACGAAGAT GACGAGGATG CCAGTGAAAG ACGAATCATT      960

CGGATATATT ATGCAGCTTT GAATGATTAT AAAGGAACAT ATTCACAAAG CAGAAATTGT     1020

GAGCGCGCCA AAAACTTGTT GGAATTAACG TACAAGGAAT TCAGCCTCA TGTCGACAAT      1080

TTGGATCCTT TGCAAGTATT TTACTACGTC CGTTGCTTAC AATTATTGGG GCACATGTAT     1140

TTCACCGGCG AAGGCTCCTC GAAGCCTAAT ATTCATATGG CCGAAGAGAT CCTGACCACG     1200
```

-continued

```
TCGCTAGAAA TAAGCAGAAG GGCACAGGGA CCTATAGGTA GAGCGTGCAT AGATCTGGGC    1260

TTAATAAATC AATACATCAC AAACAATATT TCTCAAGCAA TTTCGTATTA TATGAAAGCT    1320

ATGAAAACAC AAGCTAACAA TGGAATCGTA GAATTCCAAT TATCCAAATT GGCCACTTCA    1380

TTCCCTGAAG AAAAAATCGG CGACCCATTT AACTTAATGG AAACTGCCTA CTTGAATGGA    1440

TTCATTCCAG CCATATATGA GTTTGCAGTA ATGATCGAAT CTGGAATGAA CAGTAAGAGT    1500

AGTGTGGAAA ACACTGCTTA CCTGTTCAAA ACATTCGTTG ACAAAAACGA AGCTATTATG    1560

GCACCTAAAC TGAGGACAGC ATTTGCCGCA TTAATCAACG ATCGTTCAGA AGTGGCTTTA    1620

TGGGCTTATT CCCAACTAGC CGAGCAAGGC TACGAGACTG CTCAAGTCTC TGCCGCCTAC    1680

TTAATGTACC AGTTGCCATA TGAGTTTGAG GATCCTCCAA GAACCACAGA TCAGAGAAAA    1740

ACTTTGGCAA TTTCCTACTA TACAAGAGCG TTTAAACAGG GAAATATAGA TGCTGGTGTT    1800

GTCGCGGGAG ATATCTATTT TCAGATGCAG AATTACAGTA AAGCTATGGC TCTTTATCAG    1860

GGTGCAGCTT TGAAGTACTC TATACAGGCT ATCTGGAACT TAGGGTACAT GCATGAGCAT    1920

GGGCTAGGTG TAAACAGAGA TTTCCATCTT GCTAAACGTT ACTACGACCA AGTTTCAGAA    1980

CACGATCATA GATTTTACTT GGCTTCCAAA TTGAGTGTTT TAAAATTACA CCTAAAGTCA    2040

TGGTTGACTT GGATCACCAG AGAAAAAGTA AACTACTGGA AACCTTCCTC GCCACTTAAC    2100

CCTAACGAAG ATACTCAGCA CTCGAAGACT TCATGGTACA AGCAATTGAC GAAGATTCTA    2160

CAAAGAATGA GACATAAGGA GGATAGTGAC AAAGCTGCGG AAGATTCTCA CAAACACAGA    2220

ACTGTAGTGC AGAATGGAGC TAACCATAGG GGTGACGACC AAGAGGAGGC TTCCGAGATT    2280

TTGGGCTTCC AAATGGAGGA TCTTGTTACG ATGGGATGTA TCTTGGGGAT ATTCCTATTA    2340

AGTATATTAA TGAGTACACT GGCGGCCCGT AGAGGCTGGA ATGTCCGTTT CAATGGAGCA    2400

CAATTAAATG CAAATGGTAA CCGGCAGCAA GAGCAACAAC AACAACAACA AGCACAAGGT    2460

CCCCCGGGCT GGGACTTCAA TGTTCAGATA TTCGCCATA                          2499
```

(2) INFORMATION FOR SEQ ID NO:3:

(i) SEQUENCE CHARACTERISTICS:
        (A) LENGTH: 994 amino acids
        (B) TYPE: amino acid
        (D) TOPOLOGY: linear (ii) MOLECULE TYPE: protein (xi) SEQUENCE DESCRIPTION: SEQ ID NO:3:

```
Met Val Asp Glu Ser Asp Lys Lys Gln Gln Thr Ile Asp Glu Gln Ser
 1               5                  10                  15

Gln Ile Ser Pro Glu Lys Gln Thr Pro Asn Lys Asp Lys Lys Lys
            20                  25                  30

Glu Glu Glu Glu Gln Leu Ser Glu Glu Asp Ala Lys Leu Lys Thr Asp
        35                  40                  45

Leu Glu Leu Leu Val Glu Arg Leu Lys Glu Asp Asp Ser Ser Leu Tyr
    50                  55                  60

Glu Ala Ser Leu Asn Ala Leu Lys Glu Ser Ile Lys Asn Ser Thr Ser
65                  70                  75                  80

Ser Met Thr Ala Val Pro Lys Pro Leu Lys Phe Leu Arg Pro Thr Tyr
                85                  90                  95

Pro Asp Leu Cys Ser Ile Tyr Asp Lys Trp Thr Asp Pro Asn Leu Lys
            100                 105                 110

Ser Ser Leu Ala Asp Val Leu Ser Ile Leu Ala Met Thr Tyr Ser Glu
        115                 120                 125
```

-continued

```
Asn Gly Lys His Asp Ser Leu Arg Tyr Arg Leu Leu Ser Asp Val Ser
    130                 135                 140
Asp Phe Glu Gly Trp Gly His Glu Tyr Ile Arg His Leu Ala Leu Glu
145                 150                 155                 160
Ile Gly Glu Val Tyr Asn Asp Gln Val Glu Lys Asp Ala Glu Asp Glu
                165                 170                 175
Thr Ser Ser Asp Gly Ser Lys Ser Asp Gly Ser Ala Ala Thr Ser Gly
            180                 185                 190
Phe Glu Phe Ser Lys Glu Asp Thr Leu Arg Leu Cys Leu Asp Ile Val
        195                 200                 205
Pro Tyr Phe Leu Lys His Asn Gly Glu Glu Asp Ala Val Asp Leu Leu
    210                 215                 220
Leu Glu Ile Glu Ser Ile Asp Lys Leu Pro Gln Phe Val Asp Glu Asn
225                 230                 235                 240
Thr Phe Gln Arg Val Cys Gln Tyr Met Val Ala Cys Val Pro Leu Leu
                245                 250                 255
Pro Pro Pro Glu Asp Val Ala Phe Leu Lys Thr Ala Tyr Ser Ile Tyr
            260                 265                 270
Leu Ser Gln Asn Glu Leu Thr Asp Ala Ile Ala Leu Ala Val Arg Leu
        275                 280                 285
Gly Glu Glu Asp Met Ile Arg Ser Val Phe Asp Ala Thr Ser Asp Pro
    290                 295                 300
Val Met His Lys Gln Leu Ala Tyr Ile Leu Ala Ala Gln Lys Thr Ser
305                 310                 315                 320
Phe Glu Tyr Glu Gly Val Gln Asp Ile Ile Gly Asn Gly Lys Leu Ser
                325                 330                 335
Glu His Phe Leu Tyr Leu Ala Lys Glu Leu Asn Leu Thr Gly Pro Lys
            340                 345                 350
Val Pro Glu Asp Ile Tyr Lys Ser His Leu Asp Asn Ser Lys Ser Val
        355                 360                 365
Phe Ser Ser Ala Gly Leu Asp Ser Ala Gln Gln Asn Leu Ala Ser Ser
    370                 375                 380
Phe Val Asn Gly Phe Leu Asn Leu Gly Tyr Cys Asn Asp Lys Leu Ile
385                 390                 395                 400
Val Asp Asn Asp Asn Trp Val Tyr Lys Thr Lys Gly Asp Gly Met Thr
                405                 410                 415
Ser Ala Val Ala Ser Ile Gly Ser Ile Tyr Gln Trp Asn Leu Asp Gly
            420                 425                 430
Leu Gln Gln Leu Asp Lys Tyr Leu Tyr Val Asp Glu Pro Glu Val Lys
        435                 440                 445
Ala Gly Ala Leu Leu Gly Ile Gly Ile Ser Ala Ser Gly Val His Asp
    450                 455                 460
Gly Glu Val Glu Pro Ala Leu Leu Leu Leu Gln Asp Tyr Val Thr Asn
465                 470                 475                 480
Pro Asp Thr Lys Ile Ser Ser Ala Ala Ile Leu Gly Leu Gly Ile Ala
                485                 490                 495
Phe Ala Gly Ser Lys Asn Asp Glu Val Leu Gly Leu Leu Pro Ile
            500                 505                 510
Ala Ala Ser Thr Asp Leu Pro Ile Glu Thr Ala Ala Met Ala Ser Leu
        515                 520                 525
Ala Leu Ala His Val Phe Val Gly Thr Cys Asn Gly Asp Ile Thr Thr
    530                 535                 540
Ser Ile Met Asp Asn Phe Leu Glu Arg Thr Ala Ile Glu Leu Lys Thr
```

-continued

```
            545                 550                 555                 560
Asp Trp Val Arg Phe Leu Ala Leu Ala Leu Gly Ile Leu Tyr Met Gly
                565                 570                 575
Gln Gly Glu Gln Val Asp Asp Val Leu Glu Thr Ile Ser Ala Ile Glu
            580                 585                 590
His Pro Met Thr Ser Ala Ile Glu Val Leu Val Gly Ser Cys Ala Tyr
        595                 600                 605
Thr Gly Thr Gly Asp Val Leu Leu Ile Gln Asp Leu Leu His Arg Leu
    610                 615                 620
Thr Pro Lys Asn Val Lys Gly Glu Glu Asp Ala Asp Glu Glu Glu Thr
625                 630                 635                 640
Ala Glu Gly Gln Thr Asn Ser Ile Ser Asp Phe Leu Gly Glu Gln Val
                645                 650                 655
Asn Glu Pro Thr Lys Asn Glu Glu Ala Glu Ile Glu Val Asp Glu Met
            660                 665                 670
Glu Val Asp Ala Glu Gly Glu Glu Val Glu Val Lys Ala Glu Ile Thr
        675                 680                 685
Glu Lys Lys Asn Gly Glu Ser Leu Glu Gly Glu Ile Lys Ser Glu
    690                 695                 700
Glu Lys Lys Gly Lys Ser Ser Asp Lys Asp Ala Thr Thr Asp Gly Lys
705                 710                 715                 720
Asn Asp Asp Glu Glu Glu Lys Glu Ala Gly Ile Val Asp Glu Leu
                725                 730                 735
Ala Tyr Ala Val Leu Gly Ile Ala Leu Ile Ala Leu Gly Glu Asp Ile
            740                 745                 750
Gly Lys Glu Met Ser Leu Arg His Phe Gly His Leu Met His Tyr Gly
        755                 760                 765
Asn Glu His Ile Arg Arg Met Val Pro Leu Ala Met Gly Ile Val Ser
    770                 775                 780
Val Ser Asp Pro Gln Met Lys Val Phe Asp Thr Leu Thr Arg Phe Ser
785                 790                 795                 800
His Asp Ala Asp Leu Glu Val Ser Met Asn Ser Ile Phe Ala Met Gly
                805                 810                 815
Leu Cys Gly Ala Gly Thr Asn Asn Ala Arg Leu Ala Gln Leu Leu Arg
            820                 825                 830
Gln Leu Ala Ser Tyr Tyr Ser Arg Glu Gln Asp Ala Leu Phe Ile Thr
        835                 840                 845
Arg Leu Ala Gln Gly Leu Leu His Leu Gly Lys Gly Thr Met Thr Met
    850                 855                 860
Asp Val Phe Asn Asp Ala His Val Leu Asn Lys Val Thr Leu Ala Ser
865                 870                 875                 880
Ile Leu Thr Thr Ala Val Gly Leu Val Ser Pro Ser Phe Met Leu Lys
                885                 890                 895
His His Gln Leu Phe Tyr Met Leu Asn Ala Gly Ile Arg Pro Lys Phe
            900                 905                 910
Ile Leu Ala Leu Asn Asp Glu Gly Glu Pro Ile Lys Val Asn Val Arg
        915                 920                 925
Val Gly Gln Ala Val Glu Thr Val Gly Gln Ala Gly Arg Pro Lys Lys
    930                 935                 940
Ile Thr Gly Trp Ile Thr Gln Ser Thr Pro Val Leu Leu Asn His Gly
945                 950                 955                 960
Glu Arg Ala Glu Leu Glu Thr Asp Glu Tyr Ile Ser Tyr Thr Ser His
                965                 970                 975
```

-continued

```
Ile Glu Gly Val Val Ile Leu Lys Lys Asn Pro Asp Tyr Arg Glu Glu
            980                 985                 990

Glu Gln (2) INFORMATION FOR SEQ ID NO:4:

(i) SEQUENCE CHARACTERISTICS:
        (A) LENGTH: 833 amino acids
        (B) TYPE: amino acid
        (D) TOPOLOGY: linear (ii) MOLECULE TYPE: protein (xi) SEQUENCE DESCRIPTION: SEQ ID NO:4:

Met Ile Thr Leu Leu Leu Tyr Leu Cys Val Ile Cys Asn Ala Ile Val
  1               5                  10                  15

Leu Ile Arg Ala Asp Ser Ile Ala Asp Pro Trp Pro Glu Ala Arg His
                 20                  25                  30

Leu Leu Asn Thr Ile Ala Lys Ser Arg Asp Pro Met Lys Glu Ala Ala
             35                  40                  45

Met Glu Pro Asn Ala Asp Glu Phe Val Gly Phe Tyr Val Pro Met Asp
 50                  55                  60

Tyr Ser Pro Arg Asn Glu Glu Lys Asn Tyr Gln Ser Ile Trp Gln Asn
 65                  70                  75                  80

Glu Ile Thr Asp Ser Gln Arg His Ile Tyr Glu Leu Leu Val Gln Ser
                 85                  90                  95

Ser Glu Gln Phe Asn Asn Ser Glu Ala Thr Tyr Thr Leu Ser Gln Ile
                100                 105                 110

His Leu Trp Ser Gln Tyr Asn Phe Pro His Asn Met Thr Leu Ala His
            115                 120                 125

Lys Tyr Leu Glu Lys Phe Asn Asp Leu Thr His Phe Thr Asn His Ser
130                 135                 140

Ala Ile Phe Asp Leu Ala Val Met Tyr Ala Thr Gly Gly Cys Ala Ser
145                 150                 155                 160

Gly Asn Asp Gln Thr Val Ile Pro Gln Asp Ser Ala Lys Ala Leu Leu
                165                 170                 175

Tyr Tyr Gln Arg Ala Ala Gln Leu Gly Asn Leu Lys Ala Lys Gln Val
            180                 185                 190

Leu Ala Tyr Lys Tyr Tyr Ser Gly Phe Asn Val Pro Arg Asn Phe His
            195                 200                 205

Lys Ser Leu Val Leu Tyr Arg Asp Ile Ala Glu Gln Leu Arg Lys Ser
210                 215                 220

Tyr Ser Arg Asp Glu Trp Asp Ile Val Phe Pro Tyr Trp Glu Ser Tyr
225                 230                 235                 240

Asn Val Arg Ile Ser Asp Phe Glu Ser Gly Leu Leu Gly Lys Gly Leu
                245                 250                 255

Asn Ser Val Pro Ser Ser Thr Val Arg Lys Arg Thr Arg Pro Asp
            260                 265                 270

Ile Gly Ser Pro Phe Ile Ala Gln Val Asn Gly Val Gln Met Thr Leu
            275                 280                 285

Gln Ile Glu Pro Met Gly Arg Phe Ala Phe Asn Gly Asn Asp Gly Asn
290                 295                 300

Ile Asn Gly Asp Glu Asp Asp Glu Asp Ala Ser Glu Arg Arg Ile Ile
305                 310                 315                 320

Arg Ile Tyr Tyr Ala Ala Leu Asn Asp Tyr Lys Gly Thr Tyr Ser Gln
                325                 330                 335
```

```
Ser Arg Asn Cys Glu Arg Ala Lys Asn Leu Leu Glu Leu Thr Tyr Lys
        340                 345                 350

Glu Phe Gln Pro His Val Asp Asn Leu Asp Pro Leu Gln Val Phe Tyr
            355                 360                 365

Tyr Val Arg Cys Leu Gln Leu Leu Gly His Met Tyr Phe Thr Gly Glu
370                 375                 380

Gly Ser Ser Lys Pro Asn Ile His Met Ala Glu Glu Ile Leu Thr Thr
385                 390                 395                 400

Ser Leu Glu Ile Ser Arg Arg Ala Gln Gly Pro Ile Gly Arg Ala Cys
                405                 410                 415

Ile Asp Leu Gly Leu Ile Asn Gln Tyr Ile Thr Asn Asn Ile Ser Gln
                420                 425                 430

Ala Ile Ser Tyr Tyr Met Lys Ala Met Lys Thr Gln Ala Asn Asn Gly
            435                 440                 445

Ile Val Glu Phe Gln Leu Ser Lys Leu Ala Thr Ser Phe Pro Glu Glu
            450                 455                 460

Lys Ile Gly Asp Pro Phe Asn Leu Met Glu Thr Ala Tyr Leu Asn Gly
465                 470                 475                 480

Phe Ile Pro Ala Ile Tyr Glu Phe Ala Val Met Ile Glu Ser Gly Met
                485                 490                 495

Asn Ser Lys Ser Ser Val Glu Asn Thr Ala Tyr Leu Phe Lys Thr Phe
            500                 505                 510

Val Asp Lys Asn Glu Ala Ile Met Ala Pro Lys Leu Arg Thr Ala Phe
            515                 520                 525

Ala Ala Leu Ile Asn Asp Arg Ser Glu Val Ala Leu Trp Ala Tyr Ser
530                 535                 540

Gln Leu Ala Glu Gln Gly Tyr Glu Thr Ala Gln Val Ser Ala Ala Tyr
545                 550                 555                 560

Leu Met Tyr Gln Leu Pro Tyr Glu Phe Glu Asp Pro Pro Arg Thr Thr
                565                 570                 575

Asp Gln Arg Lys Thr Leu Ala Ile Ser Tyr Tyr Thr Arg Ala Phe Lys
            580                 585                 590

Gln Gly Asn Ile Asp Ala Gly Val Val Ala Gly Asp Ile Tyr Phe Gln
            595                 600                 605

Met Gln Asn Tyr Ser Lys Ala Met Ala Leu Tyr Gln Gly Ala Ala Leu
610                 615                 620

Lys Tyr Ser Ile Gln Ala Ile Trp Asn Leu Gly Tyr Met His Glu His
625                 630                 635                 640

Gly Leu Gly Val Asn Arg Asp Phe His Leu Ala Lys Arg Tyr Tyr Asp
                645                 650                 655

Gln Val Ser Glu His Asp His Arg Phe Tyr Leu Ala Ser Lys Leu Ser
            660                 665                 670

Val Leu Lys Leu His Leu Lys Ser Trp Leu Thr Trp Ile Thr Arg Glu
            675                 680                 685

Lys Val Asn Tyr Trp Lys Pro Ser Ser Pro Leu Asn Pro Asn Glu Asp
690                 695                 700

Thr Gln His Ser Lys Thr Ser Trp Tyr Lys Gln Leu Thr Lys Ile Leu
705                 710                 715                 720

Gln Arg Met Arg His Lys Glu Asp Ser Asp Lys Ala Ala Glu Asp Ser
                725                 730                 735

His Lys His Arg Thr Val Val Gln Asn Gly Ala Asn His Arg Gly Asp
            740                 745                 750

Asp Gln Glu Glu Ala Ser Glu Ile Leu Gly Phe Gln Met Glu Asp Leu
            755                 760                 765
```

```
Val Thr Met Gly Cys Ile Leu Gly Ile Phe Leu Leu Ser Ile Leu Met
    770                 775                 780

Ser Thr Leu Ala Ala Arg Arg Gly Trp Asn Val Arg Phe Asn Gly Ala
785                 790                 795                 800

Gln Leu Asn Ala Asn Gly Asn Arg Gln Gln Glu Gln Gln Gln Gln Gln
                805                 810                 815

Gln Ala Gln Gly Pro Pro Gly Trp Asp Phe Asn Val Gln Ile Phe Ala
            820                 825                 830

Ile
```

(2) INFORMATION FOR SEQ ID NO:5:

(i) SEQUENCE CHARACTERISTICS:
        (A) LENGTH: 274 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

```
TCGGACTACC GTTGGTTTCC ACAACTTCCT GGATTATCCT CGCCAAGGAC TTTGCAATAT    60
ATTTTTCCGC CTTTTCTGGA AGGATTTCGC TGCTTCCCGA AGTNCTTGGA CGAGCGCTCT   120
AGCTCTGTGG AAGGTTTTG GGCTCTCTGG CTCGGATTTT GCAATTTCTC CCTGGGGACT   180
GCCGTGGAGC CGCATCCACT GTGGATTATA ATTGCAACAT GACGCTGGAA GAGCTCGTGG   240
CGTGCGACAA CGCGGCGCAA GAAGATGCAG ACNG                              274
```

(2) INFORMATION FOR SEQ ID NO:6:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

```
GTTCCATTTC TATGGGTTTG GACACCGATG TAGATTATGA AACTGCATTT ATTCATTACC    60
GTCTGGCTTC TGAGCAGCAA CACAGTGCAC AAGCTATGTT TAATCTGGGA TATATGCATG   120
AGAAAGGACT GGGCATTAAA CAGGATATTC ACCTTGCGAA ACGTTTTTAT GACATGGCAG   180
CTGTAAGCCA GCCCAGATGC ACAAGTTCCA GTCTTCCTAG CCCTCTGCAA ATTGGGCATC   240
GTCTATTTCT TGCAGTACAT ACGGGAAACA AACATTGAG ATATGTTCTC CCAACTTGAT   300
ATGGACCAGC TTTTGGGACC TGAGTGGGAC CTTTACCTCA TGACCATCAT TGCGCTCTGT   360
TGGGAAGTCA TAGCTTACAG GCAAAGGCAG CACCAAGACA TGCCTGCACC CAGGCCTCCA   420
GGGCCACGGC CAGCTCCACC CCAGCAGGAG GGGCCACCAG AGCAGCAGCC ACCACAGTAA   480
TAGGCACTGG GTCCAGCCTT GATCAGTGAC AGCGAAGGAA GTTATCTGCT GGGAACACTT   540
GCATTTGATT TAGGACCTTG GGGATCCGAT G                                 571
```

(2) INFORMATION FOR SEQ ID NO:7:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

| | | | | | |
|---|---|---|---|---|---|
| ATGGTGCCAG | AAAATAGAAG | GAAACAGTTG | GCAATTTTTG | TAGTTGTCAC | ATATTTGCTC | 60 |
| ACATTTTATT | GCGTGTATTC | AGCCACCAAG | ACAAGCGTTT | CCTTTTTGCA | AGTAACACTG | 120 |
| AAGCTAAATG | AAGGCTTCAA | TCTAATGGTT | TTGTCGATAT | TCATCTTATT | AAATTCTACC | 180 |
| TTACTATGGC | AACTCCTAAC | GAAACTATTA | TTTGGTGAAC | TGAGGCTTAT | TGAGCATGAG | 240 |
| CACATTTTTG | AAAGGTTACC | ATTTACCATT | ATAAACACCT | TGTTTATGTC | CTCACTGTTC | 300 |
| CACGAACGGT | ATTTTTTCAC | AGTGGCATTT | TTTGGACTAT | TACTACTCTA | TCTGAAAGTT | 360 |
| TTCCATTGGA | TTTTAAAGGA | TAGGCTGGAG | GCCTTATTAC | AGTCAATAAA | TGATTCCACC | 420 |
| ACAATGAAAA | CCCTTATCTT | TAGTAGATTC | TCATTTAACC | TCGTACTATT | GGCGGTTGTA | 480 |
| GACTACCAGA | TAATAACACG | ATGCATCTCC | TCCATATATA | CAAACCAAAA | GAGTGATATT | 540 |
| GAATCCACAT | CCCTTTACCT | GATACAAGTA | ATGGAGTTTA | CCATGCTTTT | GATTGATTTG | 600 |
| CTAAATTTAT | TCCTACAGAC | TTGTTTGAAT | TTCTGGGAAT | TTTATCGCTC | ACAACAAAGT | 660 |
| CTGTCTAATG | AGAACAACCA | TATTGTCCAT | GGCGATCCTA | CAGATGAAAA | CACGGTTGAG | 720 |
| TCTGATCAAT | CTCAGCCAGT | GCTGAATGAC | GACGACGATG | ACGACGATGA | TGATAGACAA | 780 |
| TTTACCGGCC | TGGAGGGTAA | ATTCATGTAT | GAAAAAGCAA | TTGACGTATT | CACAAGATTC | 840 |
| TTAAAAACGG | CACTTCATTT | GTCTATGCTA | ATACCATTTA | GGATGCCTAT | GATGCTTTTG | 900 |
| AAAGATGTGG | TGTGGGATAT | CTTGGCACTA | TATCAAAGTG | GCACAAGTTT | GTGGAAAATC | 960 |
| TGGAGAAATA | ACAAACAGCT | CGACGACACT | CTTGTCACTG | TCACCGTAGA | ACAGCTACAA | 1020 |
| AATTCTGCAA | ATGATGACAA | TATTTGTATC | ATTTGTATGG | ATGAGTTAAT | ACATTCTCCA | 1080 |
| AACCAGCAGA | CGTGGAAGAA | TAAAAACAAG | AAACCCAAAA | GGTTACCTTG | TGGCCACATA | 1140 |
| CTTCATTTGT | CGTGTTTAAA | GAATTGGATG | GAACGTTCTC | AGACTTGTCC | TATTTGTAGA | 1200 |
| TTGCCTGTCT | TTGATGAAAA | AGGTAATGTT | GTGCAAACGA | CTTTCACTTC | CAATAGTGAT | 1260 |
| ATCACGACAC | AGACCACCGT | AACAGATAGC | ACTGGGATAG | CGACAGATCA | ACAAGGTTTC | 1320 |
| GCAAACGAAG | TAGATCTACT | TCCCACAAGA | ACAACTTCCC | CTGATATAAG | GATAGTGCCT | 1380 |
| ACTCAAAATA | TAGACACATT | AGCAATGAGA | ACAAGGTCAA | CCTCTACACC | ATCTCCTACG | 1440 |
| TGGTATACGT | TCCCATTACA | TAAAACTGGT | GATAATTCTG | TTGGGTCAAG | CCGATCAGCC | 1500 |
| TACGAATTTT | TGATCACAAA | TTCAGATGAG | AAAGAAAATG | GTATTCCTGT | CAAATTAACA | 1560 |
| ATAGAAAATC | ACGAAGTAAA | TTCTCTGCAT | GGAGACGGGG | GCGAGCAAAT | TGCCAAGAAA | 1620 |
| ATTGTCATAC | AGATAAAATT | TATCCAGCAT | ATCTAG | | | 1656 |

(2) INFORMATION FOR SEQ ID NO:8:

(i) SEQUENCE CHARACTERISTICS:
        (A) LENGTH: 95 amino acids
        (B) TYPE: amino acid
        (D) TOPOLOGY: linear (ii) MOLECULE TYPE: peptide (xi) SEQUENCE DESCRIPTION: SEQ ID NO:8:

Met Gly Leu Asp Thr Asp Val Asp Tyr Glu Thr Ala Phe Ile His Tyr
1               5                   10                  15

Arg Leu Ala Ser Glu Gln Gln His Ser Ala Gln Ala Met Phe Asn Leu
            20                  25                  30

Gly Tyr Met His Glu Lys Gly Leu Gly Ile Lys Gln Asp Ile His Leu
        35                  40                  45

```
Ala Lys Arg Phe Tyr Asp Met Ala Ala Val Ser Gln Pro Arg Cys Thr
 50                  55                  60

Ser Ser Ser Leu Pro Ser Pro Leu Gln Ile Gly His Arg Leu Phe Leu
 65                  70                  75                  80

Ala Val His Thr Gly Asn Lys His Ser Arg Tyr Val Leu Pro Thr
                 85                  90                  95
```

(2) INFORMATION FOR SEQ ID NO:9:

(i) SEQUENCE CHARACTERISTICS:
        (A) LENGTH: 2556 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

```
TTCCGGCGGC ACGGACGAGA AGCCGAGCGG CAAGGGCGG CGGGATGCCG GGGACAAGGA      60

CAAAGAACTG GAGCTGTCTG AAGAGGATAA ACAGCTTCAA GATGAACTGG TGATGCTCGT     120

GGAACGACTA GGGGAGAAGG ATACATCCCT GTATCGACCA GCGCTGGAGG AATTGCGAAG     180

GCAGATTCGT TCTTCTACAA CTTCCATGAC TTCAGTGCCC AAGCCTCTCA AATTTCTGCG     240

TCCACACTAT GGCAAACTGA AGGAAATCTA TGAGAACATG GCCCCTGGGG AGAATAAGCG     300

TTTTGCTGCT GACATCATCT CCGTTTTGGC CATGACCATG AGTGGGGAGC GTGAGTGCCT     360

CAAGTATCGG CTAGTGGGCT CCCAGGAGGA ATTGGCATCA TGGGGTCATG AGTATGTCAG     420

GCATCTGGCA GGAGAAGTGG CTAAGGAGTG GCAGGAGCTG GATGACGCAG AGAAGGTCCA     480

GCGGGAGCCT CTGCTCACTC TGGTGAAGGA AATCGTCCCC TATAACATGG CCCACAATGC     540

AGAGCATGAG GCTTGCGACC TGCTTATGGA AATTGAGCAG GTGGACATGC TGGAGAAGGA     600

CATTGATGAA AATGCATCTG CAAAGGTCTG CCTTTATCTC ACCAGTTGTG TAAATTACGT     660

GCCTGAGCCT GAGAACTCAG CCCTACTGCG TTGTGCCCTG GGTGTGTTCC GAAAGTTTAG     720

CCGCTTCCCT GAAGCTCTGA GATTGGCATT GATGCTCAAT GACATGGAGT TGGTAGAAGA     780

CTCTTCCTCC TGCAAGGATG TGGTAGTACA GAAACAGATG GCATTCATGC TAGGCCGGCA     840

TGGGGTGTTC CTGGAGCTGA GTGAAGATGT CGAGGAGTAT GAGGACCTGA CAGAGATCAT     900

GTCCAATGTA CAGCTCAACA GCAACTTCTT GGCCTTAGCT CGGGAGCTGG ACATCATGGA     960

GCCCAAGGTG CCTGATGACA TCTACAAAAC CCACCTAGAA ACAACAGGT TTGGGGGCAG    1020

TGGCTCTCAG GTGGACTCTG CCCGCATGAA CCTGGCCTCC TCTTTTGTGA ATGGCTTTGT    1080

GAATGCAGCT TTTGGCCAAG ACAAGCTGCT AACAGATGAT GGCAACAAAT GGCTTTACAA    1140

GAACAAGGAC CACGGAATGT TGAGTGCAGC TGCATCTCTT GGGATGATTC TGCTGTGGGA    1200

TGTGGATGGT GGCCTCACCC AGATTGACAA GTACCTGTAC TCCTCTGAGG ACTACATTAA    1260

GTCAGGAGCT CTTCTTGCCT GTGGCATAGT GAACTCTGGG GTCCGGAATG AGTGTGACCC    1320

TGCTCTGGCA CTGCTCTCAG ACTATGTTCT CCACAACAGC AACACCATGA GACTTGGTTC    1380

CATCTTTGGG CTAGGCTTGG CTTATGCTGG CTCAAATCGT GAAGATGTCC TAACACTGCT    1440

GCTGCCTGTG ATGGGAGATT CAAAGTCCAG CATGGAGGTG GCAGGTGTCA CAGCTTTAGC    1500

CTGTGGAATG ATAGCAGTAG GTCCTGCAA TGGAGATGTA ACTTCCACTA TCCTTCAGAC    1560

CATCATGGAG AAGTCAGAGA CTGAGCTCAA GGATACTTAT GCTCGTTGGC TTCCTCTTGG    1620

ACTGGGTCTC AACCACCTGG GGAAGGGTGA GGCCATCGAG GCAATCCTGG CTGCACTGGA    1680

GGTTGTGTCA GAGCCATTCC GCAGTTTTGC CAACACACTG GTGGATGTGT GTGCATATGC    1740
```

```
AGGCTCTGGG AATGTGCTGA AGGTGCAGCA GCTGCTCCAC ATTTGTAGCG AACACTTTGA      1800

CTCCAAAGAG AAGGAGGAAG ACAAAGACAA GAAGGAAAAG AAAGACAAGG ACAAGAAGGA      1860

AGCCCCTGCT GACATGGGAG CACATCAGGG AGTGGCTGTT CTGGGGATTG CCCTTATTGC      1920

TATGGGGGAG GAGATTGGTG CAGAGATGGC ATTACGAACC TTTGGCCACT TGCTGAGATA      1980

TGGGGAGCCT ACACTCCGGA GGGCTGTACC TTTAGCACTG GCCCTCATCT CTGTTTCAAA      2040

TCCACGACTC AACATCCTGG ATACCCTAAG CAAATTCTCT CATGATGCTG ATCCAGAAGT      2100

TTCCTATAAC TCCATTTTTG CCATGGGCAT GGGCATGGTG GGCAGTGGTA CCAATAATGC      2160

CCGTCTGGCT GCAATGCTGC GCCAGTTAGC TCAATATCAT GCCAAGGACC CAAACAACCT      2220

CTTCATGGTG CGCTTGGCAC AGGGCCTGAC ACATTTAGGG AAGGGCACCC TTACCCTCTG      2280

CCCCTACCAC AGCGACCGGC AGCTTATGAG CCAGGTGGCC GTGGCTGGAC TGCTCACTGT      2340

GCTTGTCTCT TTCCTGGATG TTCGAAACAT TATTCTAGGC AAATCACACT ATGTATTGTA      2400

TGGGCTGGTG GCTGCCATGC AGCCCCGAAT GCTGGTTACG TTTGATGAGG AGCTGCGGCC      2460

ATTGCCAGTG TCTGTCCGTG TGGGCCAGGC AGTGGATGTG GTGGGCCAGG CTGGCAAGCC      2520

GAAGACTATC ACAGGGTTCC AGACGCATAC AACCCC                                2556
```

(2) INFORMATION FOR SEQ ID NO:10:

(i) SEQUENCE CHARACTERISTICS:
        (A) LENGTH: 853 amino acids
        (B) TYPE: amino acid
        (D) TOPOLOGY: linear (ii) MOLECULE TYPE: protein (xi) SEQUENCE DESCRIPTION: SEQ ID NO:10:

```
Met Leu Val Glu Arg Leu Gly Glu Lys Asp Thr Ser Leu Tyr Arg Pro
 1               5                  10                  15

Ala Leu Glu Glu Leu Arg Arg Gln Ile Arg Ser Ser Thr Thr Ser Met
                20                  25                  30

Thr Ser Val Pro Lys Pro Leu Lys Phe Leu Arg Pro His Tyr Gly Lys
         35                  40                  45

Leu Lys Glu Ile Tyr Glu Asn Met Ala Pro Gly Glu Asn Lys Arg Phe
     50                  55                  60

Ala Ala Asp Ile Ile Ser Val Leu Ala Met Thr Met Ser Gly Glu Arg
 65                  70                  75                  80

Glu Cys Leu Lys Tyr Arg Leu Val Gly Ser Gln Glu Glu Leu Ala Ser
                85                  90                  95

Trp Gly His Glu Tyr Val Arg His Leu Ala Gly Glu Val Ala Lys Glu
            100                 105                 110

Trp Gln Glu Leu Asp Asp Ala Glu Lys Val Gln Arg Glu Pro Leu Leu
        115                 120                 125

Thr Leu Val Lys Glu Ile Val Pro Tyr Asn Met Ala His Asn Ala Glu
    130                 135                 140

His Glu Ala Cys Asp Leu Leu Met Glu Ile Glu Gln Val Asp Met Leu
145                 150                 155                 160

Glu Lys Asp Ile Asp Glu Asn Ala Ser Ala Lys Val Cys Leu Tyr Leu
                165                 170                 175

Thr Ser Cys Val Asn Tyr Val Pro Glu Pro Glu Asn Ser Ala Leu Leu
            180                 185                 190

Arg Cys Ala Leu Gly Val Phe Arg Lys Phe Ser Arg Phe Pro Glu Ala
        195                 200                 205
```

-continued

```
Leu Arg Leu Ala Leu Met Leu Asn Asp Met Glu Leu Val Glu Asp Ser
    210                 215                 220

Ser Ser Cys Lys Asp Val Val Gln Lys Gln Met Ala Phe Met Leu
225                 230                 235                 240

Gly Arg His Gly Val Phe Leu Glu Leu Ser Glu Asp Val Glu Glu Tyr
                    245                 250                 255

Glu Asp Leu Thr Glu Ile Met Ser Asn Val Gln Leu Asn Ser Asn Phe
                260                 265                 270

Leu Ala Leu Ala Arg Glu Leu Asp Ile Met Glu Pro Lys Val Pro Asp
            275                 280                 285

Asp Ile Tyr Lys Thr His Leu Glu Asn Asn Arg Phe Gly Gly Ser Gly
    290                 295                 300

Ser Gln Val Asp Ser Ala Arg Met Asn Leu Ala Ser Ser Phe Val Asn
305                 310                 315                 320

Gly Phe Val Asn Ala Ala Phe Gly Gln Asp Lys Leu Leu Thr Asp Asp
                    325                 330                 335

Gly Asn Lys Trp Leu Tyr Lys Asn Lys Asp His Gly Met Leu Ser Ala
                340                 345                 350

Ala Ala Ser Leu Gly Met Ile Leu Leu Trp Asp Val Asp Gly Gly Leu
            355                 360                 365

Thr Gln Ile Asp Lys Tyr Leu Tyr Ser Ser Glu Asp Tyr Ile Lys Ser
    370                 375                 380

Gly Ala Leu Leu Ala Cys Gly Ile Val Asn Ser Gly Val Arg Asn Glu
385                 390                 395                 400

Cys Asp Pro Ala Leu Ala Leu Leu Ser Asp Tyr Val Leu His Asn Ser
                    405                 410                 415

Asn Thr Met Arg Leu Gly Ser Ile Phe Gly Leu Gly Leu Ala Tyr Ala
                420                 425                 430

Gly Ser Asn Arg Glu Asp Val Leu Thr Leu Leu Leu Pro Val Met Gly
            435                 440                 445

Asp Ser Lys Ser Ser Met Glu Val Ala Gly Val Thr Ala Leu Ala Cys
    450                 455                 460

Gly Met Ile Ala Val Gly Ser Cys Asn Gly Asp Val Thr Ser Thr Ile
465                 470                 475                 480

Leu Gln Thr Ile Met Glu Lys Ser Glu Thr Glu Leu Lys Asp Thr Tyr
                    485                 490                 495

Ala Arg Trp Leu Pro Leu Gly Leu Gly Leu Asn His Leu Gly Lys Gly
                500                 505                 510

Glu Ala Ile Glu Ala Ile Leu Ala Ala Leu Glu Val Val Ser Glu Pro
            515                 520                 525

Phe Arg Ser Phe Ala Asn Thr Leu Val Asp Val Cys Ala Tyr Ala Gly
    530                 535                 540

Ser Gly Asn Val Leu Lys Val Gln Gln Leu Leu His Ile Cys Ser Glu
545                 550                 555                 560

His Phe Asp Ser Lys Glu Lys Glu Asp Lys Asp Lys Lys Glu Lys
                    565                 570                 575

Lys Asp Lys Asp Lys Lys Glu Ala Pro Ala Asp Met Gly Ala His Gln
                580                 585                 590

Gly Val Ala Val Leu Gly Ile Ala Leu Ile Ala Met Gly Glu Glu Ile
            595                 600                 605

Gly Ala Glu Met Ala Leu Arg Thr Phe Gly His Leu Leu Arg Tyr Gly
    610                 615                 620

Glu Pro Thr Leu Arg Arg Ala Val Pro Leu Ala Leu Ala Leu Ile Ser
625                 630                 635                 640
```

```
Val Ser Asn Pro Arg Leu Asn Ile Leu Asp Thr Leu Ser Lys Phe Ser
                645                 650                 655
His Asp Ala Asp Pro Glu Val Ser Tyr Asn Ser Ile Phe Ala Met Gly
                660                 665                 670
Met Gly Met Val Gly Ser Gly Thr Asn Asn Ala Arg Leu Ala Ala Met
            675                 680                 685
Leu Arg Gln Leu Ala Gln Tyr His Ala Lys Asp Pro Asn Asn Leu Phe
        690                 695                 700
Met Val Arg Leu Ala Gln Gly Leu Thr His Leu Gly Lys Gly Thr Leu
705                 710                 715                 720
Thr Leu Cys Pro Tyr His Ser Asp Arg Gln Leu Met Ser Gln Val Ala
                725                 730                 735
Val Ala Gly Leu Leu Thr Val Leu Val Ser Phe Leu Asp Val Arg Asn
                740                 745                 750
Ile Ile Leu Gly Lys Ser His Tyr Val Leu Tyr Gly Leu Val Ala Ala
                755                 760                 765
Met Gln Pro Arg Met Leu Val Thr Phe Asp Glu Glu Leu Arg Pro Leu
        770                 775                 780
Pro Val Ser Val Arg Val Gly Gln Ala Val Asp Val Val Gly Gln Ala
785                 790                 795                 800
Gly Lys Pro Lys Thr Ile Thr Gly Phe Gln Thr His Thr Thr Pro Val
                805                 810                 815
Leu Leu Ala His Gly Glu Arg Ala Glu Leu Ala Thr Glu Glu Phe Leu
                820                 825                 830
Pro Val Thr Pro Ile Leu Glu Gly Phe Val Ile Phe Gly Arg Thr Pro
                835                 840                 845
Ile Met Ile Ser Lys
    850

(2) INFORMATION FOR SEQ ID NO:11:

(i) SEQUENCE CHARACTERISTICS:
        (A) LENGTH: 2731 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

TGCGCGCGCA GCGGGCCGGC AGTGGCGGCG GAGATGGAGG AGGGAGGCCG GGACAAGGCG      60

CCGGTGCAGC CCCAGCAGTC TCCAGCGGCG GCCCCCGGCG GCACGGACGA GAAGCCGAGC     120

GGCAAGGAGC GGCGGGATGC CGGGGACAAG GACAAAGAAC AGGAGCTGTC TGAAGAGGAT     180

AAACAGCTTC AAGATGAACT GGAGATGCTC GCGGAACGAC TAGGGGAGAA GGATACATCC     240

CTGTATCGAC CAGCGCTGGA GGAATTGCGA AGGCAGATTC GTTCTTCTAC AACTTCCATG     300

ACTTCAGTGC CCAAGCCTCT CAAATTTCTG CGTCCACACT ATGGCAAACT GAAGGAAATC     360

TATGAGAACA TGGCCCCTGG GGAGAATAAG CGTTTTGCTG CTGACATCAT CTCCGTTTTG     420

GCCATGACCA TGAGTGGGGA GCGTGAGTGC CTCAAGTATC GGCTAGTGGG CTCCCAGGAG     480

GAATTGGCAT CATGGGGTCA TGAGTATGTC AGGCATCTGG CAGGAGAAGT GGCTAAGGAG     540

TGGCAGGAGC TGGATGACGC AGAGAAGGTC CAGCGGGAGC CTCTGCTCAC TCTGGTGAAG     600

GAAATCGTCC CCTATAACAT GGCCCACAAT GCAGAGCATG AGGCTTGCGA CCTGCTTATG     660

GAAATTGAGC AGGTGGACAT GCTGGAGAAG GACATTGATG AAAATGCATA TGCAAAGGTC     720
```

```
TGCCTTTATC TCACCAGTTG TGTGAATTAC GTGCCTGAGC CTGAGAACTC AGCCCTACTG      780

CGTTGTGCCC TGGGTGTGTT CCGAAAGTTT AGCCGCTTCC CTGAAGCTCT GAGATTGGCA      840

TTGATGCTCA ATGACATGGA GTTGGTAGAA GACATCTTCA CCTCCTGCAA GGATGTGGTA      900

GTACAGAAAC AGATGGCATT CATGCTAGGC CGGCATGGGG TGTTCCTGGA GCTGAGTGAA      960

GATGTCGAGG AGTATGAGGA CCTGACAGAG ATCATGTCCA ATGTACAGCT CAACAGCAAC     1020

TTCTTGGCCT TAGCTCGGGA GCTGGACATC ATGGAGCCCA AGGTGCCTGA TGACATCTAC     1080

AAAACCCACC TAGAGAACAA CAGGTTTGGG GGCAGTGGCT CTCAGGTGGA CTCTGCCCGC     1140

ATGAACCTGG CCTCCTCTTT TGTGAATGGC TTTGTGAATG CAGCTTTTGG CCAAGACAAG     1200

CTGCTAACAG ATGATGGCAA CAAATGGCTT TACAAGAACA AGGACCACGG AATGTTGAGT     1260

GCAGCTGCAT CTCTTGCGAT GATTCTGCTG TGGGATGTGG ATGGTGGCCT CACCCAGATT     1320

GACAAGTACC TGTACTCCTC TGAGGACTAC ATTAAGTCAG GAGCTCTTCT TGCCTGTGGC     1380

ATAGTGAACT CTGGGGTCCG GAATGAGTGT GACCCTGCTC TGGCACTGCT CTCAGACTAT     1440

GTTCTCCACA ACAGCAACAC CATGAGACTT GGTTCCATCT TTGGGCTAGG CTTGGCTTAT     1500

GCTGGCTCAA ATCGTGAAGA TGTCCTAACA CTGCTGCTGC CTGTGATGGG AGATTCAAAG     1560

TCCAGCATGG AGGTGGCAGG TGTCACAGCT TTAGCCTGTG GAATGATAGC AGTAGGGTCC     1620

TGCAATGGAG ATGTAACTTC CACTATCCTT CAGACCATCA TGGAGAAGTC AGAGACTGAG     1680

CTCAAGGATA CTTATGCTCG TTGGCTTCCT CTTGGACTGG GTCTCAACCA CCTGGGGAAG     1740

GGTGAGGCCA TCGAGGCAAT CCTGGCTGCA CTGGAGGTTG TGTCAGAGCC ATTCCGCAGT     1800

TTTGCCAACA CACTGGTGGA TGTGTGTGCA TATGCAGGCT CTGGGAATGT GCTGAAGGTG     1860

CAGCAGCTGC TCCACATTTG TAGCGAACAC TTTGACTCCA AGAGAAGGA GGAAGACAAA     1920

GACAAGAAGG AAAAGAAAGA CAAGGACAAG AAGGAAGCCC CTGCTGACAT GGGAGCACAT     1980

CAGGGAGTGG CTGTTCTGGG GATTGCCCTT ATTGCTATGG GGAGGAGAT TGGTGCAGAG     2040

ATGGCATTAC GAACCTTTGG CCACTTGCTG AGATATGGGG AGCCTACACT CCGGAGGGCT     2100

GTACCTTTAG CACTGGCCCT CATCTCTGTT TCAAATCCAC GACTCAACAT CCTGGATACC     2160

CTAAGCAAAT TCTCTCATGA TGCTGATCCA GAAGTTTCCT ATAACTCCAT TTTTGCCATG     2220

GGCATGGTGG GCAGTGGTAC CAATAATGCC CGTCTGGCTG CAATGCTGCG CCAGTTAGCT     2280

CAATATCATG CCAAGGACCC AAACAACCTC TTCATGGTGC GCTTGGCACA GGGCCTGACA     2340

CATTTAGGGA AGGGCACCCT TACCCTCTGC CCCTACCACA GCGACCGGCA GCTTATGAGC     2400

CAGGTGGCCG TGGCTGGACT GCTCACTGTG CTTGTCTCTT TCCTGGATGT TCGAAACATT     2460

ATTCTAGGCA AATCACACTA TGTATTGTAT GGGCTGGTGG CTGCCATGCA GCCCCGAATG     2520

CTGGTTACGT TTGATGAGGA GCTGCGGCCA TTGCCAGTGT CTGTCCGTGT GGGCCAGGCA     2580

GTGGATGTGG TGGGCCAGGC TGGCAAGCCG AAGACTATCA CAGGGTTCCA GACGCATACA     2640

ACCCCAGTGT TGTTGGCCCA CGGGGAACGG GCAGAATTGG CCACTGAGGA GTTTCTTCCT     2700

GTTACCCCCA TTCTGGAAGG TTTTGTTATC C                                    2731
```

(2) INFORMATION FOR SEQ ID NO:12:

(i) SEQUENCE CHARACTERISTICS:
        (A) LENGTH: 908 amino acids
        (B) TYPE: amino acid
        (D) TOPOLOGY: linear (ii) MOLECULE TYPE: protein (xi) SEQUENCE DESCRIPTION: SEQ ID NO:12:

-continued

```
Met Glu Gly Gly Arg Asp Lys Ala Pro Val Gln Pro Gln Gln Ser
 1               5                  10                  15

Pro Ala Ala Ala Pro Gly Gly Thr Asp Glu Lys Pro Ser Gly Lys Glu
                20                  25                  30

Arg Arg Asp Ala Gly Asp Lys Asp Lys Glu Gln Glu Leu Ser Glu Glu
            35                  40                  45

Asp Lys Gln Leu Gln Asp Glu Leu Glu Met Leu Ala Glu Arg Leu Gly
     50                  55                  60

Glu Lys Asp Thr Ser Leu Tyr Arg Pro Ala Leu Glu Glu Leu Arg Arg
 65                  70                  75                  80

Gln Ile Arg Ser Ser Thr Thr Ser Met Thr Ser Val Pro Lys Pro Leu
                85                  90                  95

Lys Phe Leu Arg Pro His Tyr Gly Lys Leu Lys Glu Ile Tyr Glu Asn
                100                 105                 110

Met Ala Pro Gly Glu Asn Lys Arg Phe Ala Ala Asp Ile Ile Ser Val
                115                 120                 125

Leu Ala Met Thr Met Ser Gly Glu Arg Glu Cys Leu Lys Tyr Arg Leu
            130                 135                 140

Val Gly Ser Gln Glu Glu Leu Ala Ser Trp Gly His Glu Tyr Val Arg
145                 150                 155                 160

His Leu Ala Gly Glu Val Ala Lys Glu Trp Gln Glu Leu Asp Asp Ala
                165                 170                 175

Glu Lys Val Gln Arg Glu Pro Leu Leu Thr Leu Val Lys Glu Ile Val
            180                 185                 190

Pro Tyr Asn Met Ala His Asn Ala Glu His Glu Ala Cys Asp Leu Leu
            195                 200                 205

Met Glu Ile Glu Gln Val Asp Met Leu Glu Lys Asp Ile Asp Glu Asn
210                 215                 220

Ala Tyr Ala Lys Val Cys Leu Tyr Leu Thr Ser Cys Val Asn Tyr Val
225                 230                 235                 240

Pro Glu Pro Glu Asn Ser Ala Leu Leu Arg Cys Ala Leu Gly Val Phe
                245                 250                 255

Arg Lys Phe Ser Arg Phe Pro Glu Ala Leu Arg Leu Ala Leu Met Leu
            260                 265                 270

Asn Asp Met Glu Leu Val Glu Asp Ile Phe Thr Ser Cys Lys Asp Val
            275                 280                 285

Val Val Gln Lys Gln Met Ala Phe Met Leu Gly Arg His Gly Val Phe
290                 295                 300

Leu Glu Leu Ser Glu Asp Val Glu Glu Tyr Glu Asp Leu Thr Glu Ile
305                 310                 315                 320

Met Ser Asn Val Gln Leu Asn Ser Asn Phe Leu Ala Leu Ala Arg Glu
                325                 330                 335

Leu Asp Ile Met Glu Pro Lys Val Pro Asp Asp Ile Tyr Lys Thr His
            340                 345                 350

Leu Glu Asn Asn Arg Phe Gly Gly Ser Gly Ser Gln Val Asp Ser Ala
            355                 360                 365

Arg Met Asn Leu Ala Ser Ser Phe Val Asn Gly Phe Val Asn Ala Ala
            370                 375                 380

Phe Gly Gln Asp Lys Leu Leu Thr Asp Asp Gly Asn Lys Trp Leu Tyr
385                 390                 395                 400

Lys Asn Lys Asp His Gly Met Leu Ser Ala Ala Ser Leu Ala Met
                405                 410                 415

Ile Leu Leu Trp Asp Val Asp Gly Gly Leu Thr Gln Ile Asp Lys Tyr
                420                 425                 430
```

-continued

```
Leu Tyr Ser Ser Glu Asp Tyr Ile Lys Ser Gly Ala Leu Leu Ala Cys
        435                 440                 445

Gly Ile Val Asn Ser Gly Val Arg Asn Glu Cys Asp Pro Ala Leu Ala
    450                 455                 460

Leu Leu Ser Asp Tyr Val Leu His Asn Ser Asn Thr Met Arg Leu Gly
465                 470                 475                 480

Ser Ile Phe Gly Leu Gly Leu Ala Tyr Ala Gly Ser Asn Arg Glu Asp
                485                 490                 495

Val Leu Thr Leu Leu Pro Val Met Gly Asp Ser Lys Ser Ser Met
            500                 505                 510

Glu Val Ala Gly Val Thr Ala Leu Ala Cys Gly Met Ile Ala Val Gly
        515                 520                 525

Ser Cys Asn Gly Asp Val Thr Ser Thr Ile Leu Gln Thr Ile Met Glu
    530                 535                 540

Lys Ser Glu Thr Glu Leu Lys Asp Thr Tyr Ala Arg Trp Leu Pro Leu
545                 550                 555                 560

Gly Leu Gly Leu Asn His Leu Gly Lys Gly Glu Ala Ile Glu Ala Ile
                565                 570                 575

Leu Ala Ala Leu Glu Val Val Ser Glu Pro Phe Arg Ser Phe Ala Asn
            580                 585                 590

Thr Leu Val Asp Val Cys Ala Tyr Ala Gly Ser Gly Asn Val Leu Lys
        595                 600                 605

Val Gln Gln Leu Leu His Ile Cys Ser Glu His Phe Asp Ser Lys Glu
    610                 615                 620

Lys Glu Glu Asp Lys Asp Lys Lys Glu Lys Asp Lys Asp Lys Lys
625                 630                 635                 640

Glu Ala Pro Ala Asp Met Gly Ala His Gln Gly Val Ala Val Leu Gly
                645                 650                 655

Ile Ala Leu Ile Ala Met Gly Glu Glu Ile Gly Ala Glu Met Ala Leu
            660                 665                 670

Arg Thr Phe Gly His Leu Leu Arg Tyr Gly Glu Pro Thr Leu Arg Arg
        675                 680                 685

Ala Val Pro Leu Ala Leu Ala Leu Ile Ser Val Ser Asn Pro Arg Leu
    690                 695                 700

Asn Ile Leu Asp Thr Leu Ser Lys Phe Ser His Asp Ala Asp Pro Glu
705                 710                 715                 720

Val Ser Tyr Asn Ser Ile Phe Ala Met Gly Met Val Gly Ser Gly Thr
                725                 730                 735

Asn Asn Ala Arg Leu Ala Ala Met Leu Arg Gln Leu Ala Gln Tyr His
            740                 745                 750

Ala Lys Asp Pro Asn Asn Leu Phe Met Val Arg Leu Ala Gln Gly Leu
        755                 760                 765

Thr His Leu Gly Lys Gly Thr Leu Thr Leu Cys Pro Tyr His Ser Asp
    770                 775                 780

Arg Gln Leu Met Ser Gln Val Ala Val Ala Gly Leu Leu Thr Val Leu
785                 790                 795                 800

Val Ser Phe Leu Asp Val Arg Asn Ile Ile Leu Gly Lys Ser His Tyr
                805                 810                 815

Val Leu Tyr Gly Leu Val Ala Ala Met Gln Pro Arg Met Leu Val Thr
            820                 825                 830

Phe Asp Glu Glu Leu Arg Pro Leu Pro Val Ser Val Arg Val Gly Gln
        835                 840                 845

Ala Val Asp Val Val Gly Gln Ala Gly Lys Pro Lys Thr Ile Thr Gly
```

```
                850               855                860
Phe Gln Thr His Thr Thr Pro Val Leu Leu Ala His Gly Glu Arg Ala
865                 870                 875                 880

Glu Leu Ala Thr Glu Glu Phe Leu Pro Val Thr Pro Ile Leu Glu Gly
                    885                 890                 895

Phe Val Ile Leu Arg Lys Asn Pro Asn Tyr Asp Leu
                900                 905
```

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCTGTTCTGG GGATTGCCCT TATTGC                                              26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCAGTTTTGG GTATTGCTTT GATTGC                                              26

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

GCNGTTYTGG GNATTGCNYT NATTGC                                            26

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GCTGTTCTGG GTATTGCCTT TATTGC                                            26

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

AGCCAGACGG GCATTATTGG TACCA                                                                25

(2) INFORMATION FOR SEQ ID NO:18:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:18:

AGCTAACCTT GCATTGTTAG TACCA                                                                25

(2) INFORMATION FOR SEQ ID NO:19:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:19:

AGCYANMCNK GCATTRTTRG TACCA                                                                25

(2) INFORMATION FOR SEQ ID NO:20:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:20:

AGCCAACCGT GCATTGTTGG TACCA                                                                25

(2) INFORMATION FOR SEQ ID NO:21:

(i) SEQUENCE CHARACTERISTICS:
         (A) LENGTH: 37 amino acids
         (B) TYPE: amino acid
         (D) TOPOLOGY: linear (ii) MOLECULE TYPE: polypeptide (xi) SEQUENCE DESCRIPTION: SEQ ID NO:21:

Ser Gly Gly Thr Asp Glu Lys Pro Ser Gly Lys Gly Arg Arg Asp Ala
 1               5                  10                  15

Gly Asp Lys Asp Lys Glu Leu Glu Leu Ser Glu Glu Asp Lys Gln Leu
            20                  25                  30

Gln Asp Glu Leu Val
         35

(2) INFORMATION FOR SEQ ID NO:22:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:22:

GATCCCCATG GCCTGCA                                                                       17

(2) INFORMATION FOR SEQ ID NO:23:

(i) SEQUENCE CHARACTERISTICS:
         (A) LENGTH: 9 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:23:

GGCCATGGG                                                                                 9

(2) INFORMATION FOR SEQ ID NO:24:

(i) SEQUENCE CHARACTERISTICS:
         (A) LENGTH: 40 base pairs
         (B) TYPE: nucleic acid
         (C) STRANDEDNESS: double
         (D) TOPOLOGY: linear (ii) MOLECULE TYPE: Genomic DNA (xi) SEQUENCE DESCRIPTION: SEQ ID NO:24:

ATGGTGCCAG AAAATAGAAG GAAACAGTTG GCAATTTTTG                                               40

(2) INFORMATION FOR SEQ ID NO:25:

(i) SEQUENCE CHARACTERISTICS:
         (A) LENGTH: 551 amino acids
         (B) TYPE: amino acid
         (D) TOPOLOGY: linear (ii) MOLECULE TYPE: polypeptide (xi) SEQUENCE DESCRIPTION: SEQ ID NO:25:

Met Val Pro Glu Asn Arg Arg Lys Gln Leu Ala Ile Phe Val Val Val
  1               5                  10                  15

Thr Tyr Leu Leu Thr Phe Tyr Cys Val Tyr Ser Ala Thr Lys Thr Ser
             20                  25                  30

Val Ser Phe Leu Gln Val Thr Leu Lys Leu Asn Glu Gly Phe Asn Leu
         35                  40                  45

Met Val Leu Ser Ile Phe Ile Leu Leu Asn Ser Thr Leu Leu Trp Gln
     50                  55                  60

Leu Leu Thr Lys Leu Leu Phe Gly Glu Leu Arg Leu Ile Glu His Glu
 65                  70                  75                  80

His Ile Phe Glu Arg Leu Pro Phe Thr Ile Ile Asn Thr Leu Phe Met
                 85                  90                  95

Ser Ser Leu Phe His Glu Arg Tyr Phe Phe Thr Val Ala Phe Phe Gly
            100                 105                 110

Leu Leu Leu Leu Tyr Leu Lys Val Phe His Trp Ile Leu Lys Asp Arg
        115                 120                 125

Leu Glu Ala Leu Leu Gln Ser Ile Asn Asp Ser Thr Thr Met Lys Thr
    130                 135                 140

Leu Ile Phe Ser Arg Phe Ser Phe Asn Leu Val Leu Leu Ala Val Val
145                 150                 155                 160

Asp Tyr Gln Ile Ile Thr Arg Cys Ile Ser Ser Ile Tyr Thr Asn Gln

-continued

```
                    165                 170                 175
Lys Ser Asp Ile Glu Ser Thr Ser Leu Tyr Leu Ile Gln Val Met Glu
                180                 185                 190

Phe Thr Met Leu Leu Ile Asp Leu Leu Asn Leu Phe Leu Gln Thr Cys
                195                 200                 205

Leu Asn Phe Trp Glu Phe Tyr Arg Ser Gln Gln Ser Leu Ser Asn Glu
            210                 215                 220

Asn Asn His Ile Val His Gly Asp Pro Thr Asp Glu Asn Thr Val Glu
225                 230                 235                 240

Ser Asp Gln Ser Gln Pro Val Leu Asn Asp Asp Asp Asp Asp Asp Asp
                245                 250                 255

Asp Asp Arg Gln Phe Thr Gly Leu Glu Gly Lys Phe Met Tyr Glu Lys
                260                 265                 270

Ala Ile Asp Val Phe Thr Arg Phe Leu Lys Thr Ala Leu His Leu Ser
                275                 280                 285

Met Leu Ile Pro Phe Arg Met Pro Met Met Leu Leu Lys Asp Val Val
                290                 295                 300

Trp Asp Ile Leu Ala Leu Tyr Gln Ser Gly Thr Ser Leu Trp Lys Ile
305                 310                 315                 320

Trp Arg Asn Asn Lys Gln Leu Asp Asp Thr Leu Val Thr Val Thr Val
                325                 330                 335

Glu Gln Leu Gln Asn Ser Ala Asn Asp Asp Asn Ile Cys Ile Ile Cys
                340                 345                 350

Met Asp Glu Leu Ile His Ser Pro Asn Gln Gln Thr Trp Lys Asn Lys
                355                 360                 365

Asn Lys Lys Pro Lys Arg Leu Pro Cys Gly His Ile Leu His Leu Ser
                370                 375                 380

Cys Leu Lys Asn Trp Met Glu Arg Ser Gln Thr Cys Pro Ile Cys Arg
385                 390                 395                 400

Leu Pro Val Phe Asp Glu Lys Gly Asn Val Val Gln Thr Thr Phe Thr
                405                 410                 415

Ser Asn Ser Asp Ile Thr Thr Gln Thr Thr Val Thr Asp Ser Thr Gly
                420                 425                 430

Ile Ala Thr Asp Gln Gln Gly Phe Ala Asn Glu Val Asp Leu Leu Pro
                435                 440                 445

Thr Arg Thr Thr Ser Pro Asp Ile Arg Ile Val Pro Thr Gln Asn Ile
                450                 455                 460

Asp Thr Leu Ala Met Arg Thr Arg Ser Thr Ser Thr Pro Ser Pro Thr
465                 470                 475                 480

Trp Tyr Thr Phe Pro Leu His Lys Thr Gly Asp Asn Ser Val Gly Ser
                485                 490                 495

Ser Arg Ser Ala Tyr Glu Phe Leu Ile Thr Asn Ser Asp Glu Lys Glu
                500                 505                 510

Asn Gly Ile Pro Val Lys Leu Thr Ile Glu Asn His Glu Val Asn Ser
                515                 520                 525

Leu His Gly Asp Gly Gly Glu Gln Ile Ala Lys Lys Ile Val Ile Pro
                530                 535                 540

Asp Lys Phe Ile Gln His Ile
545                 550
```